United States Patent
Bhavaraju et al.

(10) Patent No.: US 11,656,195 B2
(45) Date of Patent: May 23, 2023

(54) AUTOMATIC ANALYTE SENSOR CALIBRATION AND ERROR DETECTION

(71) Applicant: DexCom, Inc., San Diego, CA (US)

(72) Inventors: Naresh C. Bhavaraju, San Diego, CA (US); Becky L. Clark, San Diego, CA (US); Vincent P. Crabtree, San Diego, CA (US); Chris W. Dring, San Diego, CA (US); Arturo Garcia, Chula Vista, CA (US); Jason Halac, San Diego, CA (US); Jonathan Hughes, Encinitas, CA (US); Jeff Jackson, Poway, CA (US); Lauren Hruby Jepson, San Diego, CA (US); David I-Chun Lee, San Diego, CA (US); Ted Tang Lee, San Diego, CA (US); Rui Ma, San Diego, CA (US); Zebediah L. McDaniel, San Diego, CA (US); Jason Mitchell, Poway, CA (US); Andrew Attila Pal, San Diego, CA (US); Daiting Rong, San Diego, CA (US); Disha B. Sheth, Oceanside, CA (US); Peter C. Simpson, Cardiff, CA (US); Stephen J. Vanslyke, Carlsbad, CA (US); Matthew D. Wightlin, San Diego, CA (US); Anna Leigh Davis, Cardiff by the Sea, CA (US); Hari Hampapuram, San Diego, CA (US); Aditya Sagar Mandapaka, San Diego, CA (US); Alexander Leroy Teeter, Poway, CA (US); Liang Wang, La Jolla, CA (US)

(73) Assignee: Dexcom, Inc., San Diego, CA (US)

( * ) Notice: Subject to any disclaimer, the term of this patent is extended or adjusted under 35 U.S.C. 154(b) by 486 days.

(21) Appl. No.: 16/402,101

(22) Filed: May 2, 2019

(65) Prior Publication Data
US 2019/0339222 A1 Nov. 7, 2019

Related U.S. Application Data

(63) Continuation of application No. 16/402,013, filed on May 2, 2019.
(Continued)

(51) Int. Cl.
G01N 27/327 (2006.01)
A61B 5/145 (2006.01)
A61B 5/1495 (2006.01)

(52) U.S. Cl.
CPC ....... *G01N 27/3274* (2013.01); *A61B 5/1495* (2013.01); *A61B 5/14532* (2013.01); *A61B 2560/0223* (2013.01)

(58) Field of Classification Search
None
See application file for complete search history.

(56) References Cited

U.S. PATENT DOCUMENTS

| 7,996,158 B2 | 8/2011 | Hayter et al. |
| 10,638,979 B2 | 5/2020 | Gupta et al. |

(Continued)

FOREIGN PATENT DOCUMENTS

WO WO-2018204476 A1 * 11/2018 ........... A61B 5/0022

OTHER PUBLICATIONS

Massart et al., [Eds.] *Handbook of chemometrics and qualimetrics*, Elsevier Science (1998), vol. 20 A & B; Table of Contents in 10 pages.
(Continued)

*Primary Examiner* — Manuel A Rivera Vargas
*Assistant Examiner* — Yaritza H Perez Bermudez
(74) *Attorney, Agent, or Firm* — Schwegman Lundberg & Woessner, P.A.

(57) ABSTRACT

Systems and methods are provided that address the need to frequently calibrate analyte sensors, according to implemen-
(Continued)

tation. In more detail, systems and methods provide a preconnected analyte sensor system that physically combines an analyte sensor to measurement electronics during the manufacturing phase of the sensor and in some cases in subsequent life phases of the sensor, so as to allow an improved recognition of sensor environment over time to improve subsequent calibration of the sensor.

36 Claims, 20 Drawing Sheets

Related U.S. Application Data

(60) Provisional application No. 62/666,606, filed on May 3, 2018.

(56) References Cited

U.S. PATENT DOCUMENTS

| | | |
|---|---|---|
| 2004/0267103 A1 | 12/2004 | Li et al. |
| 2008/0066305 A1* | 3/2008 | Wang ................ G01N 27/3272 |
| | | 29/846 |
| 2008/0275365 A1 | 11/2008 | Guthrie et al. |
| 2009/0247856 A1 | 10/2009 | Boock et al. |
| 2010/0081909 A1 | 4/2010 | Budiman et al. |
| 2010/0217557 A1 | 8/2010 | Kamath et al. |
| 2010/0274515 A1 | 10/2010 | Hoss et al. |
| 2011/0027127 A1 | 2/2011 | Simpson et al. |
| 2011/0213225 A1* | 9/2011 | Bernstein ............. A61B 5/0017 |
| | | 600/309 |
| 2011/0320130 A1 | 12/2011 | Valdes et al. |
| 2012/0323098 A1* | 12/2012 | Moein ................ A61B 5/14532 |
| | | 29/832 |
| 2012/0328473 A1 | 12/2012 | Thomas et al. |
| 2013/0002278 A1 | 1/2013 | Martin et al. |
| 2013/0325352 A1 | 12/2013 | Greene et al. |
| 2014/0114156 A1 | 4/2014 | Böhm et al. |
| 2016/0015303 A1* | 1/2016 | Bernstein ................ A61B 5/01 |
| | | 600/347 |
| 2016/0081597 A1 | 3/2016 | Bhavaraju et al. |
| 2016/0298988 A1* | 10/2016 | Hahn .................... G01N 33/18 |
| 2017/0071511 A1* | 3/2017 | Garcia ................ A61B 5/1495 |
| 2017/0071512 A1 | 3/2017 | Garcia et al. |
| 2018/0008174 A1 | 1/2018 | Böhm et al. |
| 2019/0117133 A1 | 4/2019 | Halac et al. |
| 2019/0117138 A1 | 4/2019 | Budiman et al. |
| 2019/0274598 A1* | 9/2019 | Scott .................. A61B 5/14546 |
| 2019/0339221 A1 | 11/2019 | Bhavaraju et al. |
| 2019/0339223 A1 | 11/2019 | Bhavaraju et al. |
| 2019/0339224 A1 | 11/2019 | Bhavaraju et al. |
| 2020/0008719 A1 | 1/2020 | Bremer et al. |

OTHER PUBLICATIONS

International Search Report and Written Opinion dated Dec. 2, 2019 for Application No. PCT/US2019/030450.
Office Action from European Patent Application No. 19796328.3, dated Dec. 10, 2020, 3 pages.
NPL Search Results, Apr. 30, 2021, 1 page.

* cited by examiner

| PVP wt. % | PVP (mole) | PVP (mole) | % |
|---|---|---|---|
| 12 | 0.512 | 0.412 | 0.445887 |
| 12.5 | 0.51 | 0.442 | 0.464286 |
| 13 | 0.5189 | 0.4815 | 0.481307 |
| 13.5 | 0.510625 | 0.504 | 0.496735 |
| 14 | 0.512 | 0.503 | 0.495567 |
| 14.5 | 0.4956 | 0.465 | 0.484072 |
| 15 | 0.511625 | 0.5575 | 0.521454 |
| 15.5 | 0.4978 | 0.5585 | 0.528732 |
| 16 | 0.501625 | 0.583 | 0.537513 |

FIG. 17

AUTOMATIC ANALYTE SENSOR CALIBRATION AND ERROR DETECTION

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/402,013, filed May 2, 2019, which claims the benefit of U.S. Provisional Application No. 62/666,606, filed May 3, 2018. Each of the aforementioned applications is incorporated by reference herein in its entirety, and each is hereby expressly made a part of this specification.

TECHNICAL FIELD

The embodiments described herein relate generally to systems and methods for processing sensor data from continuous analyte sensors and for self-calibration.

BACKGROUND

Diabetes mellitus is a disorder in which the pancreas cannot create sufficient insulin (Type I or insulin-dependent) and/or in which insulin is not effective (Type II or non-insulin-dependent). In the diabetic state, the patient or user suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. It is not only unlikely that a person with diabetes will become aware of a dangerous condition in time to counteract it, but it is also likely that he or she will not know whether his or her blood glucose concentration value is going up (higher) or down (lower) based on conventional methods. Diabetics thus may be inhibited from making educated insulin therapy decisions.

Another device that some diabetics used to monitor their blood glucose is a continuous analyte sensor, e.g., a continuous glucose monitor (CGM). A CGM typically includes a sensor that is placed invasively, minimally invasively or non-invasively. The sensor measures the concentration of a given analyte within the body, e.g., glucose, and generates a raw signal using electronics associated with the sensor. The raw signal is converted into an output value that is rendered on a display. The output value that results from the conversion of the raw signal is typically expressed in a form that provides the user with meaningful information, and in which form users have become familiar with analyzing, such as blood glucose expressed in mg/dL.

The above discussion assumes the output value is reliable and true, and the same generally requires a significant degree of user interaction to ensure proper calibration. Typically, a calibration check is performed before the analyte sensor leaves the factory; during the calibration check, sensitivity values are derived in vitro. However, the calibration check only provides a snapshot of the sensitivity at a given point in time and does not take into account that sensor sensitivity changes over time. Moreover, two sensors that have the same result from the calibration check procedure can still act differently in use in a patient, as the values of sensitivity can diverge over time depending on conditions before and after use.

One way of accounting for this is by use of reference value checks during use, e.g., by self monitoring blood glucose meters. Many current CGMs rely heavily on such user interactions, confirming glucose concentration values before dosing insulin. However, additional user action adds a significant source of error in the monitoring and reduces convenience by requiring more action of the user than desired.

SUMMARY OF THE INVENTION

Systems and methods according to present principles address many of the issues above concerning the need to frequently calibrate analyte sensors, according to implementation. In more detail, systems and methods provide a preconnected analyte sensor system that physically combines an analyte sensor to measurement electronics during the manufacturing phase of the sensor and in some cases in subsequent life phases of the sensor.

In one embodiment, at a minimum the system includes an analyte sensor capable of measuring an analyte level in a host and measurement electronics containing a potentiostat circuit capable of placing a controlled voltage bias between two or more electrodes and measuring the amount of current that flows. The analyte sensor is preconnected to the measurement electronics.

There are also several optional features: a sensor interconnection module capable of securing an analyte sensor in position and/or robust electrical coupling, and a measurement electronics module which may include one or more of the following: a temperature measurement circuit capable of taking temperature readings from one or more temperature sensors, an impedance measurement circuit capable of detecting impedance values from the analyte sensor or other electrical components, a capacitive measurement circuit capable of detecting capacitance values from the analyte sensor or other electrical components, a motion detecting circuit using one or more sensors such as an accelerometer or gyroscope to detecting and quantifying physical motion and/or orientation, a humidity measurement circuit with one or more sensors able to measure humidity, a clock capable of keeping a measure of time, and/or a pressure measurement circuit with one or more pressure sensors capable of measuring pressure of a gas (e.g., barometric pressure) or changes in pressure applied to the device (e.g., force applied to a surface of a housing), and one or more processors capable of processing data. Other features may include one or more radios capable of wirelessly transmitting data, one or more display/status indicators capable of communicating data to a user, one or more data storage units capable of storing relevant information for future access, and one or more power sources (e.g., a battery) capable of delivering reliable power for use by the measurement electronics.

A preconnected analyte sensor can address various sources of error that may otherwise arise. These sources of error may involve both errors in accuracy and precision, which are key factors in determining the true value of a measurement performed by a measurement system. Accuracy can be described as the closeness of a measured value to a standard or known value. For example, when taking a width measurement of a known 1cm cube and a value obtained is 1.1 cm, the measurement is accurate to 0.1 cm. Precision is the degree to which repeated measurements under unchanged conditions show the same results. In the same cube example if three measurements are taken and the values obtained are 1.1 cm, 1.2 cm, and 1.0 cm the measurement is precise to within 0.1 cm. However, precision and accuracy error are compounded in the determination of the trueness of a measurement.

Precision and accuracy are not static factors that can impact errors in a measurement system. Rather, they are dynamic factors in which precision and accuracy can vary over time. Typically a model is used (e.g. linear, non-linear, etc.) to quantify a sensor response to signal, and so deviations to the precision and accuracy of the model used to quantify a sensor response add additional error in the conversion of a sensor signal to a reported value.

Therefore, preconnecting an analyte sensor system to measurement electronics in the manufacturing phase and then using the same configuration during the sensor use phase has several advantages.

The preconnected analyte sensor system can compensate for errors introduced by the accuracy and precision of manufacturing equipment. Variations in the manufacturing process may give rise to different values for various parameters that are measured (e.g., analyte sensitivity, baseline, impedance, capacitance, interferent sensitivity, etc.), and the errors resulting from these different parameter values are compounded into the error of the overall system. The more variations there are in the manufacturing setup, the more significant the consequences to the error introduced in the system. These variations may include: changes to equipment over time, frequency of equipment calibration, number of different measurement stations, multiple manufacturing lines, multiple manufacturing locations, equipment precision, calibration trueness, equipment cleanliness, etc.

The preconnected analyte sensor system limits error caused by the physical connection of the analyte sensor to the electronics portion of the sensor, and where the electronics portion includes measurement electronics, allows measurements to be taken during and after the manufacturing process. Several of the possible measurement types that can be taken by measurement electronics are sensitive to factors such as: contact resistance, leakage current, length of electrical pathways, component volume, manufacturing tolerances, material properties, etc.

The preconnected analyte sensor system limits error introduced by the measurement electronics. Measurement electronics are limited by their own manufacturing tolerances and their design limitations. Typically, calibration equipment is used to characterize a measurement electronic system. The accuracy and precision are measured and correction factors (e.g., gain, offset, linearity, temperature, resolution, etc.) are used by the circuit to compensate for absolute error. This adds cost and complexity to the manufacturing phase as testing time and programming time must be added to the process. Also, depending on the time period and the equipment used to calibrate the system, changes in various properties may arise from the time of calibration. It is therefore advantageous to calibrate the system as late in the manufacturing process as possible.

In manufacturing, having fewer steps in the process has advantages for efficiency and reducing opportunity for error. By performing a sensor calibration using the measurement electronics that will be used in the final product, calibration can be accomplished as a system. For example, to calibrate the electronics and sensor as a single step in a known calibration solution, only the value of the calibration solution must be controlled. The measurement electronics at minimum are placing a voltage bias on the sensor, measuring an analog value of current, and converting that analog value to a digital value. This digital value can be correlated to the actual value of the calibration solution. For this particular set of measurement electronics in combination with this particular sensor, the relationship between an analyte concentration in a calibration solution is now linked to a digital value that is corrected for individual measurement component variation (e.g. potentiostat variability, analog to digital converter error, leakage error, connection resistance variability, etc.). This system also eliminates manufacturing measurement electronic error from calibration equipment.

This direct-to-calibration solution type of system calibration can be performed over a broad range of analyte values, interferent materials, and other factors that affect sensor performance (e.g., low oxygen). This correlation of digital values to analyte concentration in a solution over a range can be used to build an accurate compensation model for in-vivo sensor performance.

In an alternative embodiment this process of calibration can be extended to other types of possible measurements performed by measurement electronics (e.g., impedance, capacitance, temperature, time, current, voltage, humidity, motion, etc.).

The value of a system that connects measurement electronics to an analyte sensor during manufacture can be extended beyond the calibration portion of manufacturing. This enables the system to capture data during the following system phases: manufacturing, packaging, sterilization, shipping, storage, insertion, and in vivo. Useful measurements can be taken before, during, or after one or more of the following steps: sensor connection, membrane application, curing, environmental excursions, sterilization, shipping, storage, insertion, in vivo, etc.

In transcutaneous analyte measurement systems that are currently available on the market, the sensor and measurement electronics are coupled immediately prior or during sensor insertion. This configuration prevents measurements of a coupled system during any system phase prior to the measurement electronic and analyte sensor coupling. The additional measurements that are only capable of being captured with a preconnected system can be provided to an analyte processing algorithm. These measurements can be correlated to in vivo performance, fault detection, sensor life, sensitivity shift, calibration shift, sensor performance indicator, accuracy, etc. The measurement correlations can be used to identify or compensate for system experience over an extended time period that is useful during the in vivo system phase.

For multiple measurements at different time points and system phases a multi variate model can be created. This frequency and breadth of data gathering can more accurately model system characteristics. Some of this analysis can be accomplished using measurements taken by manufacturing or calibration equipment. These input measurements may optionally be incorporated in addition to measurements taken by measurement electronics. In other embodiments the model may only include input from manufacturing and/or calibration equipment. The output measurements may be taken by manufacturing and/or calibration equipment or during the in vivo phase by reference measurements of blood analyte levels (e.g. YSI, finger stick blood glucose meters, laboratory analysis, etc.).

For example, measurements such as impedance, temperature, current measurements, time, etc. may be taken by preconnected measurement electronics during various phases of manufacture such as pre-sensor attachment, post-sensor attachment, membrane application, curing, and calibration. The preconnected system may collect spatial information such as location in a fixture, location in equipment, or an equipment identifier. This data set may be combined with an additional data set from sensors placed in manufacturing equipment that gather variables such as humidity, temperature, material viscosity, time, equipment identifier, etc. An additional data set can also be gathered that track external variables such as time, date, room temperature, room humidity, manufacturing equipment, calibration equipment, operator, manufacturing line, manufacturing location, etc.

The collated measurements can be interpreted immediately or stored for further processing at a later time. The information can be used to adjust manufacturing parameters or to build a correction factor, determine lot classification, reject sensors, or used by an analyte processing algorithm. This large amount of data can be input into tools such as machine learning algorithms to identify correlations.

The multi variable model can be used to identify and correct for relationships between input parameters and output parameters. Some of these relationships are well known (e.g. the relationship of temperature on analyte sensitivity measurements) and others have yet to be identified. Tools used to identify and model these relationships may be: linear regression additive models, generalized linear modeling optionally incorporating one or more nonlinear functions, non-parametric data fitting to empirical modeling, nonlinear regression modeling, neural network models, or other suitable models. This list is only exemplary and any suitable statistical or analysis tools can be used to model system relationships. Other suitable methods of data analysis are described in "Handbook of Chemometrics and Qualimetrics, Volume 20A" and "Handbook of Chemometrics and Qualimetrics, Volume 20B" published by Elsevier Science 1998 and incorporated by reference.

Many system measurements that can be taken have known correlations to additional system parameters. In this way it is possible to draw correlations to parameters that are not directly measured but which may be useful to input or process with an analyte algorithm processing unit. This has several advantages such as requiring less physical sensor components that add cost and complexity, gathering information that is not easily measured due to location or sensor size, providing redundancy or improved accuracy to additional sensors (e.g. compensating for temperature in a current measuring circuit).

Example applications utilizing inferred measurements may be some of the following: using temperature and sensor impedance measurements to infer humidity levels ex vivo; using one or more temperature sensors to calculate a temperature gradient; using the temperature gradient data to estimate temperature of a non-measured point such as the tip of an analyte sensor in vivo; using temperature and accelerometer data to estimate physical exertion. This is not a complete list and any of the sensed measurements can be combined with one or more other sensed measurements to estimate one or more non-sensed measurements.

By pre-connecting the sensor to some or all of the sensor electronics, the sensor can be monitored throughout all or part of its life, and most especially during the part of the sensor's life after it leaves the factory. Sensor monitoring may be advantageous for a number of reasons. In particular, it can address issues concerning variability (the divergence over time from a sensor's calibration value assigned in the factory), accuracy (the error added to the overall analyte sensor system arising from variability in the individual components that make up the system) and manufacturing processes that reduce consistency from sensor to sensor and sensor lot to sensor lot. Additionally, a preconnected sensor can facilitate data transfer from the sensor to external devices and provide improvements to sensor safety by detecting when a sensor deployed in the field is potentially unsafe.

In one aspect, variability issues are addressed by performing various active measurements that are taken post-manufacturing. For instance, in one embodiment, environmental conditions (e.g., temperature, humidity) under which the sensor and preconnected electronics are maintained while sealed in packaging during storage and prior to use may be monitored. In the case of temperature, an on-board electronics temperature sensor such as a thermistor or thermocouple may be used to measure and store temperature data. Likewise, an on-board electronics humidity sensor may be provided to monitor humidity. Alternatively, an external temperature and/or humidity sensor physically coupled to the electronics (e.g., in the base, in the package) may be used to measure and store temperature and/or humidity data. In other cases an independent temperature and/or humidity sensor that is in wireless communication with the electronics may be used. In some cases there may be an individual temperature and/or humidity sensor assigned to each analyte sensor. Alternatively, there may be a single temperature and/or or humidity sensor assigned to each box/shipper/pallet of analyte sensors. In another implementation the analyte sensor wire itself may be used to determine temperature and/or humidity by inference via impedance or current measurements, which measurements may be stored in the preconnected electronics.

In some embodiments another environmental condition that may be monitored is the radiation dose that is imparted to the sensor for sterilization purposes after the sensor and any preconnected electronics have been sealed in packaging. In one example a sterilization detector may be provided on the electronics so that the detector is able to quantify the dose amount using the active electronics. In some cases material may be added to the packaging that is sensitive to the sterilization dose and which can be electronically interrogated by the electronics post-sterilization to determine sensor characteristics such as impedance, resistance and/or capacitance. From this it may be possible to infer the orientation of the device in the packaging during sterilization. Bulk detection of the sterilization dose may also be obtained for each box/shipper/pallet of analyte sensors. The dosage that is measured may be used to assign a value to the analyte sensor via wireless communication with the preconnected electronics, the value for later use in deriving subsequent calibration parameters.

In an additional aspect, another environmental condition that may be monitored is movement of the analyte sensor using an accelerometer, a triggering break fuse or other motion sensor. In this way vibrations or impact due to dropping or the like may be detected, which can cause damage to the sensor membrane or applicator mechanism.

Yet other environmental conditions that may be monitored include ambient gas exposure and the duration of time that has elapsed since sensor manufacture.

In addition to or instead of the active monitoring techniques discussed above to address variability issues, passive techniques may also be used. For instance, in one implementation, described in U.S. Application No. 62/521,969, filed Jun. 19, 2017, entitled "Applicators for Applying Transcutaneous Analyte Sensors and Associated Methods of Manufacture, the packaging material that is used may provide a humidity barrier that can maintain the moisture vapor transmission rate below some threshold level, e.g., less than 10 grams/100 in$^2$/day or less than 1 grams/100 in$^2$/day. Examples of packaging material that may be used include metallic foil (e.g. aluminum, titanium), a metallic substrate, aluminum oxide coated polymer, silicon dioxide coated polymer, a polymer substrate coated with a metal applied via vapor metallization, or low MVTR polymers (e.g. PET, HDPE, PVC, PP, PLA).

Yet another passive technique that may be used to monitor environmental conditions, includes the provision of a visual indicator material in the packaging which changes color or visibility with exposure to temperature and/or humidity over time. Alternatively, instead of a visual indicator, the indicator may undergo a dimensional change in length or position in response to temperature or humidity changes.

In some embodiments that employ humidity and/or temperature monitoring in the packaging, if either or both such monitors determine that the environmental conditions have, at some point, for some duration, exceeded acceptable limits, the packaging may be provided with a mechanism to physically prevent the sensor in that packaging from being used. For instance, a material that changes in dimensions with temperature and/or humidity such as a bimetal (similar to those used in thermostats), metal, or polymer may be used in combination with an interlocking feature in the applicator to physically (either permanently or temporarily) prevent the applicator from deploying, preventing the packaging from being opened, and/or preventing a button or the like from being activated. The physical change in the material dimensions will automatically enable this feature when the predetermined environmental conditions are exceeded.

In another aspect, system level compensation may be achieved which allows for greater parameter variability among individual system components while reducing overall error. This may be accomplished using the data stored in the preconnected electronics concerning the monitored environmental conditions as input to an algorithm that is used to adjust the sensor calibration model. The adjustments may be made to the initial and/or final sensor sensitivity, the background signal and/or the equilibration rate. In some cases, the data that is gathered and stored for an individual sensor or a sensor lot may be tailored to an individual patient. Moreover, the adjustments that are needed may also use as an additional input information that has been previously obtained over time for large numbers of sensors and patients to calculate calibration compensation values based on the performance of sensors that had experienced similar conditions.

The algorithm that is used to adjust the sensor calibration model may also include a time component that uses data obtained by examining the sensitivity profile and background signal profile of the sensor over the time from insertion (when the factory calibrated initial sensitivity and background signal is used) to the transition to a stable final sensitivity and background signal. The sensor calibration model may be compensated based on the difference between the factory calibration value and the rate of change during the sensitivity transition period. Typical break-in curves can be obtained for sensors from this data as well as changes to the curves arising from changes induced by sterilization, temperature, humidity and/or storage time. These break-in curves may be used to compensate the sensor calibration model for deviations from the factory calibration.

In another aspect, the sensor calibration model that is updated based on the data stored in the preconnected electronics concerning the monitored environmental conditions may be used to make adjustments to the sensor calibration value prior to insertion of the analyte sensor in the patient. For example, the voltage bias applied to the analyte sensor may be adjusted based on the stored data. In some cases the voltage bias may be applied while the analyte sensor is in its packaging to change the sensor properties in order to, for example, have the sensor undergo break-in while in the packaging. In addition, the packaging may contain a calibration solution that may be embedded in a foam, gel, etc., to prevent spillage. The calibration solution can be released shortly before the package is opened or while the package is being opened to facilitate calibration of the sensor in the package. In yet another aspect, the estimated break-in time that the sensor needs prior to start up may be adjusted based on the stored data, including the age of sensor and its measured impedance. The break-in time estimated in this manner may be displayed on the display of the system.

In another aspect the stored data may be used in conjunction with measurements obtained in vivo to adjust for sensitivity shifts that arise in vivo. For instance, the impedance may be measured in vivo in response to a stimulus signal, which may be a pulse, single frequency, multiple frequency, or spectroscopy (EIS) signal. The measured impedance shift can be correlated to changes in sensitivity, but the correlation may be made more complex by changes in temperature and ionic concentration (such as sodium) in the surrounding fluid. To address this issue, impedance measurements can be taken at one or more temperatures in the factory and changes in temperature can be mapped to shifts in the impedance measurement. This information can then be used in vivo by taking a temperature measurement in vivo and making any adjustments to the relationship between the measured impedance shift and changes in sensitivity. Likewise, impedance measurements can be taken at one or more ionic concentrations in the factory and changes in concentration can be mapped to shifts in the impedance measurement. This information can then be used in vivo by taking an ionic concentration measurement in vivo and making any adjustments to the relationship between the measured impedance shift and changes in sensitivity. The ionic concentration may be measured using a secondary electrode circuit that may be located on the same body as the analyte measurement circuit or on another subcutaneous sensor body. In some cases the ionic concentration may be obtained by optical measurements via changes to the refractive index of the fluid. The light source for such optical measurements may be ambient light or a dedicated light source that exposes the fluid to light of a known wavelength.

The accuracy of a preconnected sensor depends in part on the error added to the system in the factory by combining components with individual variability. Such errors that can impact the system level calibration may arise from the sensor sensitivity (e.g., the slope, baseline and $O_2$), membrane defects (e.g., impedance detection), electronics (e.g., voltage bias accuracy, current measurement linearity, leakage current), the calibration process (e.g., solution accuracy, measurement equipment accuracy) and the interconnect coupling the analyte sensor and the electronics (e.g., the resistance value and variations between the analyte sensor and measurement electronics, and between the analyte sensor and the calibration electronics).

In another aspect, pre-connecting the analyte sensor and the various components of the electronics may give rise to manufacturing improvements. For instance, such a pre-connection can allow for improved sensor tracking and serialization by providing a component attached to the sensor that has a surface on which a code (e.g. barcode, label, etc.) can be located for use in identification. The code, which may serve as a unique identifier, may be applied during or before manufacturing. The code may also include sensor data such as a calibration code, sensitivity value, etc., which are obtained during manufacturing. In some cases wireless communication may be established with the pre-connected sensor during the manufacturing process. For example, the sensors can be identified and tracked via wireless interrogation using short-range wireless communication protocols such as RFID, NFC and Bluetooth. Likewise, the analyte sensor can actively broadcast data or its identifier using a short range wireless communication protocol. In this way the handling efficiency of the analyte sensor during manufacturing can be improved as the sensors are moved, connected and disconnected multiple times. The body of the preconnected electronics can also serve as an anchoring body for connection and alignment that may improve the manufacturing flow. Further improvements can arise from replacing physical electrical connections with non-contact wireless methods.

In another aspect, the calibration code affixed to the sensor, transmitter, packaging or other component may be a dynamic calibration code that changes with changes in environmental conditions. For example, portions of a printed code (e.g., a barcode) may be obscured by environmentally reactive pigments such as a thermochromatic dye, which cause the value of the code to change. In the shipping industry, reactive pigments are employed which turn black (or some other color), or which turn from transparent to black based on exposure to heat, cold, humidity or shock (by being dropped, for example). Thus, if a calibration code were printed on the packaging, for instance, it could contain a base calibration code which adjusts the calibration curve for a sensor. Additional digits may be printed such that they either disappear or appear when exposed to an environmental factor that impacts calibration.

For instance, in an example of a dynamic calibration code in the form of a barcode, a predetermined digit, say "3," may indicate heat exposure. If in this example the package is exposed to heat over a threshold value the digit 3 disappears, as does its corresponding portion of the barcode. Another digit, say "7," may indicate that humidity exposure is at a threshold. If the humidity surpasses the threshold the digit 7 appears, as does its corresponding portion of the barcode. When scanned, or otherwise entered into the software within a patient's mobile device or other receiver, a calibration curve offset or adjustment can be generated. Additionally, this information may be transmitted back to the manufacturer to determine lot variability as well as variability during shipping, thereby identifying poorly stored sensors. This information may also flow back to accounting for inventory write down as well. Additional reactive pigments may include a "cut off" threshold which are located on the periphery of the code and which would appear or disappear if the sensor was exposed to something which renders it unusable. This same information may be used to accrue an end user credit and reshipment as well as the aforementioned accounting write down.

In another aspect, pre-connecting the analyte sensor and the various components of the electronics may allow manufacturing improvements by using closed loop manufacturing feedback, which can allow manufacturing variables to be monitored in real time to modify the manufacturing process to improve the resulting sensors. The sensors can be in the form of a brick, fixture, or individual sensors. Variables that can be monitored include, by way of illustration, temperature, humidity, the content (e.g., PVP, ethanol, etc.) of the particular coating solution in which the sensor is dipped (which may be determined from the refractive index of the solution), the duration of the dip, the number of times the sensors are dipped in the solution, and the duration, temperature and humidity of the curing process. The data gathered during this monitoring process may allow large sensor data sets concerning the manufacturing process to be obtained, which can be used to create outcome-based predictors. For instance, if as a result of this process it is determined that at some point during the manufacturing process the temperature was higher than its mean value, the humidity was lower than its mean value and the sensor sensitivity was higher than its mean value, an update to the manufacturing process may be implemented based on this insight to reduce deviations in the sensor sensitivity from the mean value. Moreover, since the processes can be continuously monitored, it can be determined if the updates to the manufacturing process actually improve the outcome.

In addition to using data gathered about individual sensors as feedback during the manufacturing process, sensor lot information may be obtained and stored. In this way additional information may be obtained that can be used as feedback during the manufacturing process. For instance, long term testing for shifts in e.g., the sensitivity, of sensor lots may be stored in the cloud for use in a suitable algorithm. Likewise, information concerning the sensor shipping process (geographic information, means of transportation used, duration of shipping process, etc.) may be obtained and stored so that it can be subsequently correlated with sensor data to determine the effects of environmental exposure.

In another aspect, in addition to using data gathered during manufacturing as part of a closed loop feedback process, data concerning the sensor and the patient while the sensor is in vivo may also be used. For instance, analytics from individual sensor performance in a patient may be used as input data into any number of algorithms used during the manufacturing process. Such data may be obtained from devices such as a mobile phone or other receiver that are in communication with the sensor while in use. The data that is obtained may be any available information such as temperature, humidity, sensor motion (which may indicate, for instance, that the patient is sleeping, exercising, etc.), compressional forces that can be determined from an accelerometer and which may be exerted on the sensor while the user is in different positions (e.g., sitting, standing, laying down) and patient proximity to known locations (e.g., Wi-Fi beacons, cell towers, internet-of-things (TOT) devices).

In another aspect, the stored data obtained from the sensor during and after manufacturing can be used to reduce the risk of potentially unsafe sensors being deployed in the field. Such data may be used to examine the efficacy of various storage conditions (e.g., packaging barriers and packaging indictors) and sterilization conditions (by, e.g., sampling sensor lots that undergo sterilization) and to better determine when a sensor is expected to expire based on its age and the available data concerning the manufacturing, storage and other environmental conditions experienced by the sensor.

In this way the patient can be automatically notified (by e.g., an app pop-up, email, automated phone call) when a sensor is expected to expire.

In a first aspect, a method is provided for self-calibration of an analyte sensor system that includes an analyte sensor operatively coupled to sensor electronics, comprising: applying a bias voltage with the sensor electronics to the analyte sensor to generate sensor data, the analyte sensor system having an initial characteristic metric determined at a first time; using the sensor electronics at a second time subsequent to the first time to determine a change to the initial characteristic sensitivity metric of the analyte sensor system based at least in part on one or more manufacturing and/or environmental parameters; and using the sensor electronics to automatically calibrate, without user intervention, the analyte sensor system based at least in part on the determined change to the initial characteristic metric.

In an embodiment of the first aspect or any other embodiment thereof, one or more environmental parameters are monitored between the first time and second time.

In an embodiment of the first aspect or any other embodiment monitoring the one or more environmental parameters includes measuring an impedance of the analyte sensor by: applying a stimulus signal to the analyte sensor; measuring a signal response to the stimulus signal; calculating the impedance based on the signal response; and determining a value for the environmental parameter based on an established relationship between the impedance and the environmental parameter.

In an embodiment of the first aspect or any other embodiment thereof, the first time is subsequent to sensor fabrication and the second time is prior to sensor use in vivo.

In an embodiment of the first aspect or any other embodiment thereof, the first time is subsequent to sensor fabrication and the second time is subsequent to initiation of sensor use in vivo.

In an embodiment of the first aspect or any other embodiment thereof, the initial characteristic metric is determined by initially calibrating the analyte sensor while the analyte sensor is operatively coupled to a sensor interface that is configured to provide an electrical communication interface between the analyte sensor and each of a manufacturing station and the sensor electronics.

In an embodiment of the first aspect or any other embodiment thereof, the initial characteristic metric is further determined by measuring an in vitro sensitivity characteristics of the analyte sensor.

In an embodiment of the first aspect or any other embodiment thereof, the initial characteristic metric is determined by initially calibrating the analyte sensor while the analyte sensor is operatively coupled to one or more components of the sensor electronics.

In an embodiment of the first aspect or any other embodiment thereof, the one or more components includes a potentiostat.

In an embodiment of the first aspect or any other embodiment thereof, the analyte sensor is continuously operatively coupled to the one or more components of the sensor electronics between the first and second times without interruption.

In an embodiment of the first aspect or any other embodiment thereof, the first time is during a first portion of a manufacturing life phase of the analyte sensor and the second time is during a second portion of the manufacturing life phase that is subsequent to packaging the analyte sensor and the one or more components of the sensor electronics in the sterile package.

In an embodiment of the first aspect or any other embodiment thereof, the first time is during a manufacturing life phase of the analyte sensor and the second time is during sensor use in vivo.

In an embodiment of the first aspect or any other embodiment thereof, monitoring the one or more environmental parameters includes monitoring a temperature of the analyte sensor while in a sterile package.

In an embodiment of the first aspect or any other embodiment thereof, monitoring the temperature includes measuring an impedance of the analyte sensor by: applying a stimulus signal to the analyte sensor; measuring a signal response to the stimulus signal; calculating the impedance based on the signal response; determining a value for the temperature based on an established relationship between the impedance and the temperature.

In an embodiment of the first aspect or any other embodiment thereof, monitoring the temperature includes measuring the temperature using a temperature sensor included in the sterile package, the temperature sensor being operatively couplable to the sensor electronics.

In an embodiment of the first aspect or any other embodiment thereof, monitoring the one or more environmental parameters includes monitoring a humidity of the analyte sensor environment while in a sterile package.

In an embodiment of the first aspect or any other embodiment thereof, monitoring the humidity includes measuring an impedance of the analyte sensor by: applying a stimulus signal to the analyte sensor; measuring a signal response to the stimulus signal; calculating the impedance based on the signal response; determining a value for the humidity based on an established relationship between the impedance and the humidity.

In an embodiment of the first aspect or any other embodiment thereof, monitoring the humidity includes measuring the humidity using a humidity sensor included in the sterile package, the humidity sensor being operatively couplable to the sensor electronics.

In an embodiment of the first aspect or any other embodiment thereof, monitoring the one or more environmental parameters includes monitoring a sterilization dosage used to sterilize the analyte sensor.

In an embodiment of the first aspect or any other embodiment thereof, determining the change to the initial characteristic metric includes determining the change through use of a mathematical function.

In an embodiment of the first aspect or any other embodiment thereof, the manufacturing parameters are obtained from an identifier of the analyte sensor.

In an embodiment of the first aspect or any other embodiment thereof, the identifier is affixed to the analyte sensor.

In an embodiment of the first aspect or any other embodiment thereof, the identifier is obtained by wirelessly interrogating the analyte sensor.

In an embodiment of the first aspect or any other embodiment thereof, the identifier is associated with a manufacturing lot from which the analyte sensor was obtained.

In an embodiment of the first aspect or any other embodiment thereof, a user is selected to receive the analyte sensor system based at least in part on one or more analyte sensor characteristics.

In an embodiment of the first aspect or any other embodiment thereof the one or more sensor characteristics includes an updated characteristic metric that is derived from the determined change to the initial characteristic metric.

In an embodiment of the first aspect or any other embodiment thereof, values for the monitored environmental parameters are stored for subsequent use when automatically calibrating the analyte sensor system.

In an embodiment of the first aspect or any other embodiment thereof, monitoring the temperature of the analyte sensor while in the sterile package includes determining if the temperature exceeds or falls below pre-established threshold values.

In an embodiment of the first aspect or any other embodiment thereof monitoring the temperature of the analyte sensor while in the sterile package includes determining if the humidity exceeds or falls below pre-established threshold values.

In an embodiment of the first aspect or any other embodiment thereof, the initial characteristic metric is reflective of an initial sensor sensitivity.

In an embodiment of the first aspect or any other embodiment thereof, the initial characteristic metric is reflective of an initial sensor sensitivity and baseline value.

In an embodiment of the first aspect or any other embodiment thereof, the initial characteristic metric is reflective of an initial sensor sensitivity profile.

In an embodiment of the first aspect or any other embodiment thereof, an initial calibration factor is derived from the sensor characteristic metric.

In an embodiment of the first aspect or any other embodiment thereof, the change to the initial sensor characteristic is indicative of sensor failure.

In an embodiment of the first aspect or any other embodiment thereof, the one or more manufacturing parameters are measured prior to the second time.

In an embodiment of the first aspect or any other embodiment thereof, the one or more manufacturing parameters are measured prior to the first time.

In a second aspect, a method is provided for self-calibration of an analyte sensor system that includes an analyte sensor operatively coupled to sensor electronics, comprising: applying a bias voltage with the sensor electronics to the analyte sensor to generate sensor data, the analyte sensor system having an initial characteristic metric determined at a first time when the analyte sensor is operatively connected to one or more components of the sensor electronics; using the sensor electronics at a second time subsequent to the first time to determine a change to the initial characteristic metric of the analyte sensor system based at least in part on one or more manufacturing and/or environmental parameters, wherein the second time is before or during sensor use in vivo; and using the sensor electronics to automatically calibrate, without user intervention, the analyte sensor system based at least in part on the determined change to the initial characteristic metric.

In a third aspect, a method is provided for self-calibrating an analyte sensor system that includes an analyte sensor operatively coupled to sensor electronics, comprising: applying a bias voltage with the sensor electronics to the analyte sensor to generate sensor data, the analyte sensor system having an initial calibration factor that is used to convert sensor data to analyte concentration values; using the sensor electronics to update the calibration factor of the analyte sensor system at a plurality of times during one or more life phases of the analyte sensor based at least in part on one or more manufacturing and/or environmental parameters that are monitored during one or more life phases; and using the sensor electronics to automatically calibrate, without user intervention, the analyte sensor system based at least in part on the updated calibration factor.

In an embodiment of the third aspect or any other embodiment thereof, the one or more life phases include a plurality of life phases.

In an embodiment of the third aspect or any other embodiment thereof, the plurality of life phases includes manufacturing, shipping, storage, insertion and use phases.

In an embodiment of the third aspect or any other embodiment thereof, using the sensor electronics to update the calibration factor of the analyte sensor system includes determining a complex adaptive calibration value that is based at least in part on manufacturing conditions and environmental conditions experienced by the analyte sensor during a plurality of the life phases of the analyte sensor.

In an embodiment of the third aspect or any other embodiment thereof, the manufacturing parameters include process and/or design parameters.

In an embodiment of the third aspect or any other embodiment thereof, the manufacturing parameters include process parameters, the process parameters including temperature, humidity, curing, time and dip time.

In an embodiment of the third aspect or any other embodiment thereof, the manufacturing parameters include design parameters, the design parameters including analyte sensor membrane thickness and raw material characteristics.

In an embodiment of the third aspect or any other embodiment thereof, the sensor electronics is used to receive remotely stored sensor performance data to update the calibration factor.

In an embodiment of the third aspect or any other embodiment thereof, the remotely stored sensor performance data that is received concerns analyte sensors that have experienced or been exposed to manufacturing and/or environmental parameters that are most similar to one or more of the monitored manufacturing and/or environmental parameters.

In a fourth aspect, a method is provided in which the sensor experiences a plurality of life phases including manufacture, shipping, storage and insertion and use in a user as part of a sensor session, comprising: disposing measurement electronics in operable connection to the sensor; during the manufacture life phase in a factory, the manufacture life phase manufacturing a sensor using a plurality of manufacturing parameters, determining a first calibration factor; during the shipping or storage phases, determining a second calibration factor; and upon insertion in a user, using a combination calibration factor in a user monitoring device to calibrate signals from the sensor, wherein the combination calibration factor is based on both the first calibration factor and the second calibration factor.

In an embodiment of the fourth aspect or any other embodiment thereof, the first calibration factor is stored in the sensor electronics or in measurement electronics associated with the sensor assembly.

In an embodiment of the fourth aspect or any other embodiment thereof, the measurement electronics form a part of the sensor electronics.

In an embodiment of the fourth aspect or any other embodiment thereof, the measurement electronics are separate from the sensor electronics.

In an embodiment of the fourth aspect or any other embodiment thereof, the measurement electronics is disposed in the same package as the sensor electronics.

In an embodiment of the fourth aspect or any other embodiment thereof, the measurement electronics is disposed in a different package than the sensor electronics.

In an embodiment of the fourth aspect or any other embodiment thereof, the sensor assembly and the measurement electronics are disposed in a package for shipping.

In an embodiment of the fourth aspect or any other embodiment thereof, the user monitoring device is a dedicated receiver or a smart phone.

In an embodiment of the fourth aspect or any other embodiment thereof, the transmitting is from the sensor electronics or the measurement electronics to the dedicated receiver or the smart phone.

In an embodiment of the fourth aspect or any other embodiment thereof, the second calibration factor is stored within the measurement electronics or the sensor electronics.

In an embodiment of the fourth aspect or any other embodiment thereof, the combination calibration factor is transmitted to a cloud server.

In an embodiment of the fourth aspect or any other embodiment thereof, the combination calibration factor, or the second calibration factor, or both, are transmitted to the factory, to cause a change in one of the plurality of manufacturing parameters.

In an embodiment of the fourth aspect or any other embodiment thereof, measuring a second calibration factor is performed by the measurement electronics.

In an embodiment of the fourth aspect or any other embodiment thereof, the first calibration factor is a system level calibration factor pertaining to the calibration of all of the components in the sensor assembly.

In an embodiment of the fourth aspect or any other embodiment thereof, the transmitting further comprises transmitting a sensor tracking number or serial number to a cloud server or to the factory along with the combination calibration factor, whereby a lot associated with the sensor can be identified.

In an embodiment of the fourth aspect or any other embodiment thereof, the measurement electronics are configured to detect faults in the sensor electronics or sensor.

In an embodiment of the fourth aspect or any other embodiment thereof, the transmitting further comprises transmitting data about detected faults in the sensor electronics or sensor.

In an embodiment of the fourth aspect or any other embodiment thereof, a calibration factor stored in the user monitoring device is modified to compensate for the detected fault.

In an embodiment of the fourth aspect or any other embodiment thereof, the measurement electronics are configured to detect electrical signals from the sensor wire, the sensor electronics, the housing, or a combination.

In an embodiment of the fourth aspect or any other embodiment thereof, the combination calibration factor is configured to correct for individual process and shipping/storage variations of an in vivo sensor.

In an embodiment of the fourth aspect or any other embodiment thereof, the first calibration factor or the second calibration factor, or both, are indicative of a measured impedance.

In an embodiment of the fourth aspect or any other embodiment thereof, the impedance measurement is performed by measuring a step response at a single frequency or at multiple frequencies.

In an embodiment of the fourth aspect or any other embodiment thereof, a third calibration factor is measured prior to shipping, and wherein the third calibration factor is indicative of impedance.

In an embodiment of the fourth aspect or any other embodiment thereof, the first calibration factor or the second calibration factor, or both, are indicative of a measured temperature.

In an embodiment of the fourth aspect or any other embodiment thereof, the first calibration factor or the second calibration factor, or both, are indicative of a measured humidity.

In an embodiment of the fourth aspect or any other embodiment thereof, the combination calibration factor is used to calculate a modified calibration value, detect physical damage to the sensor, or detect exposure of the sensor assembly to temperature and/or humidity.

In an embodiment of the fourth aspect or any other embodiment thereof, the combination calibration factor is a complex adaptive value that combines calibration values collected during sensor manufacturer and conditions experienced during the time from sensor manufacturer to sensor insertion.

In an embodiment of the fourth aspect or any other embodiment thereof, a user is selected to receive the sensor based on the first calibration factor, whereby population data or individual user data determines that the sensor with the first calibration factor is optimized for the user.

In an embodiment of the fourth aspect or any other embodiment thereof, the user is known to have a high average glucose level, and wherein the first calibration factor is a relatively low sensitivity.

In an embodiment of the fourth aspect or any other embodiment thereof, the manufacturing life phase includes a packaging phase in which the preconnected sensor assembly is packaged in a sterile package, the first calibration factor being determined after the preconnected sensor assembly is packaged in the sterile package.

In a fifth aspect, an improved method is provided of calibrating a sensor associated with a preconnected sensor assembly in which the sensor experiences a plurality of life phases including manufacture, shipping, storage and insertion and use in a user as part of a sensor session, comprising: disposing measurement electronics in operable connection to the sensor electronics; during the manufacture life phase in a factory, the manufacture life phase manufacturing a sensor using a plurality of manufacturing parameters, determining a first calibration factor; during the shipping or storage phases, measuring a second calibration factor; and upon insertion in a user, calculating a combination calibration factor and storing the same within the sensor electronics, wherein the combination calibration factor is based on both the first calibration factor and the second calibration factor, wherein the combination calibration factor is configured to provide a conversion between a detected signal from the sensor wire and an analyte concentration in the user.

In an embodiment of the fifth aspect or any other embodiment thereof, an indication is displayed of the analyte concentration.

In an embodiment of the fifth aspect or any other embodiment thereof, the displaying occurs on a user monitoring device in signal communication with the sensor electronics.

In an embodiment of the fifth aspect or any other embodiment thereof, the user monitoring device is a dedicated receiver or a smart phone.

In a sixth aspect, an improved method is provided of manufacturing a sensor assembly including a sensor wire, a housing, and sensor electronics, comprising: pre-connecting at least a sensor wire to at least a portion of the sensor electronics sufficient to monitor manufacturing parameters; monitoring the manufacturing parameters while completing manufacturing of the sensor assembly; modifying one or more of the manufacturing parameters during subsequent manufacturing processes used to manufacture additional sensor assemblies, the modifying being based at least in part on the monitored manufacturing parameters.

In an embodiment of the sixth aspect or any other embodiment thereof, the sensor electronics is preconnected to the sensor wire but where the battery and radio remain disconnected.

In an embodiment of the sixth aspect or any other embodiment thereof, the battery is pre-connected to the sensor wire and the portion of the sensor electronics sufficient to monitor manufacturing parameters.

In an embodiment of the sixth aspect or any other embodiment thereof, the radio is preconnected to the battery and the sensor wire and the portion of the sensor electronics sufficient to monitor manufacturing parameters.

In an embodiment of the sixth aspect or any other embodiment thereof, the combined error of the preconnected sensor wire and the portion of the sensor electronics sufficient to monitor manufacturing parameters in is less than a propagated or summed error of the sensor wire and the portion of the sensor electronics sufficient to monitor manufacturing parameters considered individually.

In seventh aspect, an improved preconnected sensor assembly is provided that includes a sensor wire, a housing, and sensor electronics, where the sensor is preconnected to a housing and/or to sensor electronics, and wherein the sensor wire is at least preconnected to an interposer which is configured for allowing measurements of sensor physical properties without requiring a direct connection to the sensor wire.

In an embodiment of the seventh or any other embodiment thereof, the battery is preconnected to the sensor wire and the housing and/or sensor electronics.

In an embodiment of the seventh aspect or any other embodiment thereof, the radio is preconnected to the battery and the sensor wire and the housing and/or sensor electronics.

In an eighth aspect, a method is provided for self-calibration of an analyte sensor system that includes an analyte sensor operatively couplable to sensor electronics, comprising: operatively coupling at a first time the analyte sensor to one or more components of the sensor electronics to define a packagable analyte sensor arrangement, the packagable sensor arrangement having an initial sensitivity metric determined subsequent to the first time; applying an analyte interrogation signal with the one or more components of the sensor electronics to the analyte sensor at a second time subsequent to the first time; measuring a signal response to the stimulus signal; based at least in part on the measured signal response, determining a second sensitivity metric; automatically calibrating, without user intervention, the packagable sensor arrangement based at least in part on the initial sensitivity metric and the second sensitivity metric.

In an embodiment of the eighth aspect or any other embodiment thereof, the analyte sensor is continuously operatively coupled to the one or more components of the sensor electronics between the first and second times without interruption.

In an embodiment of the eighth aspect or any other embodiment thereof, applying an analyte interrogation signal includes applying a stimulus signal to the analyte sensor and measuring the signal response includes measuring an impedance of the packagable analyte sensor arrangement.

In an embodiment of the eighth aspect or any other embodiment thereof, automatically calibrating the packagable sensor arrangement is based on an established relationship between the impedance and analyte sensor sensitivity, wherein automatically calibrating the packagable sensor arrangement includes automatically calibrating the packagable sensor arrangement in vivo.

In a ninth aspect, a method is provided for performing an action with an analyte sensor system that includes an analyte sensor operatively coupled to sensor electronics, comprising: applying a bias voltage with the sensor electronics to the analyte sensor to generate sensor data, the analyte sensor system having an initial characteristic metric determined at a first time when the analyte sensor is operatively connected to one or more components of the sensor electronics; using the sensor electronics at a second time subsequent to the first time to determine a change to the initial characteristic metric of the analyte sensor system based at least in part on one or more manufacturing and/or environmental parameters, wherein the second time is before or during sensor use in vivo; and based at least in part on the determined change to the initial characteristic metric, performing an action selected from the group comprising: generating a message, initiating a re-calibration process, using a default calibration value and using a temperature and/or humidity compensated calibration value.

In an embodiment of the ninth aspect or any other embodiment thereof, generating the message includes generating an error message.

In an embodiment of the ninth aspect or any other embodiment thereof, generating the message includes generating a message requesting a manual recalibration.

BRIEF DESCRIPTION OF THE DRAWINGS

These and other features and advantages will be appreciated, as they become better understood by reference to the following detailed description when considered in connection with the accompanying drawings, wherein:

FIG. 17 shows a composition of an RL solution that was prepared with different Carbosil/PVP ratios.

DETAILED DESCRIPTION

Definitions

Figure 1:
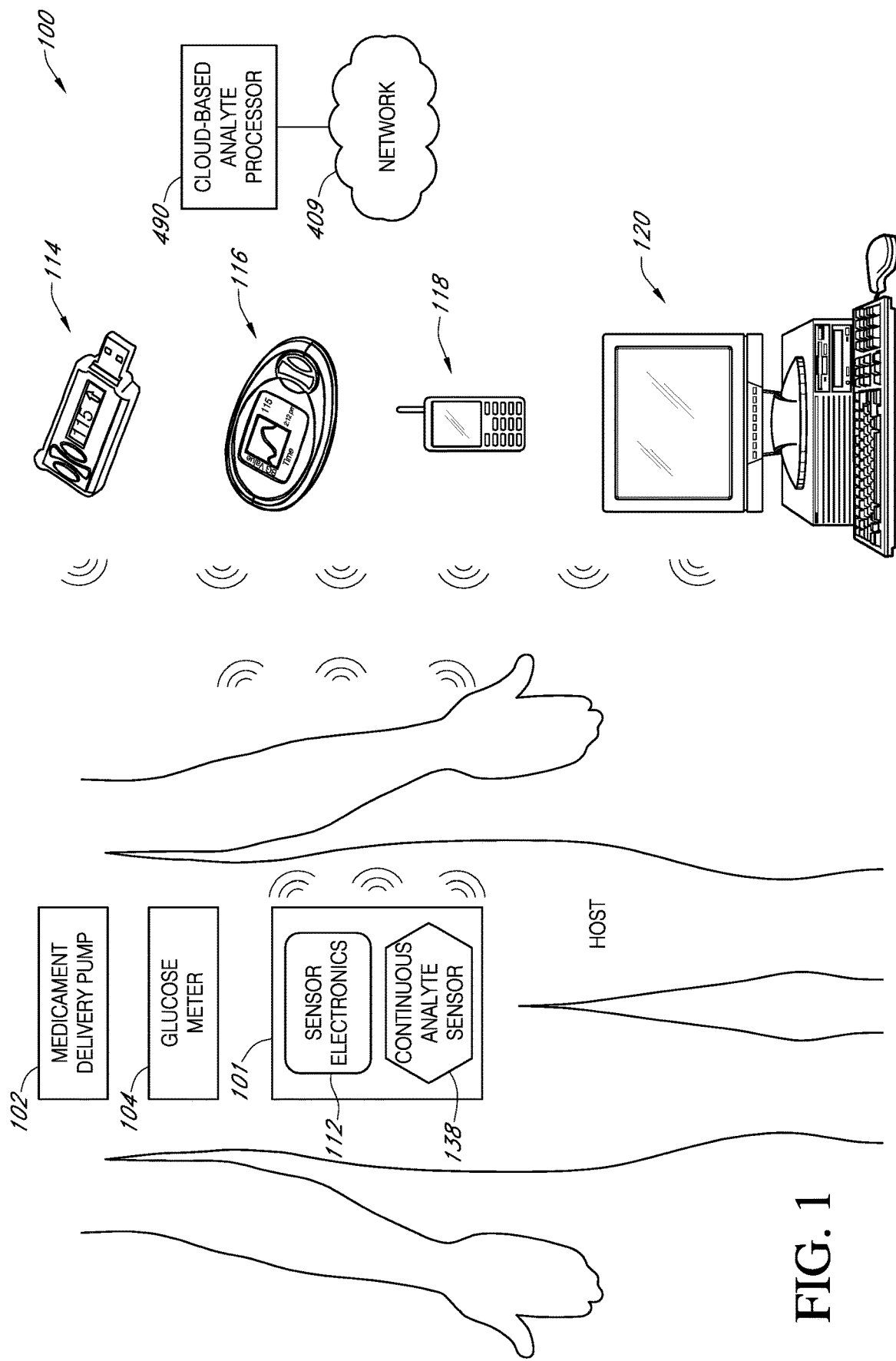
FIG. 1 is a schematic view of an analyte sensor system attached to a host and communicating with a plurality of example devices, according to some embodiments.

In order to facilitate an understanding of the embodiments described herein, a number of terms are defined below.

The term "analyte," as used herein, is a broad term, and is to be given its ordinary and customary meaning to a person of ordinary skill in the art (and is are not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-13 hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (e.g., by continuously or continually adjusting or determining the sensor's sensitivity and background), for example, at time intervals ranging from fractions of a second up to, for example, 1, 2, or 5 minutes, or longer.

The term "biological sample," as used herein, is a broad term, and is to be given its ordinary and customary meaning to a person of ordinary skill in the art (and is not to be limited to a special or customized meaning), and refers without limitation to sample derived from the body or tissue of a host, such as, for example, blood, interstitial fluid, spinal fluid, saliva, urine, tears, sweat, or other like fluids.

The term "host," as used herein, is a broad term, and is to be given its ordinary and customary meaning to a person of ordinary skill in the art (and is not to be limited to a special or customized meaning), and refers without limitation to animals, including humans.

The term "membrane system," as used herein, is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "domain," as used herein, is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electroactive surface at one location on the body and an electronic connection at another location on the body, and a membrane system affixed to the body and covering the electroactive surface.

The term "electroactive surface," as used herein, is a broad term, and is to be given its ordinary and customary meaning to a person of ordinary skill in the art (and is not to be limited to a special or customized meaning), and refers without limitation to the surface of an electrode where an electrochemical reaction takes place. In one embodiment, a working electrode measures hydrogen peroxide ($H_2O_2$) creating a measurable electronic current.

The term "baseline," as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation $y=mx+b$, the value of b represents the baseline of the signal. In certain embodiments, the value of b (i.e., the baseline) can be zero or about zero. This can be the result of a baseline-subtracting electrode or low bias potential settings, for example. As a result, for these embodiments, calibration can be defined by solving for the equation $y=mx$.

The term "inactive enzyme," as used herein, is a broad term, and is to be given its ordinary and customary meaning to a person of ordinary skill in the art (and is not to be limited to a special or customized meaning), and refers without limitation to an enzyme (e.g., glucose oxidase, GOx) that has been rendered inactive (e.g., by denaturing of the enzyme) and has substantially no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The term "non-enzymatic," as used herein is a broad term, and is to be given its ordinary and customary meaning to a person of ordinary skill in the art (and is not to be limited to a special or customized meaning), and refers without limitation to a lack of enzyme activity. In some embodiments, a "non-enzymatic" membrane portion contains no enzyme; while in other embodiments, the "non-enzymatic" membrane portion contains inactive enzyme. In some embodiments, an enzyme solution containing inactive enzyme or no enzyme is applied.

The term "substantially," as used herein, is a broad term, and is to be given its ordinary and customary meaning to a person of ordinary skill in the art (and is not to be limited to a special or customized meaning), and refers without limitation to being largely but not necessarily wholly that which is specified.

The term "about," as used herein, is a broad term, and is to be given its ordinary and customary meaning to a person of ordinary skill in the art (and is not to be limited to a special or customized meaning), and when associated with any numerical values or ranges, refers without limitation to the understanding that the amount or condition the terms modify can vary some beyond the stated amount so long as the function of the disclosure is realized.

The term "ROM," as used herein, is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM," as used herein, is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter," as used herein, is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The terms "raw data stream" and "data stream," as used herein, are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "sensor electronics," as used herein, is a broad term, and is to be given its ordinary and customary meaning to a person of ordinary skill in the art (and is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398 describe suitable electronic circuits that can be utilized with devices of certain embodiments.

The term "potentiostat," as used herein, is a broad term, and is to be given its ordinary and customary meaning to a person of ordinary skill in the art (and is not to be limited to a special or customized meaning), and refers without limitation to an electrical system that applies a potential between the working and reference electrodes of a two- or three-electrode cell at a preset value and measures the current flow through the working electrode. The potentiostat forces whatever current is necessary to flow between the working and counter electrodes to keep the desired potential, as long as the needed cell voltage and current do not exceed the compliance limits of the potentiostat.

The term "operably connected," as used herein, is a broad term, and is to be given its ordinary and customary meaning to a person of ordinary skill in the art (and is not to be limited to a special or customized meaning), and refers without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "filtering," as used herein, is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "algorithm," as used herein, is a broad term, and is to be given its ordinary and customary meaning to a person of ordinary skill in the art (and is not to be limited to a special or customized meaning), and refers without limitation to the computational processes (for example, programs) involved in transforming information from one state to another, for example using computer processing.

The term "calibration," as used herein, is a broad term, and is to be given its ordinary and customary meaning to a person of ordinary skill in the art (and is not to be limited to a special or customized meaning), and refers without limitation to the process of determining the graduation of a sensor giving quantitative measurements (e.g., analyte concentration). As an example, calibration may be updated or recalibrated over time to account for changes associated with the sensor, such as changes in sensor sensitivity and sensor background. In addition, calibration of the sensor can involve, automatic, self-calibration, e.g., without using reference analyte values after point of use.

The terms "sensor data," as used herein, is a broad term, and is to be given its ordinary and customary meaning to a person of ordinary skill in the art (and is not to be limited to a special or customized meaning), and refers without limitation to data received from a continuous analyte sensor, including one or more time-spaced sensor data points.

The terms "reference analyte values" and "reference data," as used herein, are broad terms, and are to be given their ordinary and customary meaning to a person of ordinary skill in the art (and are not to be limited to a special or customized meaning), and refer without limitation to reference data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or a YSI (Yellow Springs Instruments) test, for example.

The terms "interferents" and "interfering species," as used herein, are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured, producing a false positive signal.

The term "sensor session," as used herein, is a broad term, and is to be given its ordinary and customary meaning to a person of ordinary skill in the art (and is not to be limited to a special or customized meaning), and refers without limitation to the period of time the sensor is applied to (e.g. implanted in) the host or is being used to obtain sensor values. For example, in some embodiments, a sensor session extends from the time of sensor implantation (e.g. including insertion of the sensor into subcutaneous tissue and placing the sensor into fluid communication with a host's circulatory system) to the time when the sensor is removed.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., $H_2O_2$) associated with the measured analyte (e.g., glucose). For example, in one embodiment, a sensor has a sensitivity of from about 1 to about 300 picoAmps of current for every 1 mg/dL of glucose analyte.

The term "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

The term "process set point," as used herein, is broad term, and is to be given its ordinary and customary meaning to a person of ordinary skill in the art (and is not to be limited to a special or customized meaning), and refers without limitation to a desired or target value for a variable or process value of a system.

The term "process variability" as used herein, is a broad term, and is to be given its ordinary and customary meaning to a person of ordinary skill in the art (and is not to be limited to a special or customized meaning), and refers without limitation to a measure of the deviation from a set point and is usually expressed as a standard deviation.

The term "Monte Carlo Simulation," as used herein, is a broad term, and is to be given its ordinary and customary meaning to a person of ordinary skill in the art (and is not to be limited to a special or customized meaning), and refers without limitation to defining a domain of possible inputs, generating inputs randomly from a probability distribution over the domain, performing a deterministic computation on the inputs and aggregating the results. Monte Carlo simulations sample from a probability distribution for each variable to produce hundreds or thousands of possible outcomes. The results are analyzed to get probabilities of different outcomes occurring.

The term "accuracy," as used herein, is a broad term, and is to be given its ordinary and customary meaning to a person of ordinary skill in the art (and is not to be limited to a special or customized meaning), and refers without limitation to the closeness of a measured value to a standard or known value.

The term "precision," as used herein, is a broad term, and is to be given its ordinary and customary meaning to a person of ordinary skill in the art (and is not to be limited to a special or customized meaning), and refers without limitation to the degree to which repeated measurements under unchanged conditions show the same results.

Overview

Commercially available transcutaneous analyte measurement systems consist of discrete modules that are physically interconnected immediately prior or just following final sensor placement. Generally, the analyte sensor module is characterized by a variety of measurement factors (e.g. analyte sensitivity, baseline, impedance, capacitance, temperature, time, humidity, interferent sensitivity, etc.) These characteristics have historically been quantified once at the completion of the analyte sensor manufacturing process using manufacturing test equipment. These measurements are taken on the sensor subsystem using test configurations such as placing the analyte sensor in one or more solutions of known analyte concentration.

The measurements derived from the manufacturing process on the analyte sensor are sometimes used to create one or more metrics of the sensor performance. These metrics can be transferred using various methods (e.g. calibration code, wireless transfer, lot matching) to an analyte algorithm processing unit. In other embodiments the measurements are used to determine if an individual sensor or lot of sensors meets acceptable quality criteria. Analyte sensor metrics, in-vivo calibrations, environmental condition sensors, and a priori information are typical inputs to an analyte algorithm processing unit.

Conventional in vivo continuous analyte sensing technology has typically relied on reference measurements performed during a sensor session for calibration of the continuous analyte sensor. The reference measurements are matched with substantially time corresponding sensor data to create matched data pairs. Regression is then performed on the matched data pairs (e.g., by using least squares regression) to generate a conversion function that defines a relationship between a sensor signal and an estimated glucose concentration.

In critical care settings, calibration of continuous analyte sensors is often performed by using, as reference, a calibration solution with a known concentration of the analyte. This calibration procedure can be cumbersome, as a calibration bag, separate from (and an addition to) an IV (intravenous) bag, is typically used. In the ambulatory setting, calibration of continuous analyte sensors has traditionally been performed by capillary blood glucose measurements (e.g., a finger stick glucose test), through which reference data is obtained and input into the continuous analyte sensor system. This calibration procedure typically involves frequent finger stick measurements, which can be inconvenient and painful.

Heretofore, systems and methods for in vitro calibration of a continuous analyte sensor by the manufacturer (e.g., factory calibration), without reliance on periodic recalibration, have for the most part been inadequate with respect to high levels of sensor accuracy. Part of this can be attributed to changes in sensor properties (e.g., sensor sensitivity) that can occur during sensor use. Thus, calibration of continuous analyte sensors has typically involved periodic inputs of reference data, whether they are associated with a calibration solution or with a finger stick measurement. As noted, such can be very burdensome to the patient no matter the setting.

Described herein are continuous analyte sensors that are factory calibrated or are capable of continuous, automatic self-calibration during a sensor session and capable of achieving high levels of accuracy, without (or with reduced) reliance on reference data from a reference analyte monitor (e.g., from a blood glucose meter). Factory calibration refers generally to an initial calibration that is typically performed before the sensor leaves the factory and which is not changed over time. Automatic self-calibration, on the other hand, refers to a process in which the calibration is updated without user intervention at one or more intervals of time subsequent to factory calibration, where the updating is based on information obtained during manufacturing and/or during later life phases of the analyte sensor. The updating of the calibration is generally accomplished by sending a signal from e.g., the cloud, to the sensor or the sensor electronics.

Figure 20:
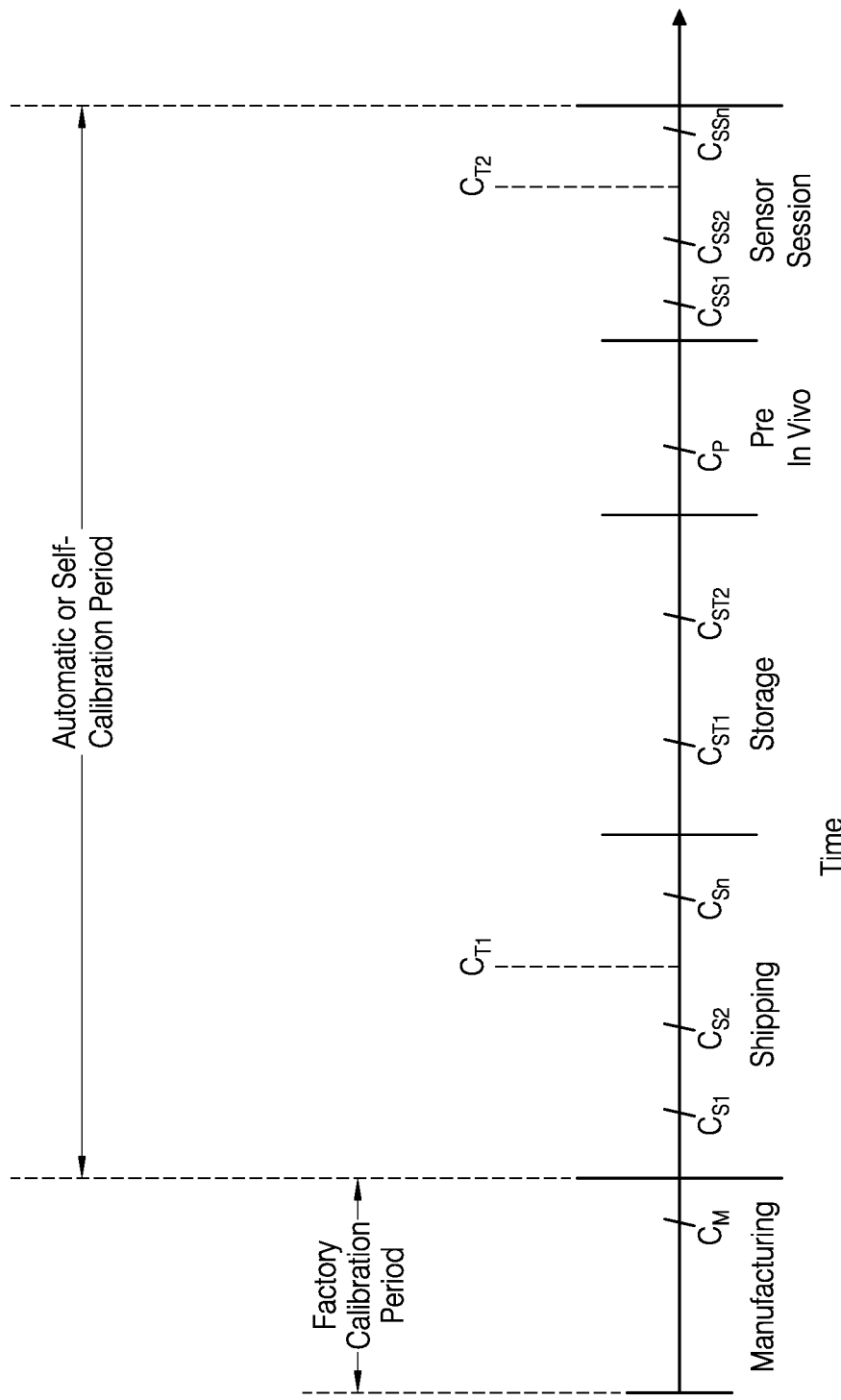
FIG. 20 shows an example of various life phases that an analyte sensor may undergo.

FIG. 20 shows an example of various life phases that an analyte sensor may undergo, which illustratively include a sensor manufacturing phase, a sensor packaging phase, a sensor storage phase, a pre in vivo phase, and a sensor session phase. As will be discussed in more detail below, in some cases the sensor may undergo additional, or fewer, life phases as well. At various times t during these phases a complex adaptive calibration factor $C(t, p_i)$ may be generated that is a function of the time t since the sensor was manufactured and various parameters $p_i$, where $i \geq 1$. The parameters $p_i$ represent, for instance, environmental conditions experienced by the analyte sensor (and any preconnected electronics, if present) from sensor manufacture to sensor use during the sensor session phase, possibly combined with additional information such as patient-specific data. The complex adaptive calibration factor may reflect changes to the analyte sensor (and any preconnected electronics, if present) that have arisen since one or more initial calibration factors $C_m$ were obtained during sensor manufacture. For instance, in FIG. 20 an initial calibration factor $C_M$ is obtained by a "cal check" procedure in the factory during which the sensor undergoes in vitro calibration. At subsequent times, such as t1 (during the shipping phase) and t2 (during the sensor session phase), for example, complex adaptive calibration factors $C_{t1}$ and $C_{t2}$ may be respectively obtained using $C_{M1}$ and the measured values of the parameters. Additional complex adaptive calibration factors may be obtained during the shipping phase (e.g., $C_{S1}$, $C_{S2}$ . . . $C_{Sn}$), the storage phase ($C_{ST1}$ and $C_{ST2}$), the pre in vivo phase (e.g., $C_P$) and the sensor session phase (e.g., $C_{SS1}$, $C_{SS2}$ . . . $C_{SSN}$). In this way the experience of the analyte sensor during its lifetime is encoded in a form that allows it to be used by a suitable calibration algorithm to determine, for instance, the sensitivity of the sensor and/or its baseline value.

In some embodiments, the continuous analyte sensor is an invasive, minimally invasive, or non-invasive device. The continuous analyte sensor can be a subcutaneous, transdermal, or intravascular device. In certain embodiments, one or more of these devices may form a continuous analyte sensor system. For instance, the continuous analyte sensor system may be comprised of a combination of a subcutaneous device and a transdermal device, a combination of a subcutaneous device and an intravascular device, a combination of a transdermal device and an intravascular device, or a combination of a subcutaneous device, a transdermal device, and an intravascular device. In some embodiments, the continuous analyte sensor can analyze a plurality of intermittent biological samples (e.g., blood samples). The continuous analyte sensor can use any glucose-measurement method, including methods involving enzymatic, chemical, physical, electrochemical, spectrophotometric, polarimetric, calorimetric, iontophoretic, and radiometric mechanisms, and the like.

In certain embodiments, the continuous analyte sensor includes one or more working electrodes and one or more reference electrode, which operate together to measure a signal associated with a concentration of the analyte in the host. The output signal from the working electrode is typically a raw data stream that is calibrated, processed, and used to generate an estimated analyte (e.g., glucose) concentration. In certain embodiments, the continuous analyte sensor may measure an additional signal associated with the baseline and/or sensitivity of the sensor, thereby enabling monitoring of baseline and/or additional monitoring of sensitivity changes or drift that may occur in a continuous analyte sensor over time.

In some embodiments, the sensor extends through a housing, which maintains the sensor on the skin and provides for electrical connection of the sensor to sensor electronics. In one embodiment, the sensor is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments the smallest dimension of the elongated conductive body is less than about 0.1 inches, 0.075 inches, 0.05 inches, 0.025 inches, 0.01 inches, 0.004 inches, or 0.002 inches. Other embodiments of the elongated conductive body are disclosed in U.S. Patent Application Publication No. 2011-0027127-A1, which is incorporated herein by reference in its entirety. Preferably, a membrane system is deposited over at least a portion of electroactive surfaces of the sensor 102 (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface. Disclosures regarding the different membrane systems that may be used with the embodiments described herein are described in U.S. Patent Publication No. US-2009-0247856-A1, which is incorporated herein by reference in its entirety.

In the prior art, calibrating sensor data from continuous analyte sensors generally involved defining a relationship between sensor-generated measurements (e.g., in units of nA or digital counts after A/D conversion) and one or more reference measurement (e.g., in units of mg/dL or mmol/L). In certain embodiments, one or more reference measurements obtained shortly after the analyte sensor is manufactured, and before sensor use, are used for calibration. The reference measurement may have been obtained in many forms. For example, in certain cases, the reference measurement may be determined from in vivo analyte concentration measurements.

With factory calibration or automatic self-calibration, the need for recalibration, by using reference data during a sensor session, may be eliminated, or else lessened, such that recalibration may be called for only in certain limited circumstances, such as when sensor failure is detected. Additionally or alternatively, in some embodiments, the continuous analyte sensor may be configured to request and accept one or more reference measurements (e.g., from a finger stick glucose measurement or a calibration solution) at the start of the sensor session. In some embodiments, use of a reference measurement at the start of the sensor session in conjunction with a predetermined sensor sensitivity profile can eliminate or substantially reduce the need for further reference measurements.

Turning to a basic description of glucose sensor functionality, with certain implantable enzyme-based electrochemical glucose sensors, the sensing mechanism depends on certain phenomena that have a generally linear relationship with glucose concentration, for example: (1) diffusion of an analyte through a membrane system situated between an implantation site (e.g., subcutaneous space) and an electroactive surface, (2) rate of an enzyme-catalyzed reaction of the analyte to produce a measured species within the membrane system (e.g., the rate of a glucose oxidase-catalyzed reaction of glucose with $O_2$ which produces gluconic acid and $H_2O_2$), and (3) diffusion of the measured species (e.g., $H_2O_2$) to the electroactive surface. Because of this generally linear relationship, calibration of the sensor is obtained by solving the equation:

$$y=mx+b$$

wherein y represents the sensor signal (counts), x represents the estimated glucose concentration (mg/dL), m represents the sensor sensitivity to analyte concentration (counts/mg/dL), and b represents the baseline signal (counts). As described elsewhere herein, in certain embodiments, the value b (i.e., the baseline) can be zero or about zero. As a result, for these embodiments, calibration can be defined by solving for the equation y=mx.

In some embodiments, the continuous analyte sensor system is configured to estimate changes or drift in sensitivity of the sensor for an entire sensor session as a function of time (e.g., elapsed time since start of the sensor session). As described elsewhere herein, this sensitivity function plotted against time may resemble a curve. Additionally or alternatively, the system can also be configured to determine sensor sensitivity changes or drift as a function of time and one or more other parameters that can also affect sensor sensitivity or provide additional information about sensor sensitivity. These parameters can affect sensor sensitivity or provide additional information about sensor sensitivity prior to the sensor session, such as parameters associated with the sensor fabrication (e.g., materials used to fabricate sensor membrane, the thickness of the sensor membrane, the temperature at which the sensor membrane was cured, the length of time the sensor was dipped in a particular coating solution, etc.). In certain embodiments, some of the parameters involve information, obtained prior to the sensor session, which can be accounted for in a calibration code that is associated with a particular sensor lot. Other parameters can be associated with conditions surrounding the sensor after its manufacture, but before the sensor session, such as, for example, the level of exposure of the sensor to certain levels of humidity or temperature while the sensor is in a package in transit from the manufacturing facility to the patient. Yet other parameters (e.g., sensor membrane permeability, temperature at the sample site, pH at the sample site, oxygen level at the sample site, etc.) can affect sensor sensitivity or provide additional information about sensor sensitivity during the sensor session.

Determination of sensor sensitivity at different times of a sensor session based on the predetermined sensor sensitivity profile can be performed prior to the sensor session or at the start of the sensor session. Additionally, in certain embodiments, determination of sensor sensitivity, based on the sensor sensitivity profile, can be continuously adjusted to account for parameters that affect sensor sensitivity or provide additional information about sensor sensitivity during the sensor session. These determinations of sensor sensitivity change or drift can be used to provide self-calibration, update calibration, supplement calibration based on measurements of known values (e.g., from a reference analyte monitor), and/or validate or reject reference analyte measurements from a reference analyte monitor. In some embodiments, validation or rejection of reference analyte measurements can be based on whether the reference analyte measurements are within a range of values associated with the predetermined sensor sensitivity profile.

Some of the continuous analyte sensors described herein may be configured to measure a signal associated with a non-analyte constant signal in the host. Preferably, the non-analyte constant signal is measured beneath the membrane system on the sensor. In one example of a continuous glucose sensor, a non-glucose constant signal that can be measured is oxygen. In some embodiments, a change in oxygen transport, which can be indicative of a change or drift in the sensitivity of the glucose signal, can be measured by switching the bias potential of the working electrode, an auxiliary oxygen-measuring electrode, an oxygen sensor, or the like.

Additionally, some of the continuous analyte sensors described herein may be configured to measure changes in the amount of background noise in the signal. Detection of changes which exceed a certain threshold can provide the basis for triggering calibration, updating calibration, and/or validating or rejecting inaccurate reference analyte values from a reference analyte monitor. In one example of a continuous glucose sensor, the background noise is composed substantially of signal contribution from factors other than glucose (for example, interfering species, non-reaction-related hydrogen peroxide, or other electroactive species with an oxidation potential that overlaps with hydrogen peroxide). Namely, the continuous glucose sensor is configured to measure a signal associated with the baseline (which includes substantially all non-glucose related current generated), as measured by the sensor in the host. In some embodiments, an auxiliary electrode located beneath a non-enzymatic portion of the membrane system is used to measure the baseline signal. The baseline signal can be subtracted from the glucose+baseline signal to obtain a signal associated entirely or substantially entirely with glucose concentration. Subtraction may be accomplished electronically in the sensor using a differential amplifier, digitally in the receiver, and/or otherwise in the hardware or software of the sensor or receiver as described in more detail elsewhere herein.

Together, by determining sensor sensitivity based on a sensitivity profile and by measuring a baseline signal, the continuous analyte sensor can be continuously self-calibrated during a sensor session without (or with reduced) reliance on reference measurements from a reference analyte monitor or calibration solution.

Sensor System

FIG. 1 depicts an example system 100, in accordance with some example implementations. The system 100 includes an analyte sensor system 101 including sensor electronics 112 and an analyte sensor 138. The system 100 may include other devices and/or sensors, such as medicament delivery pump 102 and glucose meter 104. The analyte sensor 138 may be physically connected to sensor electronics 112 and may be integral with (e.g., non-releasably attached to) or releasably attachable to the sensor electronics. For example, continuous analyte sensor 138 may be connected to sensor electronics 112 via a sensor interposer that mechanically and electrically interfaces the analyte sensor 138 with the sensor electronics. The sensor electronics 112, medicament delivery pump 102, and/or glucose meter 104 may couple with one or more devices, such as display devices 114, 116, 118, and/or 120.

In some example implementations, the system 100 may include a cloud-based analyte processor 490 configured to analyze analyte data (and/or other patient-related data) provided via network 409 (e.g., via wired, wireless, or a combination thereof) from sensor system 101 and other devices, such as display devices 114, 116, 118, and/or 120 and the like, associated with the host (also referred to as a patient) and generate reports providing high-level information, such as statistics, regarding the measured analyte over a certain time frame. A full discussion of using a cloud-based analyte processing system may be found in U.S. patent application Ser. No. 13/788,375, filed Mar. 7, 2013 and published as US-2013-0325352-A1, entitled "Cloud-Based Processing of Analyte Data", herein incorporated by reference in its entirety. In some implementations, one or more steps of the factory calibration or automatic self-calibration algorithm can be performed in the cloud.

In some example implementations, the sensor electronics 112 may include electronic circuitry associated with measuring and processing data generated by the analyte sensor 138. This generated analyte sensor data may also include algorithms, which can be used to process and calibrate the analyte sensor data, although these algorithms may be provided in other ways as well. The sensor electronics 112 may include hardware, firmware, software, or a combination thereof, to provide measurement of levels of the analyte via an analyte sensor, such as a glucose sensor. An example implementation of the sensor electronics 112 is described further below with respect to FIG. 2.

In one implementation, the factory or self calibration algorithms described herein may be performed by the sensor electronics.

The sensor electronics 112 may, as noted, couple (e.g., wirelessly and the like) with one or more devices, such as display devices 114, 116, 118, and/or 120. The display devices 114, 116, 118, and/or 120 may be configured for presenting information (and/or alarming), such as sensor information transmitted by the sensor electronics 112 for display at the display devices 114, 116, 118, and/or 120.

In one implementation, the factory or self calibration algorithms described herein may be performed at least in part by the display devices.

In some example implementations, the relatively small, key fob-like display device 114 may comprise a wrist watch, a belt, a necklace, a pendent, a piece of jewelry, an adhesive patch, a pager, a key fob, a plastic card (e.g., credit card), an identification (ID) card, and/or the like. This small display device 114 may include a relatively small display (e.g., smaller than the large display device 116) and may be configured to display certain types of displayable sensor information, such as a numerical value, and an arrow, or a color code.

In some example implementations, the relatively large, hand-held display device 116 may comprise a smart phone, hand-held receiver device, a palm-top computer, and/or the like. This large display device may include a relatively larger display (e.g., larger than the small display device 114) and may be configured to display information, such as a graphical representation of the sensor data including current and historic sensor data output by sensor system 100.

In some example implementations, the analyte sensor 138 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the analyte sensor 138 includes a glucose sensor, the glucose sensor may comprise any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the analyte sensor 138 may be implanted as at least one of the following types of analyte sensors: an implantable glucose sensor, a transcutaneous glucose sensor, implanted in a host vessel or extra corporeally, a subcutaneous sensor, a refillable subcutaneous sensor, an intravascular sensor.

Although the disclosure herein refers to some implementations that include an analyte sensor 138 comprising a glucose sensor, the analyte sensor 138 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. These may include, for example, fully implantable, subcutaneous, transcutaneous sensors. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

Figure 2:
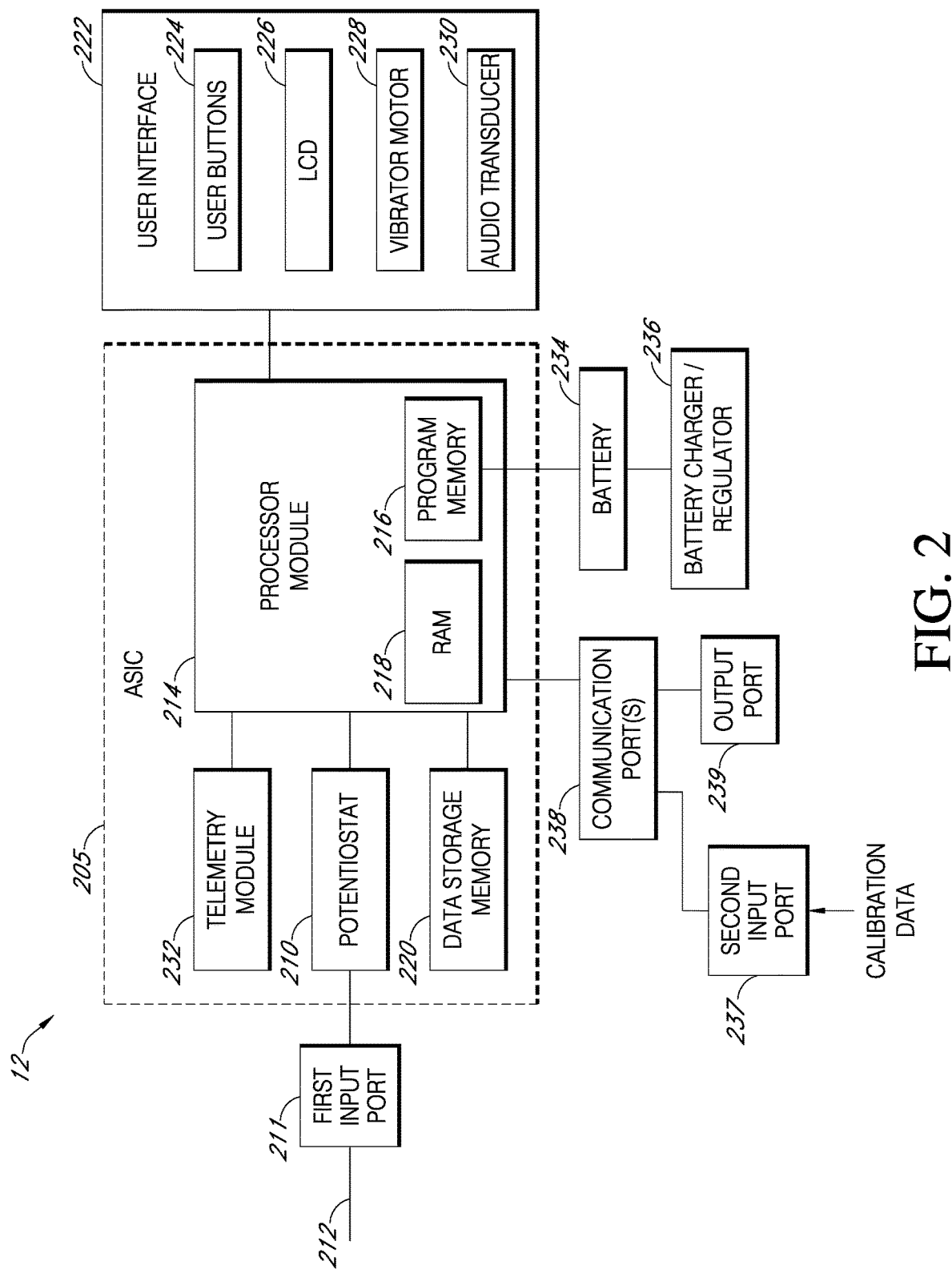
FIG. 2 is a block diagram that illustrates electronics associated with the sensor system of FIG. 1, according to some embodiments.

FIG. 2 depicts an example of electronics 12 that may be used in sensor electronics 112 or may be implemented in a manufacturing station such as a testing station, a calibration station, a smart carrier, or other equipment used during manufacturing of device 101, in accordance with some example implementations. The sensor electronics 112 may include electronics components that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information such as may be determined by factory or self-calibration algorithms as disclosed herein, smoothing and/or filtering algorithms of sensor data, and/or the like.

In some embodiments, a processor module 214 is configured to achieve a substantial portion, if not all, of the data processing, including data processing pertaining to factory or self-calibration. Processor module 214 may be integral to sensor electronics 12 and/or may be located remotely, such as in one or more of devices 114, 116, 118, and/or 120 and/or cloud 490. For example, in some embodiments, processor module 214 may be located at least partially within a cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 114, 116, 118, and/or 120, to enable calibration of the sensor data from sensor 138. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms. The processor module 214 may further be configured to store and use calibration information determined from a factory or self-calibration, as described below.

In some example implementations, the sensor electronics 112 may comprise an application-specific integrated circuit (ASIC) 205 coupled to a user interface 222. The ASIC 205 may further include a potentiostat 210, a telemetry module 232 for transmitting data from the sensor electronics 112 to one or more devices, such as devices 114, 116, 118, and/or 120, and/or other components for signal processing and data storage (e.g., processor module 214 and data storage memory 220). Although FIG. 1I depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted in FIG. 1I, through a first input port 211 for sensor data the potentiostat 210 is coupled to an analyte sensor 138, such as a glucose sensor to generate sensor data from the analyte. The potentiostat 210 may also provide via data line 212 a voltage to the analyte sensor 138 to bias the sensor for measurement of a value (e.g., a current and the like) indicative of the analyte concentration in a host (also referred to as the analog portion of the sensor). The potentiostat 210 may have one or more channels depending on the number of working electrodes at the analyte sensor 138.

In some example implementations, the potentiostat 210 may include a resistor that translates a current value from the sensor 138 into a voltage value, while in some example implementations, a current-to-frequency converter (not shown) may also be configured to integrate continuously a measured current value from the sensor 138 using, for example, a charge-counting device. In some example implementations, an analog-to-digital converter (not shown) may digitize the analog signal from the sensor 138 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 112 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although Bluetooth technology may also be implemented in a combination of the telemetry module 232 and the processor module 214.

The processor module 214 may control the processing performed by the sensor electronics 112. For example, the processor module 214 may be configured to process data (e.g., counts), from the sensor, filter the data, calibrate the data, perform fail-safe checking, and/or the like.

Potentiostat 210 may measure the analyte (e.g., glucose and/or the like) at discrete time intervals or continuously.

The processor module 214 may further include a data generator (not shown) configured to generate data packages for transmission to devices, such as the display devices 114, 116, 118, and/or 120. Furthermore, the processor module 214 may generate data packets for transmission to these outside sources via telemetry module 232. In some example implementations, the data packages may include an identifier code for the sensor and/or sensor electronics 112, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 138 (e.g., a sensor identifier (ID)) and for storing code (also referred to as program code) to configure the ASIC 205 to perform one or more of the operations/functions described herein. For example, the program code may configure processor module 214 to process data streams or counts, filter, perform the calibration methods described below, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, electrically erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of analyte sensor data. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information such as from factory calibration), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host).

The battery 234 may be operatively connected to the processor module 214 (and possibly other components of the sensor electronics 12) and provide the necessary power for the sensor electronics 112. In other implementations, the receiver can be transcutaneously powered via an inductive coupling, for example.

A battery charger and/or regulator 236 may be configured to receive energy from an internal and/or external charger. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 112. The communication port, for example, may comprise a serial (e.g., universal serial bus or "USB") communication port, and allow for communicating with another computer system (e.g., PC, personal digital assistant or "PDA," server, or the like). In some example implementations, factory information or other data may be sent to or received from the sensor, the algorithm or a cloud data source.

The one or more communication ports 238 may further include a second input port 237 in which calibration data may be received, and an output port 239 which may be employed to transmit calibrated data, or data to be calibrated, to a receiver or mobile device. FIG. 2 illustrates these aspects schematically. It will be understood that the ports may be separated physically, but in alternative implementations a single communication port may provide the functions of both the second input port and the output port.

In some analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 112 (e.g., via processor module 214) may be implemented to execute prospective algorithms used to generate transformed sensor data and/or displayable sensor information, including, for example, algorithms that: evaluate a clinical acceptability of optional reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like. A connected receiver or smart device or wearable may perform one or more of such calculations.

Figure 3:
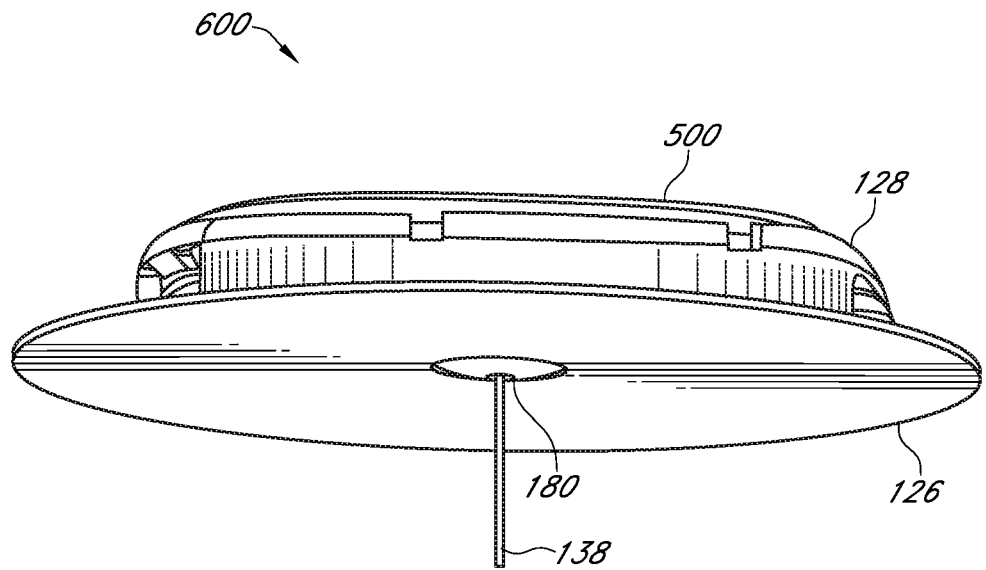
FIG. 3 illustrates a perspective view of a wearable device having an analyte sensor, according to some embodiments.

FIG. 3 illustrates a perspective view of an exemplary implementation of analyte sensor system 101 implemented as a wearable device such as an on-skin sensor assembly 600. As shown in FIG. 3, on-skin sensor assembly includes a base 128. An adhesive 126 can couple base 128 to the skin of the host. The adhesive 126 can be an adhesive suitable for skin adhesion but not generally, e.g., foam-based adhesives.

In some embodiments, electronics unit 500 (e.g., a transmitter) may be coupled to base 128 (e.g., via mechanical interlocks such as snap fits and/or interference features). The electronics unit 500 can include sensor electronics 112 operable to measure and/or analyze glucose indicators sensed by glucose sensor 138. Sensor electronics 112 within electronics unit 500 can transmit information (e.g., measurements, analyte data, and glucose data) to a remotely located device (e.g., 114-120 shown in FIG. 1).

Sensor 138 may be provided as a part of a preconnected sensor that includes a sensor interposer. The sensor interposer (not visible in FIG. 3) may be secured between base 128 and electronics unit 500 and electrically coupled to electronics unit 500 to couple sensor 138 to the sensor electronics (e.g., sensor electronics 112 of FIG. 1).

Figure 4:
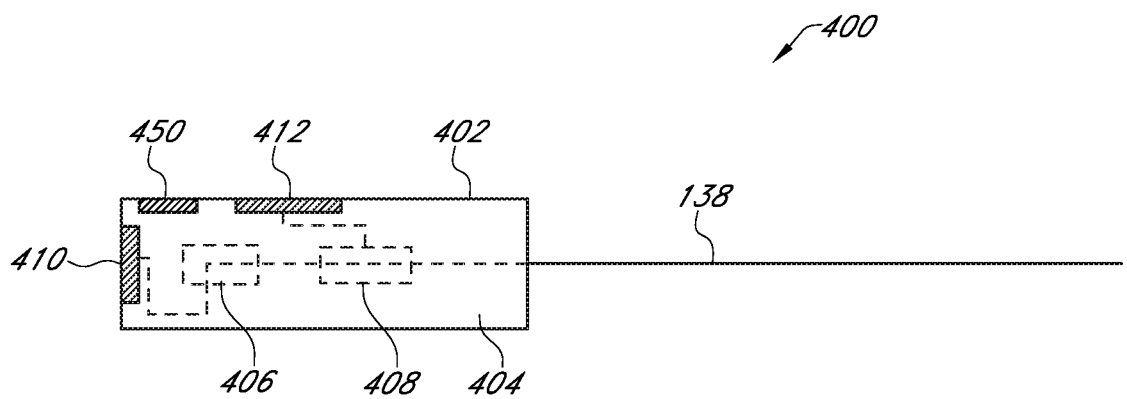
FIG. 4 illustrates a schematic of a preconnected analyte sensor, according to some embodiments.

FIG. 4 shows a schematic illustration of a preconnected sensor 400. As shown in FIG. 4, preconnected sensor 400 includes sensor interposer 402 permanently attached to sensor 138. In the example of FIG. 4, sensor interposer 402 includes substrate 404, first contact 406, and second contact 408. Contact 406 is electrically coupled to a first contact on a proximal end of sensor 138 and contact 408 is electrically coupled to a second contact on the proximal end of sensor 138. The distal end of sensor 138 is a free end configured for insertion into the skin of the host.

As shown in FIG. 4, contact 406 is coupled to an external contact 410 and contact 408 is coupled to an external contact 412. As described in further detail hereinafter, external contacts 410 and 412 are sized, shaped, and positioned to electrically interface with sensor electronics 112 in electronics unit 500 in addition to electrically interfacing with processing circuitry of manufacturing equipment such one or more testing stations and/or one or more calibration stations. Although various examples are described herein in which two contacts 410 and 412 on the interposer are coupled to two corresponding contacts 406 and 408 on sensor 138, this is merely illustrative. In other implementations, interposer 402 and sensor 138 may each be provided with a single contact or may each be provided with more than two contacts. In some implementations, interposer 402 and sensor 138 may have a same number of contacts. In some implementations, interposer 402 and sensor 138 may have a different number of contacts. For example, in some implementations, interposer 402 may have additional contacts for coupling to or between various components of a manufacturing station.

Substrate 404 may be sized and shaped to mechanically interface with base 128 and/or electronics unit 500 in addition to mechanically interfacing with manufacturing equipment such one or more assembly equipment, testing stations and/or one or more calibration stations. Interposer 402 may be attached and/or electrically coupled to sensor 138. Interposer 402 may be attached to sensor 138 using, as examples, adhesive, spring contacts, wrapped flexible circuitry, a conductive elastomer, a barrel connector, a molded interconnect device structure, magnets, anisotropic conductive films, or other suitable structures or materials for mechanically and electrically attaching interposer 402 to sensor 138 before or during assembly, manufacturing, testing and/or calibration operations. Interposer 402 may be attached to sensor 138 using, as examples, spot welding, swaging, crimping, clipping, soldering or brazing, plastic welding, overmolding, or other suitable methods for mechanically and electrically attaching interposer 402 to sensor 138 before or during assembly, manufacturing, testing and/or calibration operations. Substrate 404 may include datum features (sometimes referred to as datum structures) such as a recess, an opening, a surface or a protrusion for aligning, positioning, and orienting sensor 138 relative to interposer 402. Substrate 404 may also include, or may itself form, one or more anchoring features for securing and aligning the analyte sensor during manufacturing (e.g., relative to a manufacturing station).

Figure 5:
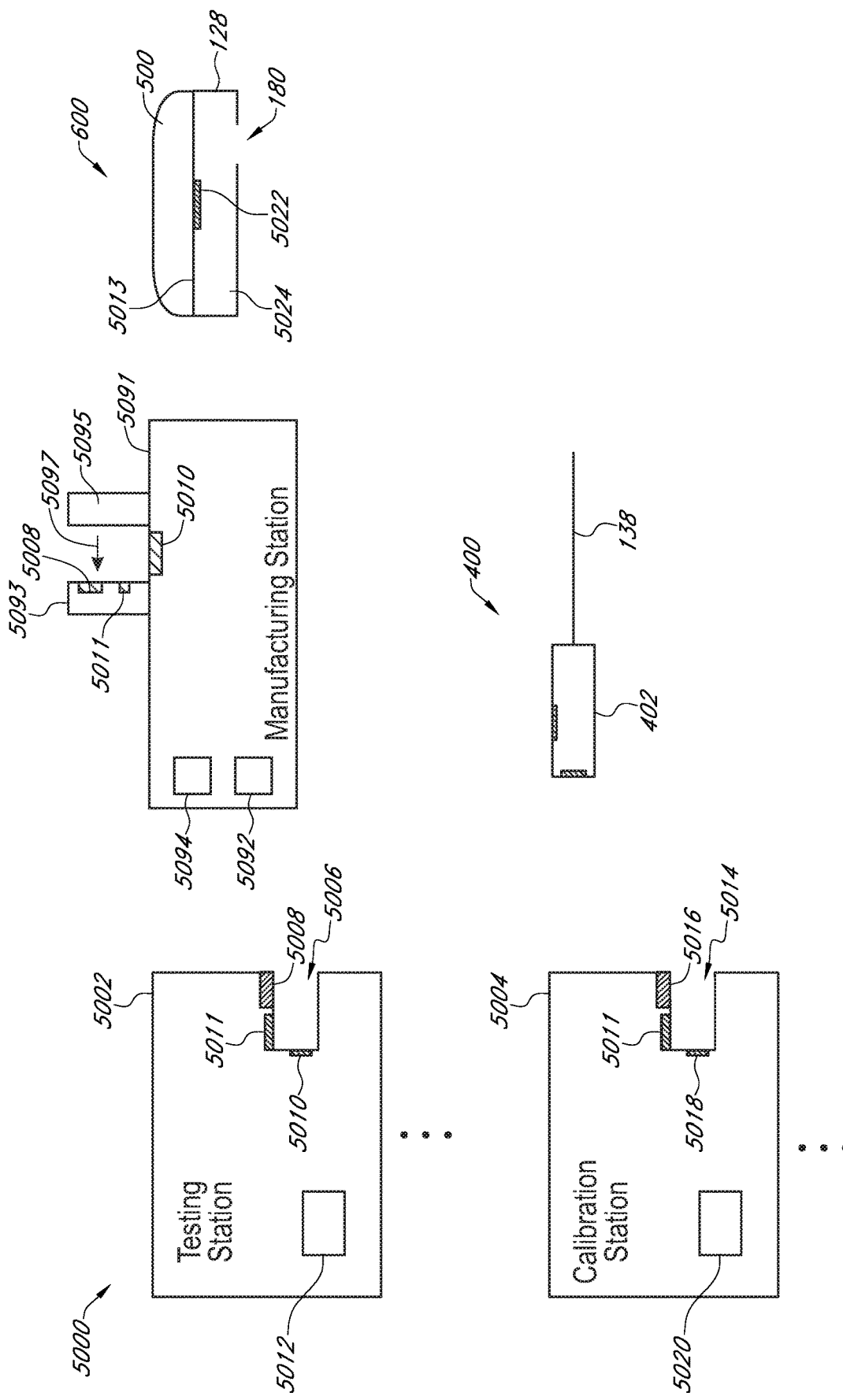
FIG. 5 illustrates a block diagram of a system having a manufacturing system and a wearable device for an analyte sensor, according to some embodiments.

FIG. 5 shows a block diagram of an exemplary system 5000 having manufacturing equipment such as one or more manufacturing stations 5091, one or more positioning or testing stations 5002 and/or one more calibration stations 5004, and having an on-skin sensor assembly 600, each configured to receive sensor interposer 402 and to communicatively couple to sensor 138 via sensor interposer 402.

System 5000 may include one or more positioning or testing stations 5002 having processing circuitry 5012 configured to perform testing operations with sensor 138 to determine parameters and/or to verify the operational integrity of sensor 138. Testing operations may include verifying electrical properties of a sensor 138, verifying communication between a working electrode and contact 408, verifying communication between a reference electrode or additional electrodes and contact 406, and/or other electronic verification operations for sensor 138. Processing circuitry 5012 may be communicatively coupled with sensor 138 for testing operations by inserting substrate 404 into a receptacle 5006 (e.g., a recess in a housing of testing station 5002) until contact 410 is coupled to contact 5010 of testing station 5002 and contact 412 is coupled to contact 5008 of testing station 5002.

System 5000 may include one or more calibration stations 5004 having processing circuitry 5020 configured to perform calibration operations with sensor 138 to obtain calibration data for in vivo operation of sensor 138. Calibration data obtained by calibration equipment 5004 may be provided to on-skin sensor assembly 600 to be used during operation of sensor 138 in vivo. Processing circuitry 5020 may be communicatively coupled with sensor 138 for calibration operations by inserting substrate 404 into a receptacle 5014 (e.g., a recess in a housing of calibration station 5004) until contact 410 is coupled to contact 5018 of testing station 5002 and contact 412 is coupled to contact 5016 of testing station 5002.

System 5000 may include one or more manufacturing stations 5091. Manufacturing station 5091 may also serve in providing the functions of a testing station as described herein, a calibration station as described herein, or another manufacturing station. Manufacturing station 5091 may include processing circuitry 5092 and/or mechanical components 5094 operable to perform testing operations, calibration operations, and/or other manufacturing operations such as sensor straightening operations, membrane application operations, baking operations, calibration-check operations, glucose sensitivity operations (e.g., sensitivity slope, baseline, and/or noise calibration operations), and/or visual inspection operations. Manufacturing parameters that may be measured during these various operations may include, by way of illustration, temperature, humidity, the content (e.g., PVP, ethanol, etc.) of the particular coating solution in which the sensor is dipped (which may be determined from the refractive index of the solution), the duration of the dip, the number of times the sensors are dipped in the solution, and the duration, temperature and humidity of the curing process.

In the example of FIG. 5, testing station 5002 and calibration station 5004 include receptacles 5006 and 5014. However, this is merely illustrative and interposer 402 may be mounted to testing station 5002 and calibration station 5004 and/or manufacturing station 5091 using other mounting features such as grasping, clipping, or clamping figures. For example, manufacturing station 5091 includes grasping structures 5093 and 5095, at least one of which is movable to grasp interposer 402 (or a carrier having multiple interposers and sensors). Structure 5093 may be a stationary feature having one or more electrical contacts such as contact 5008. Structure 5095 may be a movable feature that moves (e.g., slides in a direction 5097) to grasp and secure interposer 402 in an electrically coupled position for manufacturing station 5091. In other implementations, both features 5093 and 5095 are movable.

Sensor interposer 402 may also include an identifier 450 (see, e.g., FIG. 4). Identifier 450 may be formed on or embedded within substrate 404. Identifier 450 may be implemented as a visual or optical identifier (e.g., a barcode pre-printed or printed on-the-fly on substrate 404 or etched in to substrate 404), a radio frequency (RF) identifier, or an electrical identifier (e.g., a laser-trimmed resistor, a capacitive identifier, an inductive identifier, or a micro storage circuit (e.g., an integrated circuit or other circuitry in which the identifier is encoded in memory of the identifier) programmable with an identifier and/or other data before, during, or after testing and calibration). Identifier 450 may be used for tracking each sensor through the manufacturing process for that sensor (e.g., by storing a history of testing and/or calibration data for each sensor). For example, identifier 450 may be used for binning of testing and calibration performance data. Identifier 450 may be a discrete raw value or may encode information in addition to an identification number. Identifier 450 may be used for digitally storing data in non-volatile memory on substrate 404 or as a reference number for storing data external to interposer 402.

Testing station 5002 may include a reader 5011 (e.g., an optical sensor, an RF sensor, or an electrical interface such as an integrated circuit interface) that reads identifier 450 to obtain a unique identifier of sensor 138. Testing data obtained by testing station 5002 may be stored and/or transmitted along with the identifier of sensor 138.

Calibration station 5004 may include a reader 5011 (e.g., an optical sensor, an RF sensor, or an electrical interface) that reads identifier 450 to obtain a unique identifier of sensor 138. Calibration data obtained by calibration station 5004 may be stored and/or transmitted along with the identifier of sensor 138. In some implementations, calibration data obtained by calibration station 5004 may be added to identifier 450 by calibration station 5004 (e.g., by programming the calibration data into the identifier). In some implementations, calibration data obtained by calibration station 5004 may be transmitted to a remote system or device along with identifier 450 by calibration station.

As shown in FIG. 5, on-skin sensor assembly 600 may include one or more contacts such as contact 5022 configured to couple electronics unit 500 to contacts 410 and 412 of interposer 402 and thus to sensor 138. Interposer 402 may be sized and shaped to be secured within a cavity 5024 between base 128 and electronics unit 500 such that sensor 138 is coupled to electronics unit 500 via interposer 402, identifier 450 is accessible by reader 5013, and sensor 138 is positionally secured to extend through opening 180 for insertion for in vivo operations.

Although one calibration station and one testing station are shown in FIG. 5, it should be appreciated that more than one testing station and/or more than one calibration station may be included in system 5000. Although calibration station 5004 and testing station 5002 are shown as separate stations in FIG. 5, it should be appreciated that, in some implementations calibration stations and testing stations may be combined into one or more calibration/testing stations (e.g., stations in which processing circuitry for performing testing and calibration operations is provided within a common housing and coupled to a single interface 5006). In addition, data from one or more manufacturing stations may be compiled and stored in and/or stored and associated with the sensor and interposer.

On-skin sensor assembly 600 may also include a reader 5013 (e.g., an optical sensor, an RF sensor, or an electrical interface) that reads identifier 450 to obtain a unique identifier of sensor 138. Sensor electronics in electronics unit 500 may obtain calibration data for in vivo operation of sensor 138 based on the read identifier 450. The calibration data may be stored in, and obtained, from identifier 450 itself, or identifier 450 may be used to obtain the calibration data for the installed sensor 138 from a remote system such as a cloud-based system.

Additional details concerning the example of the sensor system shown FIGS. 1-5 may be found in U.S. Pat. Appl. Ser. No. 62/576,560, filed Oct. 24, 2017, entitled "Preconnected Analyte Sensors," which is hereby incorporated by reference in its entirety.

Determination of Sensor Sensitivity

As described elsewhere herein, in certain embodiments, self-calibration of the analyte sensor system can be performed by determining sensor sensitivity based on a sensitivity profile (and a measured or estimated baseline), so that the following equation can be solved:

$$y = mx + b$$

wherein y represents the sensor signal (counts), x represents the estimated glucose concentration (mg/dL), m represents the sensor sensitivity to the analyte (counts/mg/dL), and b represents the baseline signal (counts). From this equation, a conversion function can be formed, whereby a sensor signal is converted into an estimated glucose concentration.

Figure 6:
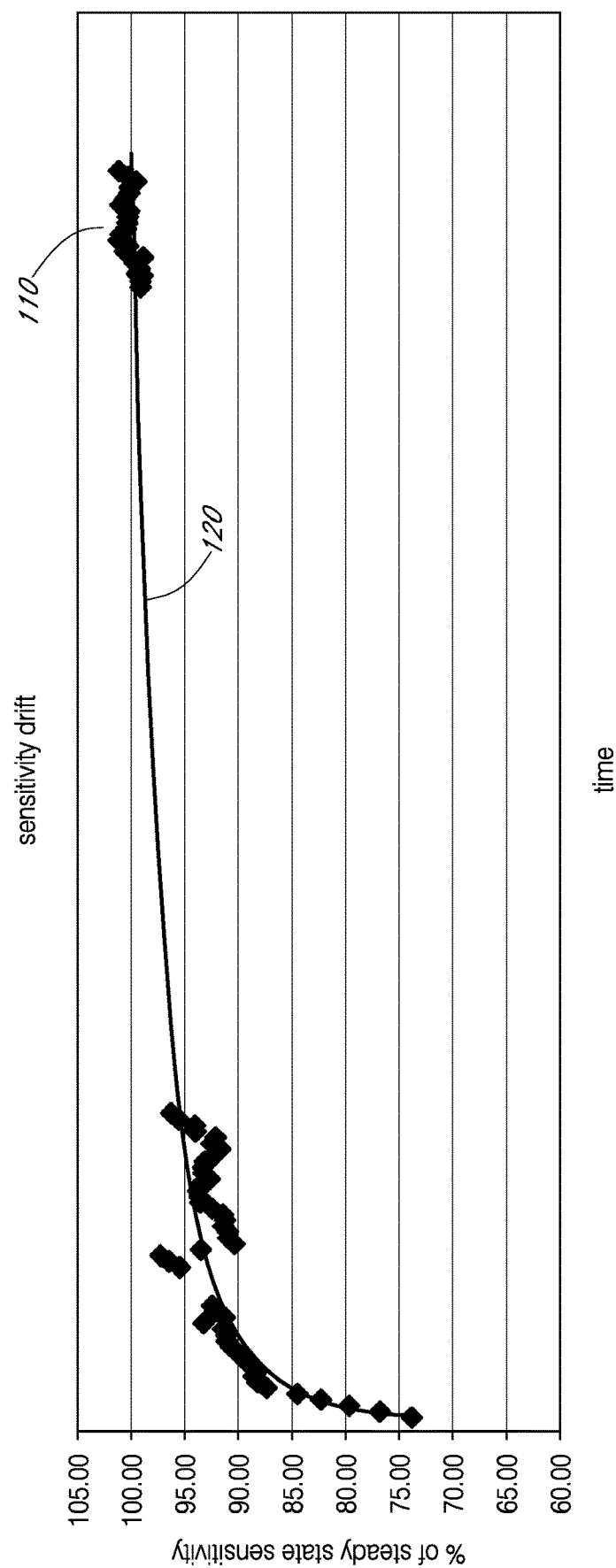
FIG. 6 illustrates a schematic diagram of sensor sensitivity as a function of time during a sensor session, in accordance with one embodiment.
Figure 7:
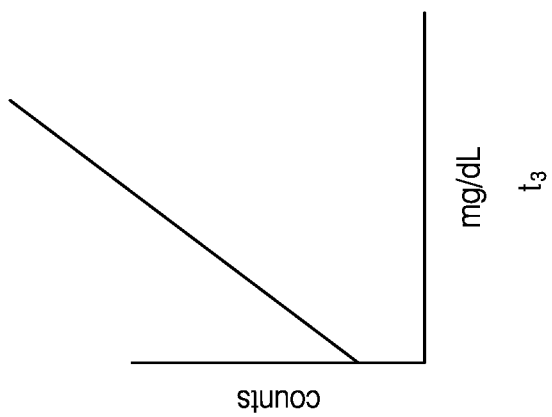
FIG. 7 illustrates schematic diagrams of conversion functions at different time periods of a sensor session, in accordance with the embodiment of FIG. 6.
Figure 7:
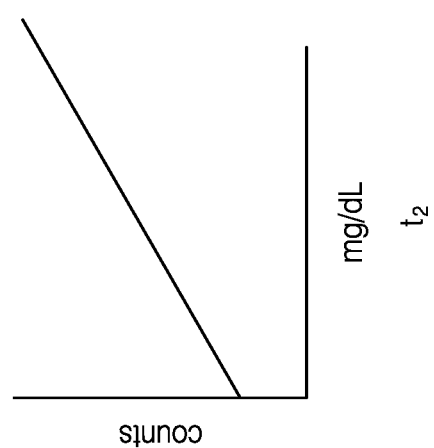
Figure 7:
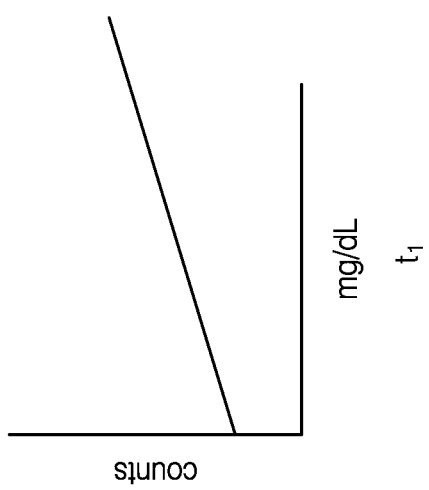

It has been found that a sensor's sensitivity to analyte concentration during a sensor session will often change or drift as a function of time. FIG. 6 illustrates this phenomenon and provides a plot of sensor sensitivities 110 of a group of continuous glucose sensors as a function of time during a sensor session. FIG. 7 provides three plots of conversion functions at three different time periods of a sensor session. As shown in FIG. 7, the three conversion functions have different slopes, each of which correspond to a different sensor sensitivity. Accordingly, the differences in slopes over time illustrate that changes or drift in sensor sensitivity occur over a sensor session.

Referring back to the study associated with FIG. 6, the sensors were made in substantially the same way under substantially the same conditions. The sensor sensitivities associated with the y-axis of the plot are expressed as a percentage of a substantially steady state sensitivity that was reached about three days after start of the sensor session. In addition, these sensor sensitivities correspond to measurements obtained from YSI tests. As shown in the plot, the sensitivities (expressed as a percentage of a steady state sensitivity) of each sensor, as measured, are very close to sensitivities of other sensors in the group at any given time of the sensor session. While not wishing to be bound by theory, it is believed that the observed upward trend in sensitivity (over time), which is particularly pronounced in the early part of the sensor session, can be attributed to conditioning and hydration of sensing regions of the working electrode. It is also believed that the glucose concentration of the fluid surrounding the continuous glucose sensor during startup of the sensor can also affect the sensitivity drift.

With the sensors tested in this study, the change in sensor sensitivity (expressed as a percentage of a substantially steady state sensitivity), over a time defined by a sensor session, resembled a logarithmic growth curve. It should be understood that other continuous analyte sensors fabricated with different techniques, with different specifications (e.g., different membrane thickness or composition), or under different manufacturing conditions, may exhibit a different sensor sensitivity profile (e.g., one associated with a linear function). Nonetheless, with improved control over operating conditions of the sensor fabrication process, high levels of reproducibility have been achieved, such that sensitivity profiles exhibited by individual sensors of a sensor population (e.g., a sensor lot) are substantially similar and sometimes nearly identical.

It has been discovered that the change or drift in sensitivity over a sensor session is not only substantially consistent among sensors manufactured in substantially the same way under substantially same conditions, but also that modeling can be performed through mathematical functions that can accurately estimate this change or drift. As illustrated in FIG. 6, an estimative algorithm function 120 can be used to define the relationship between time during the sensor session and sensor sensitivity. The estimative algorithm function may be generated by testing a sample set (comprising one or more sensors) from a sensor lot under in vivo and/or in vitro conditions. Alternatively, the estimative algorithm function may be generated by testing each sensor under in vivo and/or in vitro conditions.

In some embodiments, a sensor may undergo an in vitro sensor sensitivity drift test, in which the sensor is exposed to changing conditions (e.g., step changes of glucose concentrations in a solution), and an in vitro sensitivity profile of the sensor is generated over a certain time period. The time period of the test may substantially match an entire sensor session of a corresponding in vivo sensor, or it may encompass a portion of the sensor session (e.g., the first day, the first two days, or the first three days of the sensor session, etc.). It is contemplated that the above-described test may be performed on each individual sensor, or alternatively on one or more sample sensors of a sensor lot. From this test, an in vitro sensitivity profile may be created, from which an in vivo sensitivity profile may be modeled and/or formed.

From the in vivo or in vitro testing, one or more data sets, each comprising data points associating sensitivity with time, may be generated and plotted. A sensitivity profile or curve can then be fitted to the data points. If the curve fit is determined to be satisfactory (e.g., if the standard deviation of the generated data points is less a certain threshold), then the sensor sensitivity profile or curve may be judged to have passed a quality control and suitable for release. From there, the sensor sensitivity profile can be transformed into an estimative algorithm function or alternatively into a look-up table. The algorithm function or look-up table can be stored in a computer-readable memory, for example, and accessed by a computer processor.

The estimative algorithm function may be formed by applying curve fitting techniques that regressively fit a curve to data points by adjusting the function (e.g., by adjusting constants of the function) until an optimal fit to the available data points is obtained. Simply put, a "curve" (i.e., a function sometimes referred to as a "model") is fitted and generated that relates one data value to one or more other data values and selecting parameters of the curve such that the curve estimates the relationship between the data values. By way of example, selection of the parameters of the curve may involve selection of coefficients of a polynomial function. In some embodiments, the curve fitting process may involve evaluating how closely the curve determined in the curve fitting process estimates the relationship between the data values, to determine the optimal fit. The term "curve," as used herein, is a broad term, and is to be given its ordinary and customary meaning to a person of ordinary skill in the art (and is not to be limited to a special or customized meaning), and refers to a function or a graph of a function, which can involve a rounded curve or a straight curve, i.e., a line.

The curve may be formed by any of a variety of curve fitting techniques, such as, for example, the linear least squares fitting method, the non-linear least squares fitting method, the Nelder-Mead Simplex method, the Levenberg-Marquardt method, and variations thereof. In addition, the curve may be fitted using any of a variety of functions, including, but not limited to, a linear function (including a constant function), logarithmic function, quadratic function, cubic function, square root function, power function, polynomial function, rational function, exponential function, sinusoidal function, and variations and combinations thereof. For example, in some embodiments, the estimative algorithm comprises a linear function component which is accorded a first weight w1, a logarithmic function component which is accorded a second weight w2, and an exponential function component which is accorded a third weight w3. In further embodiments, the weights associated with each component can vary as a function of time and/or other parameters, but in alternative embodiment, one or more of these weights are constant as a function of time.

In certain embodiments, the estimative algorithm function's correlation (e.g., R2 value), which is a measure of the quality of the fit of the curve to the data points, with respect to data obtained from the sample sensors, may be one metric used to determine whether a function is optimal. In certain embodiments, the estimative algorithm function formed from the curve fitting analysis may be adjusted to account for other parameters, e.g., other parameters that may affect sensor sensitivity or provide additional information about sensor sensitivity. For example, the estimative algorithm function may be adjusted to account for the sensitivity of the sensor to hydrogen peroxide or other chemical species.

Estimative algorithms formed and used to accurately estimate an individual sensor's sensitivity, at any time during a sensor session, can be based on factory calibration and/or based on a single early reference measurement (e.g., using a single point blood glucose monitor). In some embodiments, sensors across a population of continuous analyte sensors manufactured in substantially the same way under substantially same conditions exhibit a substantially fixed in vivo to in vitro sensitivity relationship. For example, in one embodiment, the in vivo sensitivity of a sensor at a certain time after start of sensor use (e.g., at t=about 5, 10, 15, 30, 60, 120, or 180 minutes after sensor use) is consistently equal to a measured in vitro sensitivity of the sensor or of an equivalent sensor. From this relationship, an initial value of in vivo sensitivity can be generated, from which an algorithmic function corresponding to the sensor sensitivity profile can be formed. Put another way, from this initial value (which represents one point in the sensor sensitivity profile), the rest of the entire sensor sensitivity profile can be determined and plotted. The initial value of in vivo sensitivity can be associated with any portion of the sensor sensitivity profile. In certain embodiments, multiple initial values of in vivo sensitivities, which are time-spaced apart, and which correspond to multiple in vitro sensitivities, can be calculated and combined together to generate the sensor sensitivity profile.

With some embodiments, it has been found that not only does the sensor's sensitivity tend to drift over time, but that the sensor's baseline also drifts over time. Accordingly, in certain embodiments, the concepts behind the methods and systems used to predict sensitivity drift can also be applied to create a model that predicts baseline drift over time. Although not wishing to be bound by theory, it is believed that the total signal received by the sensor electrode is comprised of a glucose signal component, an interference signal component, and a electrode-related baseline signal component that is a function of the electrode and that is substantially independent of the environment (e.g., extracellular matrix) surrounding the electrode. As noted above, the term "baseline," as used herein, refers without limitation to the component of an analyte sensor signal that is not related to the analyte concentration. Accordingly, the baseline, as the term is defined herein, is comprised of the interference signal component and the electrode-related baseline signal component. Again, while not wishing to be bound by theory, it is believed that increased membrane permeability typically not only results in an increased rate of glucose diffusion across the sensor membrane, but also in an increased rate of diffusion of interferents across the sensor membrane. Accordingly, changes in sensor membrane permeability over time, which causes sensor sensitivity drift, will similarly also likely cause the interference signal component of the baseline to drift. Simply put, the interference signal component of the baseline is not static, and is typically changing as a function of time, which, in turn, causes the baseline to also drift over time. By analyzing how each of the aforementioned components of the baseline reacts to changing conditions and to time (e.g., as a function of time, temperature), a predictive model can be developed to predict how the baseline of a sensor will drift during a sensor session. By being able to prospectively predict both sensitivity and baseline of the sensor, it is believed that a factory calibrated or automatically self-calibrating continuous analyte sensor can be achieved, i.e., a sensor that does not require use of reference measurements (e.g., a fingerstick measurement) for calibration.

Calibration Code

The process of manufacturing continuous analyte sensors may sometimes be subjected to a degree of variability between sensor lots, as will be described in greater detail below. To compensate for this variability, one or more calibration codes may be assigned to each sensor or sensor set to define parameters that can affect sensor sensitivity or provide additional information about the sensitivity profile. The calibration codes can reduce variability in the different sensors, ensuring that the results obtained from using sensors from different sensors lots will be generally equal and consistent by applying an algorithm that adjusts for the differences. In one embodiment, the analyte sensor system may be configured such that one or more calibration codes are to be manually entered into the system by a user. In other embodiments, the calibration codes may be part of a calibration encoded label that is adhered to (or inserted into) a package of multiple sensors. The calibration encoded label itself may be read or interrogated by any of a variety of techniques, including, but not limited to, optical techniques, RFID (radio-frequency identification), or the like, and combinations thereof. These techniques for transferring the code to the sensor system may be more automatic, accurate, and convenient for the patient, and less prone to error, as compared to manual entry. Manual entry, for instance, possesses the inherent risk of an error caused by a patient or hospital staff entering the wrong code, which can lead to an incorrect calibration, and thus inaccurate glucose concentration readings. In turn, this may result in a patient or hospital staff taking an inappropriate action (e.g., injecting insulin while in a hypoglycemic state).

In some embodiments, calibration codes assigned to a sensor may include a first calibration code associated with a predetermined logarithmic function corresponding to a sensitivity profile, a second calibration code associated with an initial in vivo sensitivity value, and other calibration codes, with each code defining a parameter that affects sensor sensitivity or provides information about sensor sensitivity. The other calibration codes may be associated with any a priori information or parameter described elsewhere herein and/or any parameter that helps define a mathematical relationship between the measured signal and analyte concentration. The calibration code may be developed from these measurements or may be developed based on manufacturing parameters known, determined, or measured during fabrication of, e.g., a lot, or by a combination of these.

In some embodiments, the package used to store and transport a continuous analyte sensor (or sensor set) may include detectors configured to measure certain parameters that may affect sensor sensitivity or provide additional information about sensor sensitivity or other sensor characteristics. For example, in one embodiment, the sensor package may include a temperature detector configured to provide calibration information relating to whether the sensor has been exposed to a temperature state greater than (and/or less than) one or more predetermined temperature values. In some embodiments, the one or more predetermined temperature value may be greater than about 75° F., greater than about 80° F., greater than about 85° F., greater than about 90° F., greater than about 95° F., greater than about 100° F., greater than about 105° F., and/or greater than about 110° F. Additionally or alternatively, the one or more predetermined temperature value may be less than about 75° F., less than about 70° F., less than about 60° F., less than about 55° F., less than about 40° F., less than about 32° F., less than about 10° F., and/or less than about 0° F. In certain embodiments, the sensor package may include a humidity exposure indicator configured to provide calibration information relating to whether the sensor has been exposed to humidity levels greater than or less than one or more predetermined humidity values. In some embodiments, the one or more predetermined humidity value may be greater than about 60% relative humidity, greater than about 70% relative humidity, greater than about 80% relative humidity, and/or greater than about 90% relative humidity. Alternatively or additionally, the one or more predetermined humidity value may be less than about 30% relative humidity, less than about 20% relative humidity, and/or less than about 10% relative humidity.

Upon detection of exposure of the sensor to certain levels of temperature and/or humidity, a corresponding calibration code may be changed to account for possible effects of this exposure on sensor sensitivity or other sensor characteristics. This calibration code change may be automatically performed by a control system associated with the sensor package. Alternatively, in other embodiments, an indicator (e.g., a color indicator) that is adapted to undergo a change (e.g., a change in color) upon exposure to certain environments may be used. By way of example and not to be limiting, the sensor package may include an indicator that irreversibly changes color from a blue color to a red color, upon exposure of the package to a temperature greater than about 85° F., and also include instructions to the user to enter a certain calibration code when the indicator has a red color. Although exposure to temperature and humidity are described herein as examples of conditions that may be detected by the sensor package, and used to activate a change in calibration code information, it should be understood that other conditions may also be detected and used to activate a change in calibration code information.

In certain embodiments, the continuous analyte system may comprise a library of stored sensor sensitivity functions or calibration functions associated with one or more calibration codes. Each sensitivity function or calibration function results in calibrating the system for a different set of conditions. Different conditions during sensor use may be associated with temperature, body mass index, and any of a variety of conditions or parameters that may affect sensor sensitivity or provide additional information about sensor sensitivity. The library can also include sensitivity profiles or calibrations for different types of sensors or different sensor lots. For example, a single sensitivity profile library can include sub-libraries of sensitivity profiles for different sensors made from different sensor lots and/or made with different design configurations (e.g., different design configurations customized for patients with different body mass index).

Advanced and/or Multivariate Calibration

Figure 8A:
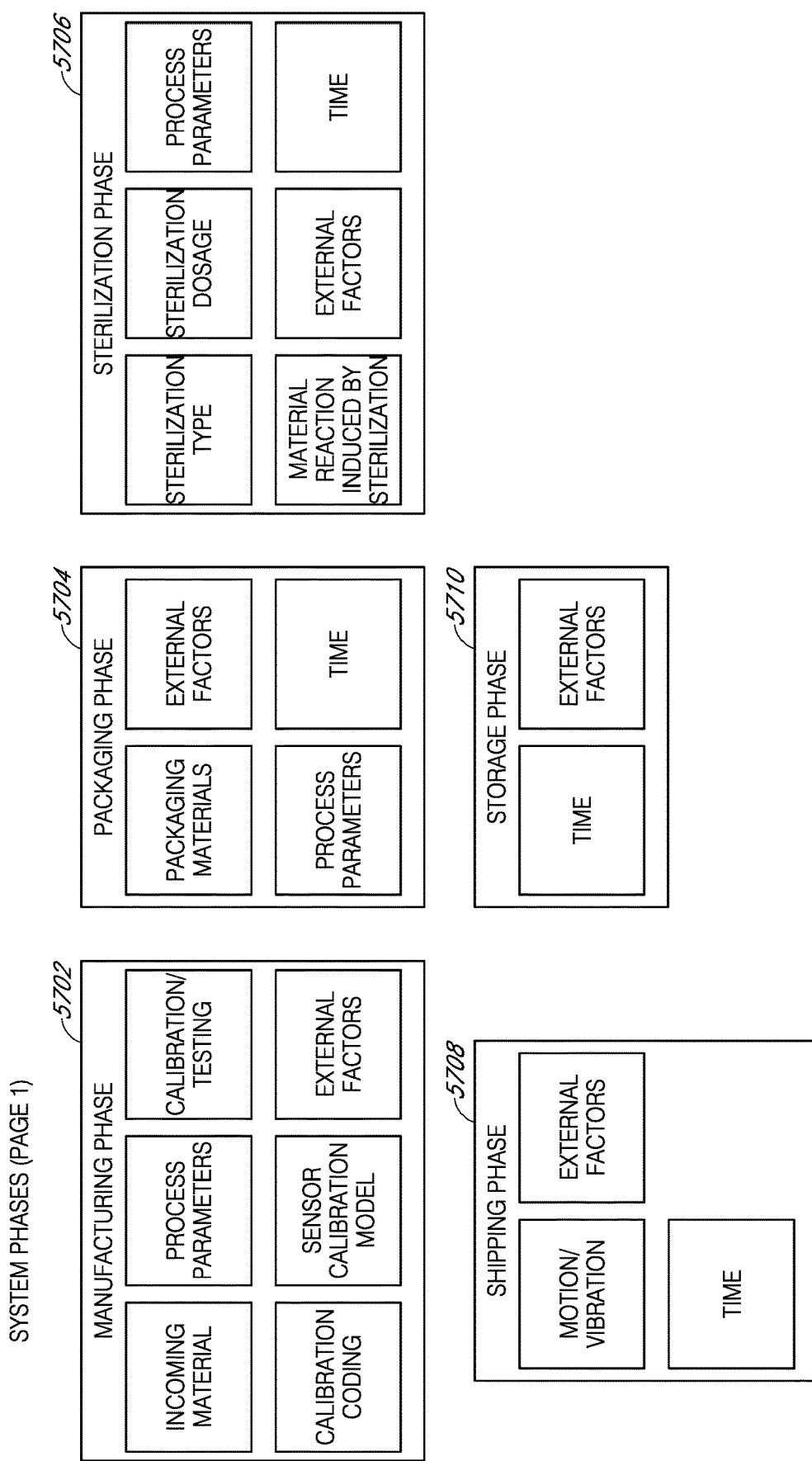
FIGS. 8A-8B show examples of various phases in an analyte sensor system lifecycle.
Figure 8B:
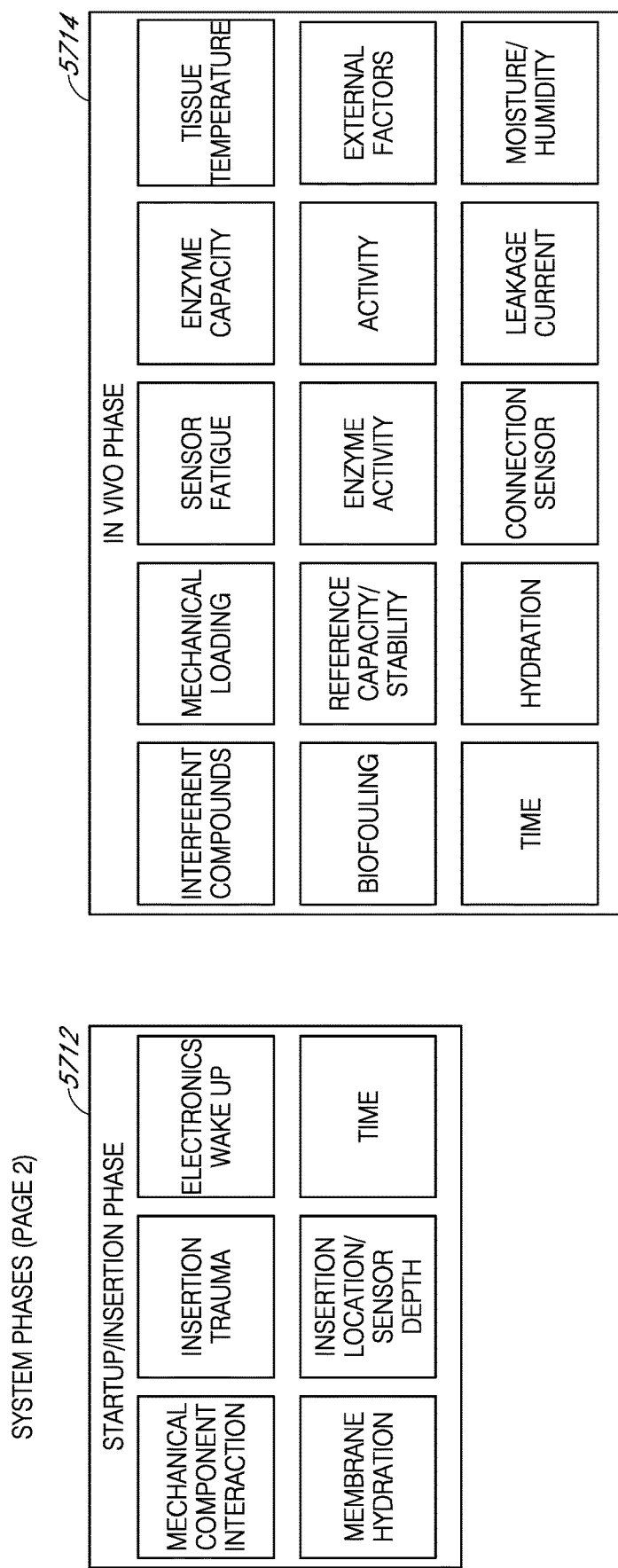

As previously mentioned, the sensitivity of an analyte sensor may change over time as a result of a variety of different manufacturing and environmental parameters. In some embodiments some of these parameters involve information that can be obtained during distinct phases of the analyte sensor lifecycle. As shown in FIGS. 8A and 8B, in certain embodiments these different phases may include one or more of the following: a sensor manufacturing phase 5702, a sensor packaging phase 5704, a sensor package sterilization phase 5706 in which the sensor is sterilized while in the package (using, e.g., any suitable sterilization gas, which may include conventional sterilization gases or, alternatively, nitrogen dioxide, chlorine dioxide or ethylene oxide, or alternatively, using an e-beam, at least to sterilize the transmitter, whose interior may be shielded to deflect the e-beam), a sensor shipping phase 5708, a sensor storage phase 5710 (e.g., in a warehouse, retail environment, user premises), a sensor startup/insertion phase 5712 during which the sensor is placed in vivo, and a sensor in vivo phase 5714 in which the sensor is operational while in vivo. Of course, in other embodiments, the analyte sensor lifecycle may be divided into different lifecycles. FIGS. 8A-8B further show examples of environmental and other factors that may be monitored during each lifecycle phase and which may be taken into account when calibrating the sensor.

Moreover, the various lifecycle phases enumerated above in some cases may be further divided into identifiable sub-stages. For instance, in some embodiments the sensor manufacturing phase may include a sub-phase in which the analyte sensor may be preconnected to one or more components of the sensor electronics or even all of the sensor electronics. If the analyte sensor system employs a sensor interface such as the sensor interposer 402 shown in the embodiment of FIG. 4, then the sensor may be preconnected to the sensor interface, and possibly one or more components of the sensor electronics as well. Alternatively, instead of treating the pre-connection process as part of the sensor manufacturing phase, it may be identified as a separate phase that occurs before or after the sensor manufacturing phase.

The sensor manufacturing phase may be further divided into a wire cutting phase, a wire coating phase, a wire baking phase, a wire skiving phase, and so on.

In addition to, or instead of the sensor interposer, the components of the sensor electronics that may be preconnected to the analyte sensor may include a processor (e.g., processor module 214 in the embodiment of FIG. 2), a memory (e.g., data storage memory 220 in the embodiment of FIG. 2), a potentiostat (e.g., potentiostat 210 in the embodiment of FIG. 2), an analog measurement circuit, a digital measurement circuit, and/or a transmitter (e.g., telemetry module 232 in the embodiment of FIG. 2).

Figure 9:
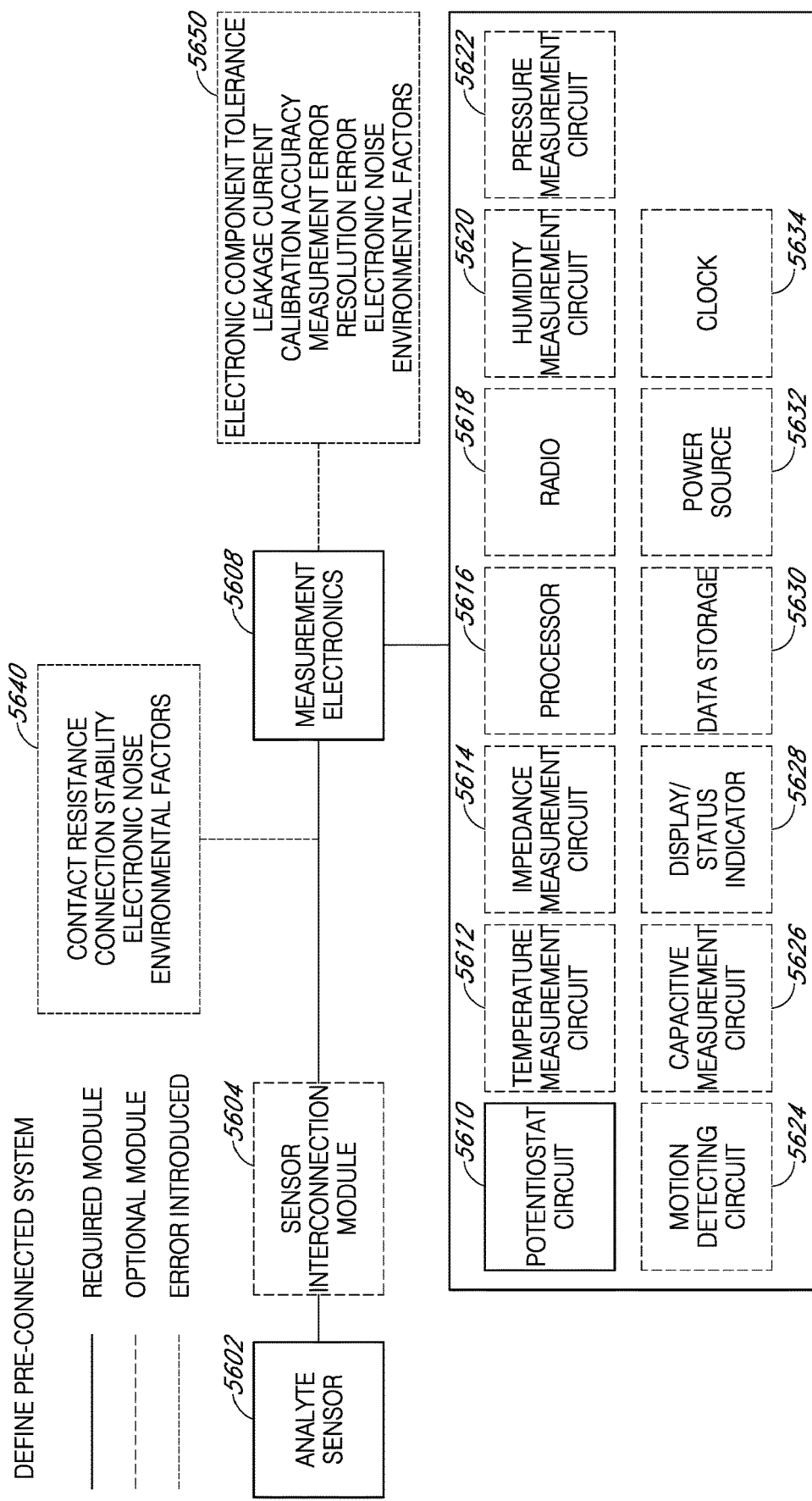
FIG. 9 shows a schematic block diagram of one particular example of a preconnected analyte sensor system

FIG. 9 shows a schematic block diagram of one particular example of a preconnected analyte sensor system that includes an analyte sensor 5602, a sensor interconnection module 5604 (e.g., the sensor interposer) and measurement electronics 5608. The measure electronics 5608 include a potentiostat 5610 and a number of optional components. The optional components may include any one or more of the following: a temperature measurement circuit 5612, an impedance measurement circuit 5614, a processor 5616, a radio 5618, a humidity measurement circuit 5620, a pressure measurement circuit 5622, a motion detector circuit 5624, a capacitive measurement circuit 5626, a display/status indicator 5628, a data storage 5630, a power source 5632 and a clock 5634.

FIG. 9 also shows potential sources of error 5640 and 5650 that may be reduced or eliminated by using a preconnected analyte sensor system. These sources of error may include, for example, errors that may arise when a user is required to connect the sensor to the transmitter or other electronics such as the contact resistance, connection stability, electronic noise and environmental factors. In addition, FIG. 9 shows various errors in the measurement electronics that may be reduced or eliminated by use of a preconnected analyte sensor system. These errors may include, for example, the tolerance of the electronic components, leakage current, measurement error, resolution error, electronic noise and environmental factors that impact the electronics.

Figure 10:
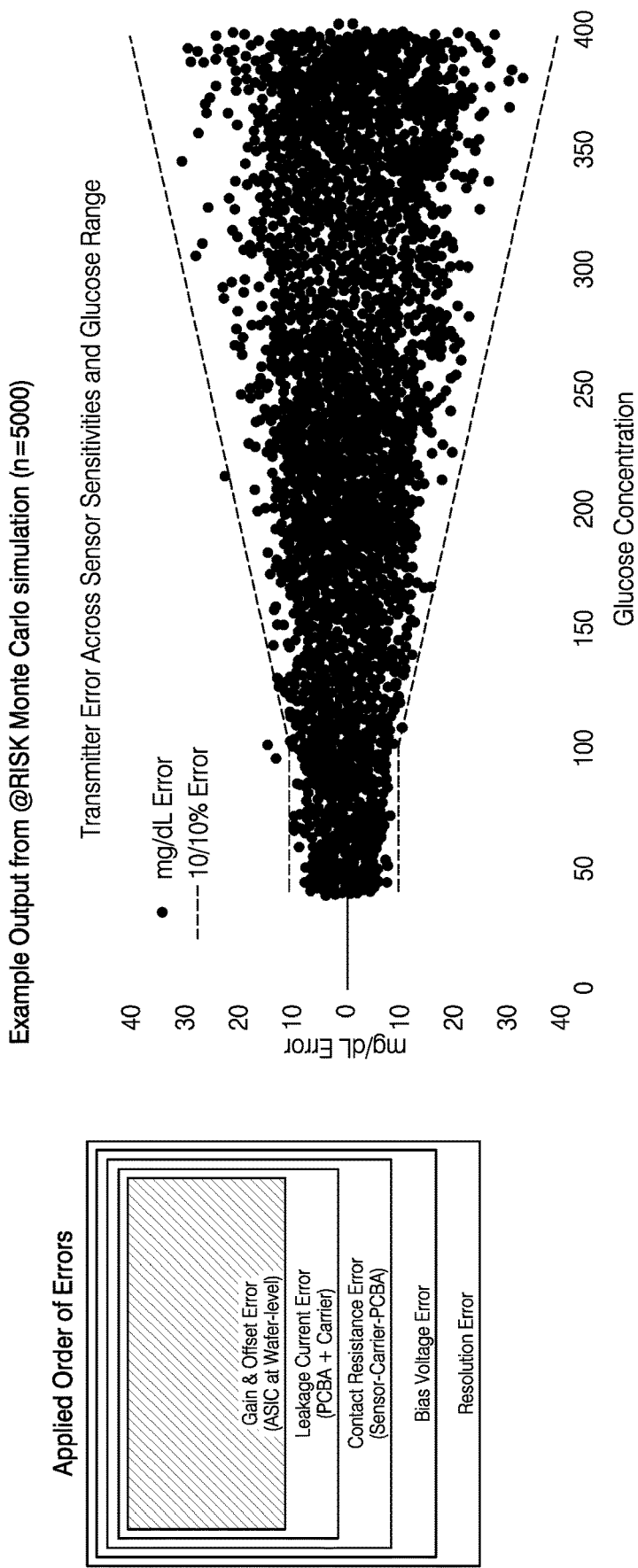
FIG. 10 is a Monte Carlo simulation of 5000 samples using a randomly selected number within the statistical distribution of the input variables that compares a non-preconnected system and a preconnected system.

FIG. 10 is a Monte Carlo simulation of 5000 samples using a randomly selected number within the statistical distribution of the input variables that compares a non-preconnected system and a preconnected system. This shows the number of samples falling within the 10 mg/dL or 10% glucose concentration error target. It shows a reduction of the statistical distribution in error that can be achieved with a preconnected system versus a non-preconnected system in which a variety of individual components having a distribution in their characteristics (e.g., gain, offset, contact, etc.) are combined into a system.

The comparison uses a unitless measurement of current (counts) and calibrates to a known glucose calibration solution. This is an exemplary model and not all variables that affect the system are taken into account. The variation induced by component and measurement variations are eliminated. In particular the values of gain and offset are not measured and calibrated to a unit value so their induced error is eliminated. The system is calibrated with the exact components that influence the values of contact resistance, leakage current and bias voltage. Therefore, their variability is eliminated and they can be modeled as fixed values.

In some embodiments some of the electronics may be incorporated in the interposer or other interconnect component that is connected to the sensor. In this way by pre-connecting the interposer to the sensor, some or all of the electronics will also be preconnected to the sensor. This would allow calibration and other data to be conveniently stored during the manufacturing process. In some embodiments the interposer (or other component connected to the sensor) may be used for other purposes as well. For instance, it may be used to store a code that can be used to track the sensor during manufacturing and/or other life phases of the sensor. The code may be embodied, for instance, in a series of resistors that are printed on an interposer or the like. The code may be programmed by laser cutting selected traces to impart a final resistance to or on the printed resistor. The resistance may be read out by the transmitter when the transmitter is installed via spring contacts or the like on the interposer.

In some embodiments any of these or other components that may be preconnected to the analyte sensor may be configured so that the connection is maintained through multiple periods during a sensor lifecycle. In this way the pre-connection may be maintained throughout the entirety or multiple sequences of the analyte sensor's lifecycle. Hence, the system-level calibrations (i.e., the analyte sensor and the preconnected components of the sensor electronics) that are performed over the analyte sensor's and/or sensor electronics lifecycle should correlate to changes in the system during one or more phases.

The components to which analyte sensor is preconnected may be packaged along with the analyte sensor in the sterile package that is used to ship and store the analyte sensor. Accordingly, in these embodiments it may be advantageous if the preconnected components are single-use, disposable components.

Parameters that may uniquely impact the analyte sensor sensitivity during the manufacturing phase may include, without limitation, parameters such as the materials used to fabricate sensor membrane, the thickness of the sensor membrane, the temperature at which the sensor membrane was cured, the length of time the sensor was exposed to a particular coating solution, the enzyme activity level, amount of coating applied, etc. Parameters that may uniquely impact the analyte sensor sensitivity during the packaging phase may include, without limitation, the sterilization dosage, sterilization method, enzyme activity, packaging material, etc. Additional parameters that may impact the analyte sensor sensitivity during any and all phases may include various environmental parameters such as temperature and humidity and the duration of time at which the sensor was exposed to the measured values of temperature and humidity, for example.

Figure 11:
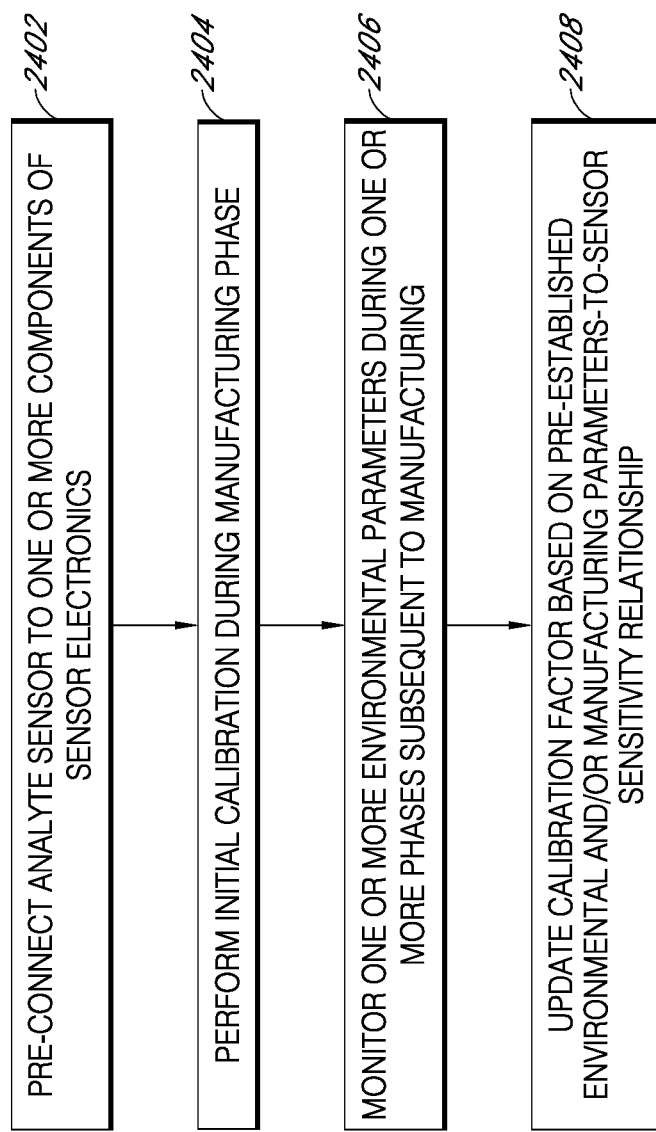
FIG. 11 shows an example of an automatic calibration process that may be performed by the sensor electronics in the analyte monitoring system without user intervention.

In some embodiments the analyte sensor may be calibrated based on measurements of one or more of the various parameters that impact the analyte sensor sensitivity during two or more phases of the analyte sensor lifecycle. An illustrative calibration process 2400 in accordance with some embodiments will now be discussed with reference to FIG. 11. The calibration process may be performed by the sensor electronics in the analyte monitoring system, without user intervention, thereby avoiding the need for external user calibration when the device is in use. The process begins at block 2402 when the analyte sensor is preconnected to one or more components of the sensor electronics during, e.g., a manufacturing phase. Next, at block 2404, the analyte sensor, along with the preconnected sensor electronic component(s), undergoes an initial calibration process. The initial calibration process may use any available a priori information comprising sensor sensitivity information in order to obtain a calibration factor that can be used to convert sensor data (e.g., in units of current or counts) into estimated analyte values (e.g., in unit of analyte concentration).

A number of advantages may arise from performing the initial calibration process after the analyte sensor has been preconnected to the one or more components of the sensor electronics. Measurements may be taken during the manufacturing process phase to establish reference values for comparison at a later time period. These reference values may be used by a processing algorithm to quantify scale and offset values from a known state. In some cases the reference measurement value is dependent on a sensor characteristic that is influenced by a connection property. This may enable a measurement to be taken that would not be possible in a separable system. For instance, errors that may separately arise in the analyte sensor and the sensor electronics may be reduced or eliminated by calibrating them as a single unit. In addition, errors that may arise from the act of connecting (and disconnecting) the analyte sensor to the sensor electronics can also be reduced or eliminated. For example, the impedance measurement of the sensor may be more stable if the sensor remains continuously connected to the sensor electronics.

After preconnecting the analyte sensor to one or more components of the sensor electronics, the calibration process 2400 proceeds to block 2406 where one or more environmental parameters affecting sensor sensitivity are monitored during one or more phases of the analyte sensor lifecycle subsequent to the manufacturing phase. For instance, environmental parameters may be monitored during the sensor packaging stage, sensor package sterilization phase, sensor shipping stage, sensor storage stage, sensor insertion stage and/or the sensor use stage.

The monitoring of the environmental parameters may be accomplished in any number of different ways. For instance, if the analyte sensor is preconnected to at least the components of the sensor electronics that are used to apply a stimulus signal to an analyte sensor and measure a signal response to the stimulus signal, the signal response can be used to determine an impedance value of the analyte sensor. Various techniques for calculating analyte sensor impedance values based on the signal response are described elsewhere herein, such as one or more of the techniques discussed in U.S. patent application Ser. No. 14/144,343, published as US-2014-0114156-A1 and entitled "Advanced Analyte Sensor Calibration and Error Detection," which is hereby incorporated by reference in its entirety. The determined impedance may then be compared to a pre-established impedance-to-environmental parameter relationship such as a pre-established impedance-to-temperature relationship, a pre-established impedance-to-humidity relationship, or a pre-established impedance-to-membrane damage relationship, as also discussed in the aforementioned patent document. In this way, the environmental parameter(s) may be monitored.

In an alternative embodiment, the environmental parameters may be monitored using an environmental sensor such as a temperature monitor or a humidity monitor. For instance, such monitors may be incorporated into the sterile package in which the analyte sensor is stored when it leaves the factory. Alternatively, the monitors, such as the temperature monitor, may be directly incorporated into the sensor electronics themselves. In some cases the monitors need not provide a numerical value for the environmental parameters, but may simply indicate if the environmental parameter has fallen outside of specified ranges within which the sensitivity of the analyte sensor is known to remain relatively stable. In this way a relatively simple environmental monitor may be employed.

Once the manufacturing and environmental parameter(s) has been obtained, the calibration process 2400 proceeds to block 2408 where an updated calibration factor is determined based on a pre-established environmental and/or manufacturing parameters-to-analyte sensor sensitivity relationship. In determining the updated calibrated factor, information in addition to the measured parameter(s) may be taken into account. For instance, the initial calibration factor may be used as well. The updated calibration factor may be used to properly calibrate the analyte sensor so that sensor data (e.g., in units of current or counts) can be converted into analyte values (in units of analyte concentration).

The updated calibration factor may be determined at any suitable time after the environmental parameters have been obtained. In part, this will depend on the particular components of the sensor electronics that have been preconnected to the analyte sensor. For example, if the preconnected components include a suitable processor and associated memory and a power source (e.g., a battery), then the updated calibration factor may be determined as soon as the environmental parameters are obtained e.g., while in the sterile package or while in storage. Alternatively, if such a processor is not available, the environmental parameters may be stored in one of the preconnected components and communicated when the remainder of the sensor electronics are connected, such as when the sensor insertion phase is initiated. Alternatively, if the preconnected components also include a transmitter, then the environmental parameters may be transmitted to the remainder of the sensor electronics or to another connected device.

In some embodiments the updated calibration parameter may be determined by a processor and associated algorithms that are not incorporated in the sensor electronics. Rather, the updated calibration parameter may be stored in the preconnected electronic components and uploaded at a suitable time to a device which with the sensor electronics communicates (e.g., display devices 114, 116, 118 and/or 120 in FIG. 1) or to a cloud-based processor (e.g. cloud-based analyte processor 490 in FIG. 1). The cloud-based processor or other device that calculates the updated calibration parameter then downloads it to the sensor electronics for use in calibrating the analyte sensor.

As previously mentioned, environmental parameters may be obtained at multiple times during the various phases of the analyte sensor lifecycle and even at multiple times during a single phase (e.g., storage). The environmental parameters obtained at each of these different times may then be used, potentially in combination with other factors (e.g. lot factors, in vivo measured values, cloud data, time since sensor manufacture, individual patient factors) to determine a final updated calibration factor.

In some embodiments instead of, or in addition to, periodically updating the calibration factor at multiple time during the various lifecycle phases, a single complex adaptive calibration factor may be generated during the sensor use phase. The complex adaptive calibration factor may combine an initial calibration factor obtained during sensor manufacture with environmental conditions experienced by the analyte sensor (and any preconnected electronics, if present) from sensor manufacture to sensor insertion. In this way the experience of the analyte sensor during its lifetime is encoded in a form that allows it to be used by the calibration algorithm. Thus, instead of separately accounting for each individual environmental parameter such as temperature and humidity and sensor characteristics such as impedance, a single encoded value or profile may be provided to the calibration algorithm that encapsulates all the manufacturing and/or environmental parameters and sensor characteristics.

Figure 12:
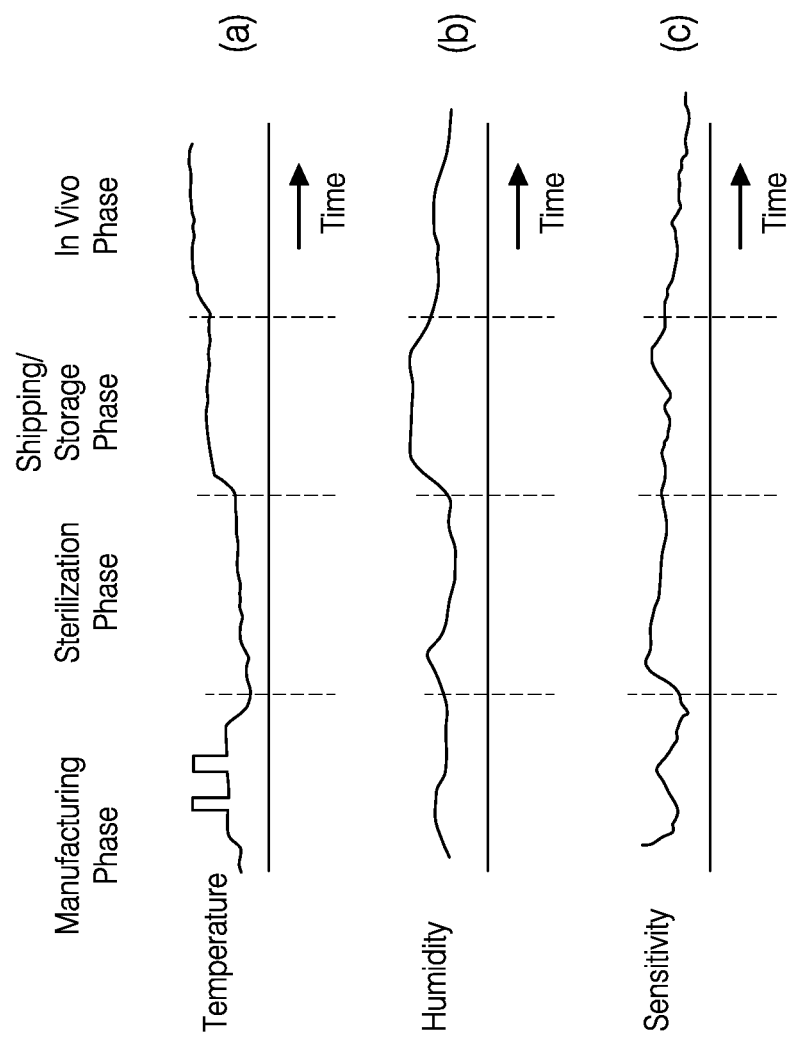
FIG. 12 includes timelines showing the monitored temperature (a), humidity (b) and sensitivity (c), respectively, over various phases over the lifetime of an analyte sensor.

FIGS. 12(*a*)-12(*c*) are timelines showing various phases over the lifetime of an analyte sensor. This example shows a manufacturing phase, a sterilization phase, a shipping/storage phase and an in vivo stage. The monitored temperature and humidity experience by the sensor over these phases is shown in FIGS. 12(*a*) and 12(*b*), respectively, and FIG. 12(*c*) shows the changes in the analyte sensor sensitivity that are determined based on these environmental parameters. The spikes in temperature that are shown during the manufacturing stage arise during the curing of the analyte sensor. It should be noted that the sensitivity may not appreciably change when the spikes are relatively small and/or short in duration, and thus not all such spikes will require re-calibration of the analyte sensor. Other spikes that are larger in magnitude and/or duration do lead to sensitivity changes, thus indicating that re-calibration may be required when the spikes exceed these thresholds. Accordingly, environmental parameters such as temperature and humidity may only need to be monitored to determine if they exceed or fall below certain thresholds which have been shown to significantly affect the sensitivity.

It should be noted that all of the parameters mentioned above which impact the sensitivity of an analyte sensor and which are monitored at various points in time may also impact the baseline signal of the sensor. Accordingly, in addition to monitoring these parameters to calibrate or otherwise adjust the sensitivity of the analyte sensor, these parameters may also be monitored to calibrate or otherwise adjust the baseline of the analyte sensor. More generally, the monitored parameters may be used to adjust any characteristic metric of the analyte sensor and not just the sensitivity and/or the baseline. Examples of such characteristic metrics include, without limitation, long term drift, analyte sensor current, rate of exponential drift, ratio between fast and slow components in a dual-exponential sensitivity model, non-glucose baseline, compartmental bias between glucose concentration in local tissue surrounding the sensor and the blood glucose, constant baseline, asymptotic magnitude of baseline rise due to membrane degradation, asymptotic magnitude of baseline rise due to membrane degradation, onset/transition time of baseline rise due to membrane degradation, drift rate of baseline rise due to membrane degradation, initial magnitude of fast electrochemical break-in, drift rate of fast electrochemical break-in, initial magnitude of slow electrochemical break-in, drift rate of slow electrochemical break-in. initial magnitude of compartmental bias, final magnitude of compartmental bias and drift rate of the disappearing compartmental bias.

The previously mentioned complex adaptive calibration factor may be determined in part using predetermined statistical correlations that have been identified between sensor behavior while in use and sensor behavior that was measured during the various phases of the analyte sensor lifecycle for a large number of previously deployed sensors. That is, instead of simply using pre-established environmental and/or manufacturing parameters-to-analyte sensor sensitivity relationships to calibrate a particular sensor, a relationship between one or more of the characteristic metrics of a large sampling of sensors that are measured at various points in time and the resulting sensitivity or other characteristic metrics of the sensor samples during the use phase may be used to develop the complex adaptive calibration factor.

Figure 13:
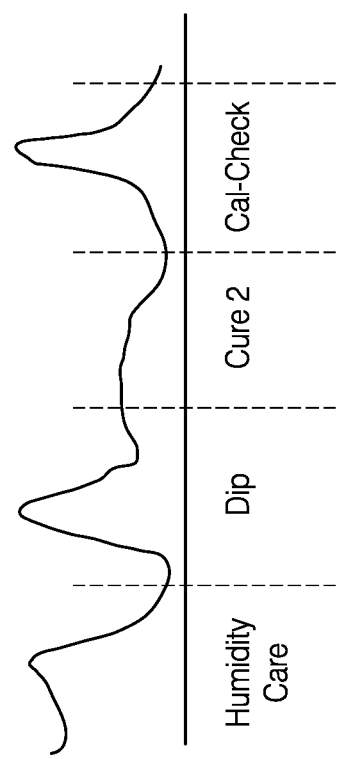
FIG. 13 shows a sensor output signal obtained from an analyte sensor during various steps during the manufacturing process.

For example, FIG. 13 shows a sensor output signal obtained from a sensor during steps of the manufacturing process, including at least one cure step, a membrane application step during which the sensor is coated in a particular membrane, and a manufacture calibration measurement step to determine an initial or in vitro value of analyte sensitivity, baseline, interferent sensitivity, impedance value, etc. As shown, the sensor output signal varies during each step. The shape of this signal over all or some of these steps defines a sensor signature that may be obtained for a large number of sensors during the manufacturing phase. By examining the behavior of these sensors during subsequent phases, particularly during the use phase, statistically useful correlations may be found between the sensor signature and sensor behavior. In this way by measuring the sensor signature of a particular sensor during the various steps of the manufacturing phase it may be possible to predict its behavior (e.g., one or more of the characteristic metrics) at a later time. For instance, it may be possible to obtain a predicted sensitivity profile of sensitivity change over time for a particular sensor.

While the preceding discussion has focused on the use of the manufacturing and/or environmental parameters monitored during various lifecycle phases of an analyte sensor to facilitate calibration of the sensor, these monitored parameters may also be used for other purposes as well. For instance, based on the monitored parameters various actions may be taken by analyte monitoring system. For instance, if one or more of the environmental parameters exceeds a specified threshold for a certain period of time, a message may be generated on a receiver (e.g., a user's mobile communication device) indicating to the user, for instance, that the expected end of life of the sensor has been reduced, or that the quality of the calibration is below some recommended value or that that the confidence level in the sensor reliability is below some recommended value, or that the sensor is only suitable for certain operating modes (e.g., sensor life, accuracy, insights, trends, analyte value, alarms, monitoring type 1 diabetic patients but not type 2 diabetic patients, or vice versa, or that the sensor is only suitable for implantation at certain sites such as the abdomen or arm). Alternatively, or addition thereto, other actions that may be performed as a result of monitoring the environmental parameters may include adjusting various startup parameters of the analyte monitoring system (e.g., requiring a longer than normal break-in period for the sensor), switching to an operating mode in which glucose levels are only reported as being in a range (e.g. low, medium or high) instead of an operating mode in which glucose concentrations are reported, initiating an in vivo calibration process, using a default calibration value, and using a temperature, humidity and/or complex compensated calibration value.

The reduction in errors that can be achieved by calibrating a preconnected system in comparison to a conventional (non-preconnected) system have been modeled by taking into account a subset of the variables that affect the system. The model only uses a unitless measurement of current (counts) and calibrates to a known glucose calibration solution. The variation induced by component and measurement variation are eliminated. In particular, the values of gain and offset are not measured and are calibrated to a unit value so that their induced error is eliminated. The system has been calibrated with the exact components that influence the values of the contact resistance, leakage current and vias voltage. Therefore their variability is eliminated and they can be modeled as fixed values.

Hierarchical Models for Sensor Manufacturing Process, Sensor Bench Characterization, and in Vivo Performance In one variant of the subject matter described herein, statistical processes may be employed as part of the closed-loop feedback manufacturing process.

It has been found that the sensor manufacturing process, sensor bench characterization, and in-vivo sensor properties are all loosely tied with each other. That is, while sensor process parameters may be monitored to ensure they are within limits and each sensor is then evaluated to determine if it meets the predefined criteria, process parameters and in vitro properties are not highly predictive of sensor in vivo properties (e.g., sensitivity). Typically, in vivo properties are estimated less from manufacturing process variables and more from calibration, since in a conventional system each sensor is generally calibrated every 12 hours or so with a blood glucose meter.

When automatic calibration techniques are employed it may become necessary to rely more and more on sensor characteristics and less on calibration through meters and the like. Thus, the mathematical relationship between manufacturing process variables, sensor in-vitro (or bench) characteristics and in-vivo properties becomes important. In addition, as the number of sensors being manufactured increases, the necessary resources and time may not be available to exhaustively test each sensor for pass/fail criteria or to estimate their in vitro properties. A mathematical/statistical framework could thus provide an alternative way for relating the sensor manufacturing process with sensor in vitro sensitivity and expected in vivo sensitivity. Ideally, process variables can be set to produce sensors with specific sensitivities.

There are a number of sensor process and design parameters that may be adjusted to build sensors with specific properties. These include relative humidity, temperature, cure time, dip time, layer thicknesses, and raw material properties/proportions. The behavior of sensors in vitro and in vivo depends on these process variables and may be modeled using mathematical and statistical models. Hierarchical models are a type of multi-level statistical model where different random effects that impact processes and measurements are quantified in multiple levels as conditional probabilities. For example, the variability of the process at specific set points may be modeled in level 1 (highest level), the variability of sensor behavior in vitro at level 2, and variability of sensors in vivo at level 3. The model eventually may relate these levels so that variables from one level (e.g., second or third) can be used to estimate variables in a different level (e.g. level 1).

One example of a framework for a hierarchical model for sensor manufacturing and in vivo properties is described below, where:

Xp represents process and design parameters, such as relative humidity, temperature, curing time, dip time, layer thickness, raw material characteristics, etc.

Mp is a vector of target sensor properties defined by the process parameters (Xp)

$$Mp=N(f(Xp),\Sigma^2)$$

That is, sensor properties are a function of all of the sensor design and process parameters. The overall distribution of sensor properties has a mean of process set-point or target with a variance of $\Sigma 2$. Note that non-normal distributions are also possible.

The vector of sensor properties that are verified on the bench is:

$$Mb=N(Mp,\Gamma^2)$$

For example, if a lot of 10,000 sensors is manufactured, 100 of them may be sampled to estimate process properties. So the distribution of bench verified properties is normal with a mean target lot Mp and a variance of $\Gamma^2$.

$$Mi:N(g(Mb),V^2);$$

These are the actual in-vivo properties of the sensor. The distribution of the sensors is described by a function 'g' that translates the in-vitro properties into in-vivo. This is also referred to as in-vivo to in-vitro correlation. A simple example of the function 'g' is a proportionality constant from in vitro to in vivo. In a general case the function 'g' is a transformation from in vitro to in vivo with multiple factors. In a matrix form this may be written as:

$$Mi=G*Mb,$$

where G may have factors for sensitivity, drift, and baseline and interdependencies.

$$G = \begin{bmatrix} s & s\_d & s\_b \\ s\_d & d & 0 \\ s\_b & 0 & d \end{bmatrix}$$

where the diagonal terms s, d, and b are sensitivity, drift, and baseline related in vitro to in vivo factors, while the off-diagonal terms are the cross-correlations between sensitivity and drift s_d, and sensitivity and baseline s_b. The elements of the matrix may be time-varying.

Once this model is developed there are various multiple applications in which it may be employed. In one application, process information may be incorporated into a continuous glucose monitor (CGM) algorithm (i.e., a joint probability algorithm), thus enabling reduced and factory calibration, as described in US-2014-0278189-A1, entitled "Advanced Calibration for Analyte Sensors", incorporated by reference in its entirety. In another application, given that large scale sampling of the manufacturing process is cumbersome and expensive, this hierarchical model may be used to estimate the process parameters and target sensor properties through sampling of multiple lots from in vitro and in vivo. A third application involves the tracking of field performance and directly correlating it with manufacturing. The model may help proactively track process parameters based on field data, allowing corrective actions to be taken more rapidly.

Estimating Sensor Properties for Longitudinal Field Data

In another variant of the subject matter described herein, sensor properties such as sensitivity may be estimated from field data. For example, predictive models may be created by mapping manufacturing parameters to in vivo sensor behavior from very large datasets (assuming the sensors have unique sensor IDs to trace the field data to the manufacturing data).

Sensor sensitivity is typically estimated by comparing sensor current to reference glucose measurements. However, this becomes difficult or impossible when field data either has no reference glucose measurements for comparison (i.e. for a factory calibrated product) or when reference glucose measurements are unreliable (e.g. if the meter is of poor or unknown quality and reference measurements are not trustworthy). This problem can be addressed as follows.

Individual users may have stable glucose dynamics across several weeks or months, assuming they are consistent with their therapy approach and their underlying physiology is not changing dramatically. As a result, observed differences in raw sensor signal statistics (e.g. mean, standard deviation, median, percentiles, skewness, etc.) from sensor to sensor may reveal differences in sensor properties such as sensitivity. Although sensitivity estimated in this way may not be as reliable as sensitivity measured through comparison with accurate reference glucose measurements, with sufficiently large datasets the information may be useful for detecting patterns in sensor behavior and be used to construct predictive models of field sensor behavior or detect unexpected shifts in field sensor behavior.

For example, when a wire is obtained from a new wire vendor is introduced to production, it generally is not anticipated to have any impact on sensor sensitivity. However, field data shows that across thousands of users, standard deviations of raw sensor readings are, e.g., about 2% higher, in sensors from lots using the new wire vendor than the historical standard deviations for each user. This pattern could trigger further investigation into the impact of the wire vendor, or the data could be incorporated into factory calibration models. In this way the predicted sensitivity in the factory calibration algorithm can be adjusted to account for the impact of the wire vendor, leading to improved accuracy.

NMR Method to Characterize Carbosil/PVP Ratio in Diffusion Resistance Layer Solution In yet another variant of the subject matter described herein, which may be used to improve the accuracy of sensors during manufacturing, a method may be employed to characterize the Carbosil/PVP ratio in the diffusion resistance layer of the sensor.

The diffusion resistance layer is one the most important layers in the CGM membrane of the sensor, which provides stable, predicable glucose and oxygen permeation and blocks some interference agents. Currently, certain sensors use a Carbosil 2090A and PVP (K90) blend system. Carbosil dissolves in THF but is not able to be dissolved in ethanol. However, PVP can be dissolved in ethanol but not in THF. So the current diffusion resistance layer solutions are prepared by using a THF/Ethanol mixed solvent to dissolve both Carbosil and PVP.

Sensor performance is related to the Carbosil/PVP ratio (e.g., a high PVP will yield high sensitivity). In particular, the uniformity of the dip coating will be affected by Carbosil/PVP ratio. Also, the diffusion resistance layer dipping solution viscosity will be affected by Carbosil/PVP ratio change. Overall, sensor stability will be affected by Carbosil/PVP ratio.

In order to make reproducible sensors, a consistent, accurate Carbosil/PVP ratio in the RL dipping solution is an important parameter to control. However, up to now, no method has been developed to evaluate the Carbosil/PVP ratio in an RL solution. Thus, in order to improve sensor accuracy and thus enhance the ability of automatic calibration, it is important to track the quality of each RL dipping solution before the sensors are dipped.

In one aspect, nuclear magnetic resonance (NMR) spectroscopy is used to determine the Carbosil/PVP ratio in the diffusion resistance layer solution. In particular, proton NMR technology may be employed.

One particular example of a process that may be employed to determine the Carbosil/PVP ratio is described by the following steps:
1. Prepare sample
   1.1 C2090A/PVP THF/EtOH solution with 22 wt. % EtOH, 13.6 wt. % of PVP.
   1.2 Cast a film using RL solution and dry at 50 C overnight till a consistent weight achieved. Remove solvent.
   1.3 Cut a piece of thin film and dissolve in DMSO-d6 with concentration of 10 mg/mL. (20 mg/mL, 50 mg/mL)
2. Run proton NMR and obtain FID signal followed by a baseline correction, tune phase and obtain spectra.
3. Integration of MDI peaks in Carbosil; calculate integration number of each proton.
4. Integration of H2 peaks in PVP; calculate integration number of each proton.
5. Calculate mole ratio Carbosil and PVP
6. Obtain calibration curve of Carbosil/PVP blend.
7. Calculate Carbosil/PVP wt. %/wt. % ratio based upon calibration curve.

Figure 14:
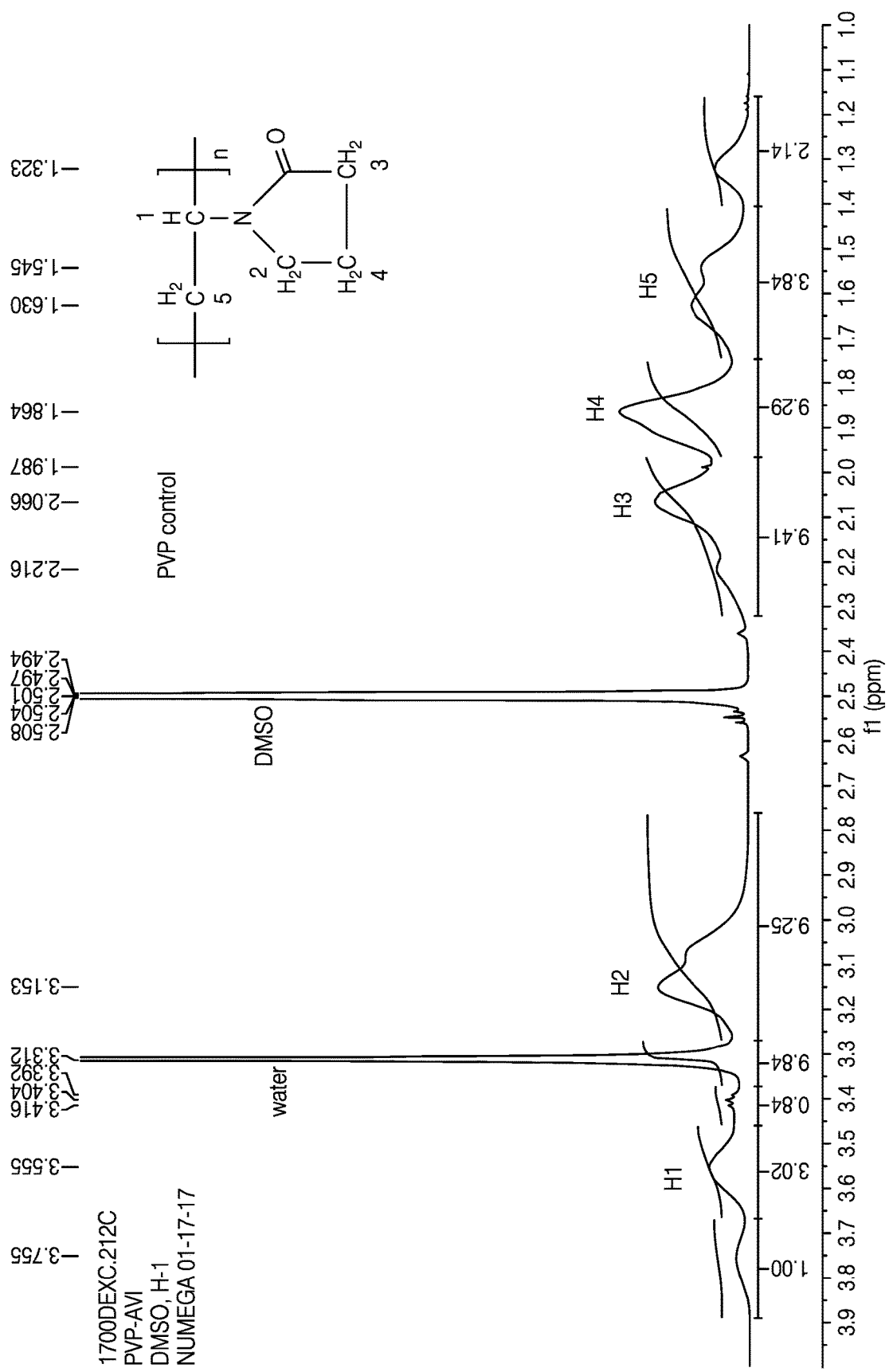
FIG. 14 shows the NMR spectrum of PVP in DMSO-d6.
Figure 15:
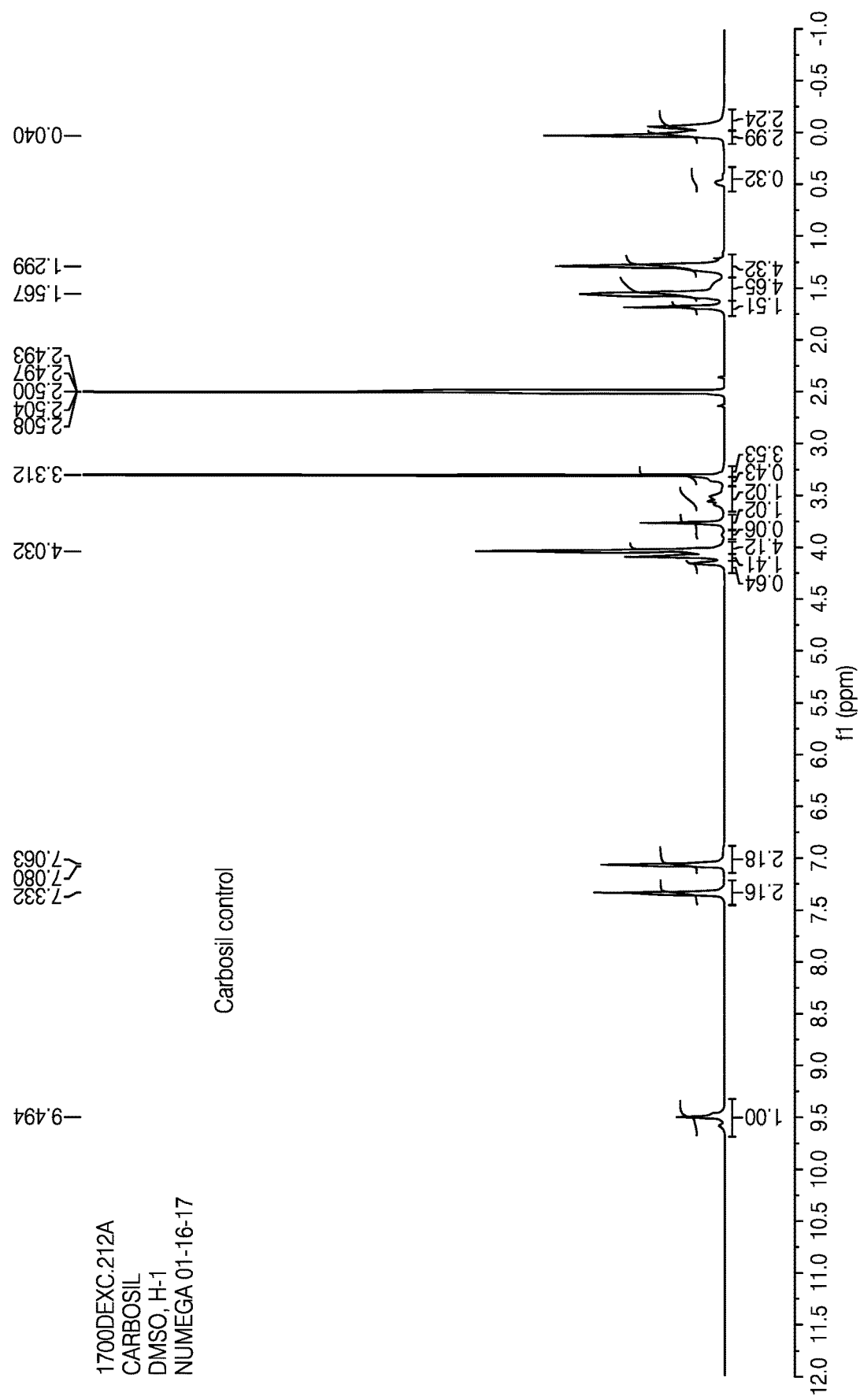
FIG. 15 shows the HNMR spectrum of Carbosil in DMSO.
Figure 16:
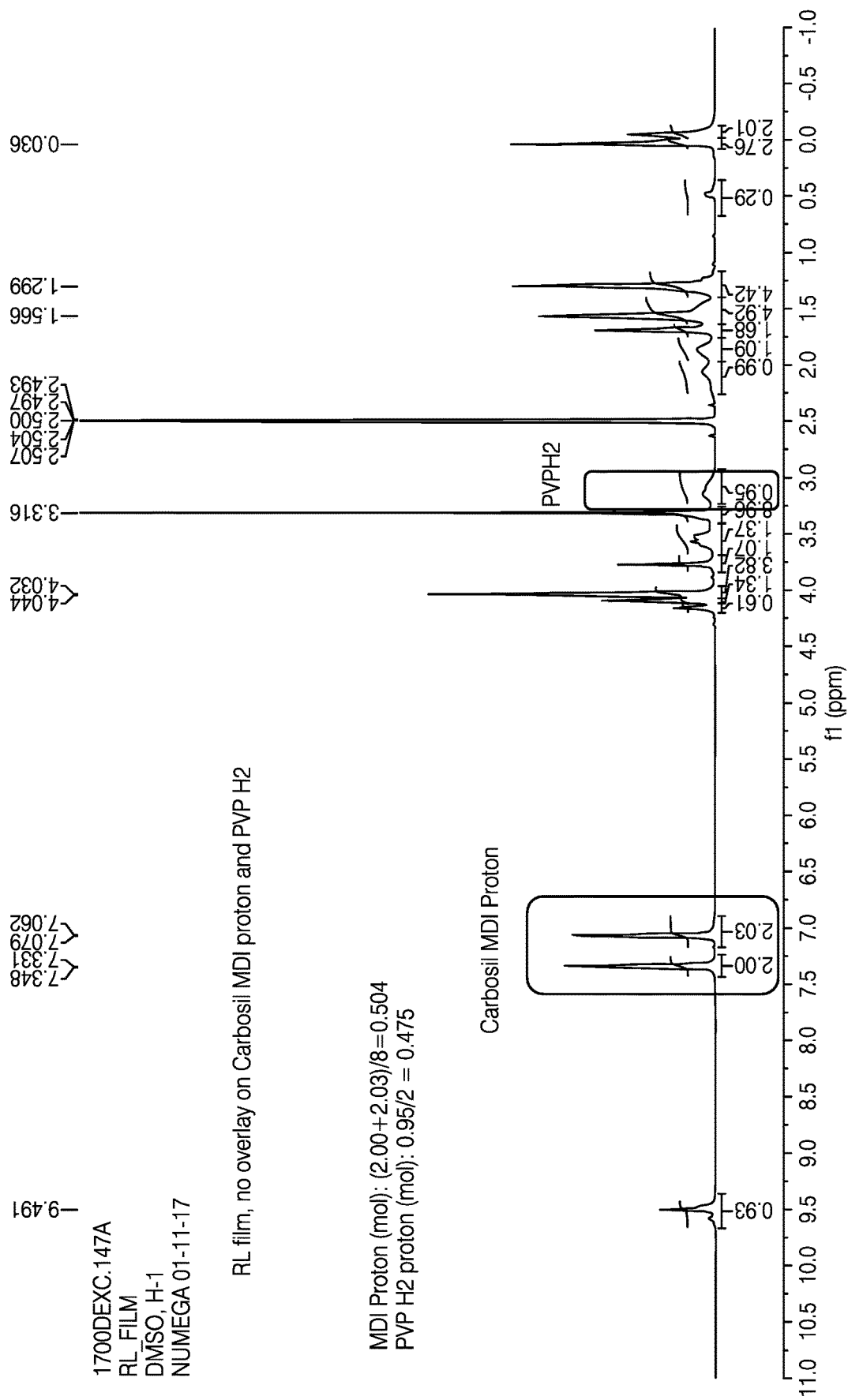
FIG. 16 shows the HNMR spectrum of an RL film (Carbosil/PVP blend with removal of solvent).

FIG. 14 shows the NMR spectrum of PVP in DMSO-d6. FIG. 15 shows the HNMR spectrum of Carbosil in DMSO. FIG. 16 shows the HNMR spectrum of an RL film (Carbosil/PVP blend with removal of solvent). The MDI peak in Carbosil and the H2 peak in PVP were selected to calculate the Carbosil/PVP ratio.

Figure 18:
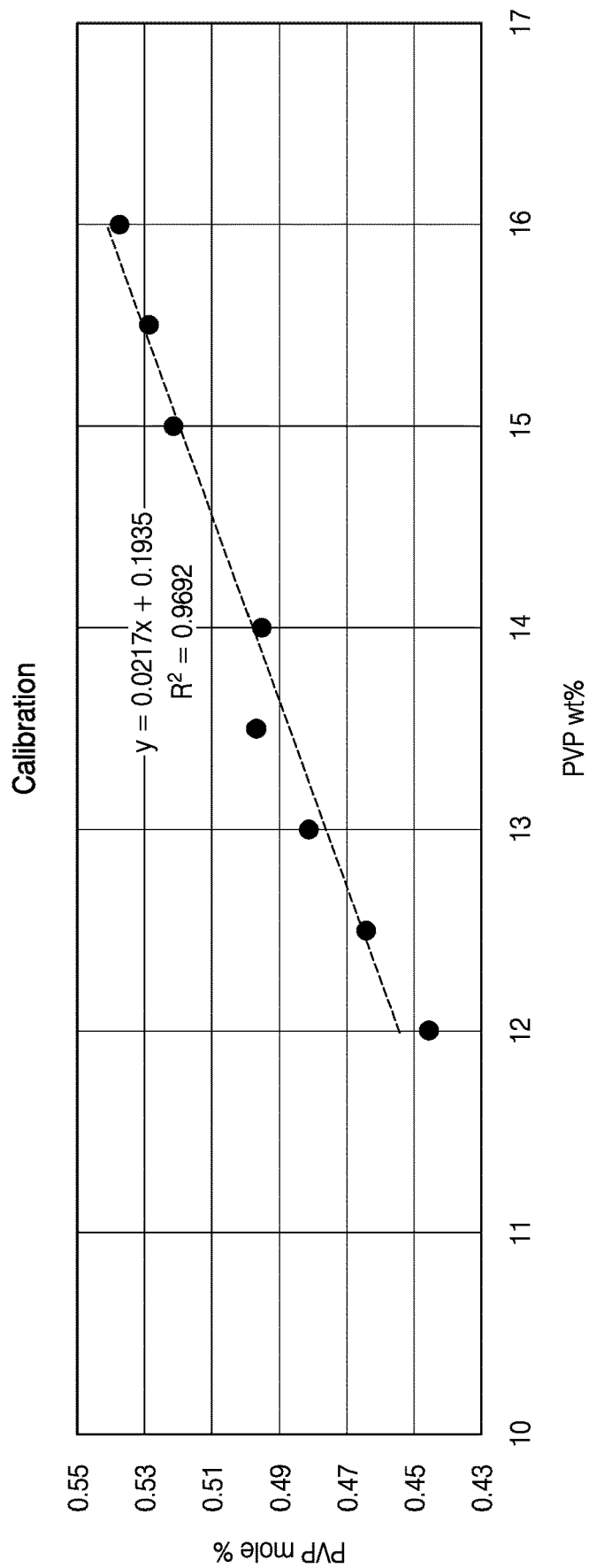
FIG. 18 shows an HNMR calibration curve.

An HNMR Calibration process was conducted to validate the method. First, an RL solution with different Carbosil/PVP ratio with a predetermined Carbosil/PVP ratio was prepared as shown in the Table shown in FIG. 17. Then, H NMR was run using DMSO-d6 as the solvent. FIG. 18 shows the resulting HNMR calibration curve.

Temperature and Humidity Sensing During Storage

As discussed above, impedance measurements of the analyte sensor may be obtained during the shipping and storage phases to monitor humidity for a sensor preconnected to electronics. In addition, the temperature sensor in the transmitter could record the temperature and thus the temperature and humidity sensors could indicate if the analyte sensor was outside its recommended humidity and temperature during shipping and storage. In addition, an algorithm could be created to compensate the initial factory calibration parameters based on the temperature and humidity conditions and the duration of exposure. (It should be noted that the initial factory calibration may be performed on a single sensor using a single bath or on a lot or brick of sensors e.g., 30 sensors, which can be simultaneously calibrated using a single large bath).

In one variant, measuring current alone may be sufficient to indicate humidity or extreme humidity. Some embodiments of the sensor system may wake up periodically and perform a measurement to identify when the sensor has a signal to indicate a system start up (due to hydration after deployment). A fully preconnected sensor would also measure current when only humidity is present. Accordingly, it would be a useful indicator indicating that the analyte sensor was exposed to humidity conditions during shipping and storage. If the system is not fully integrated with the electronics, a removable adhesive tab (e.g., a "sticky tab") could be placed on the transmitter's electrodes, which would conduct current when humidity is present. This would allow the transmitter to measure humidity. The tab would be removed before transmitter use.

In another variant the sensor storage conditions may be determined using resistors or other materials that have a known response to temperature, humidity, or a combination of both, and which generate an electrical signature (e.g., resistance, current). In addition to the circuit that causes a transmitter to be activated when it detects a sensor, the same circuit or a separate circuit could be arranged to be triggered whenever the temperature and/or humidity exceeds a threshold. Based on the duration of the trigger and the magnitude of the measurement (reflective of the temperature and/or humidity), the system would be able to adjust the calibration factor to better predict in-vivo performance by inferring changes due to environmental conditions. In one particular implementation, a strip of the environmentally-sensitive material may be placed across the transmitter electrodes so that it only allows current to pass under specific environmental conditions. In some cases this serves as an irreversible circuit or material change that is only triggered above a threshold, creating an on/off indicator to shift the predicted sensor response to a new performance bin or to prevent use of the product if extreme conditions were reached.

In yet another variant, the packaging in which the sensor is stored may include a temperature and/or humidity sensitive material that changes color based on the temperature and/or humidity so that a color change would indicate the storage conditions experienced by the sensor. For instance, in one example the material may be located on the package interior in the form of a small region (e.g., a dot). The color of the material may be detected by a camera or other detector in the mobile device in which the system app is located, which can determine the degree of color change. Alternatively, the color change could be detected directly by the transmitter or other sensor electronics, which as noted above, can be used to better predict in-vivo performance by inferring changes due to environmental conditions.

In yet another variant, the calibration parameters that are used by the calibration algorithm may differ from sensor to sensor based on the sensor manufacturing details and other factors. From the transmitter point of view, the user inserts a sensor and enters the "sensor id" into the display and based on this, the display will either send the actual set of parameters that needs to be used or sends a code that causes one of a predefined set of parameters to be used. To achieve this, the transmitter may store multiple sets of parameters. If the set of parameters is large, storing multiple copies of the parameters may occupy too much storage space.

To address this problem, in some cases only one default set of calibration parameters may be stored on the transmitter and, to obtain an updated set, only the differences between the default set and the updated set need to be sent. Since usually the differences are going to be small, this may be more efficient. This approach also provides the flexibility to change any individual parameter. That is, the set of parameters does not have to be fixed and they can change during the factory calibration process. If the set of parameters is an ordered list, then the changes can be specified as a list of paired values such as (parameter number, new value).

Calibration Code Encoding

In yet another aspect, a sensor calibration code or some other code assigned to the sensor in the factory may be linked to the customer's account in the following manner. In this example the transmitter that is shipped with the sensor is assumed to be re-useable and ships with enough sensors to cover the duration of the transmitter's life (generally determined by its battery). For instance, a transmitter that is usable for three months would need 6 sensors that last 14 days each. In such a system a factory calibration code associated with the sensor may be communicated to the user's mobile device using the following method.

First, at step 1 the customer orders a package of sensors, possibly using a dedicated app on their mobile device. At step 2, while in the factory the package and the sensors to be included therein are scanned to establish a link between the packaging and the sensors. At shipping (step 3), a shipping label with the customer's account information is scanned along with the packaging to thereby create a link between the customer's credentials and the packaging. This link is stored by the manufacturer in a cloud server or the like for future reference.

At step 4 the package with the sensor is shipped to the customer. At step 5 the customer inserts a new sensor and installs the new transmitter and the package initiates a session. After the user initiates the session, at step 6, the sensor code information stored in the cloud server or the like can be retrieved since the package of sensors and the transmitter has been previously linked to the customer's account.

Enhancements to Closed Loop Manufacturing Feedback Process

In another variant, additional information may be used to supplement the information that is available concerning the manufacturing process, which is stored by a sensor that is preconnected to sensor electronics. For example, the manufacturing process typically involves a sequence of steps that are performed at different stations in the factory. In principle the amount of time needed by the operator to perform any given step should be about the same for each part or component that is being assembled or process being performed at that station. Any significantly high variability in these times may indicate an immature station or a process where the operator has to excessively make adjustments to parts and fixtures during assembly, which could highlight areas for process improvements. In some cases a small device may be placed at each workstation to perform a study of the time needed to perform the activity required at that station. The device may include an actuator (e.g., button, motion sensor, light sensor) that provides a simple, unintrusive means by which the operator can quickly interact to allow a microcontroller in the device to record the time for each device interaction. The operator would be instructed to interact with the device every time they complete the task at their station. The device then stores the times, which can be subsequently output for analysis.

Initial Calibration

Figure 19:
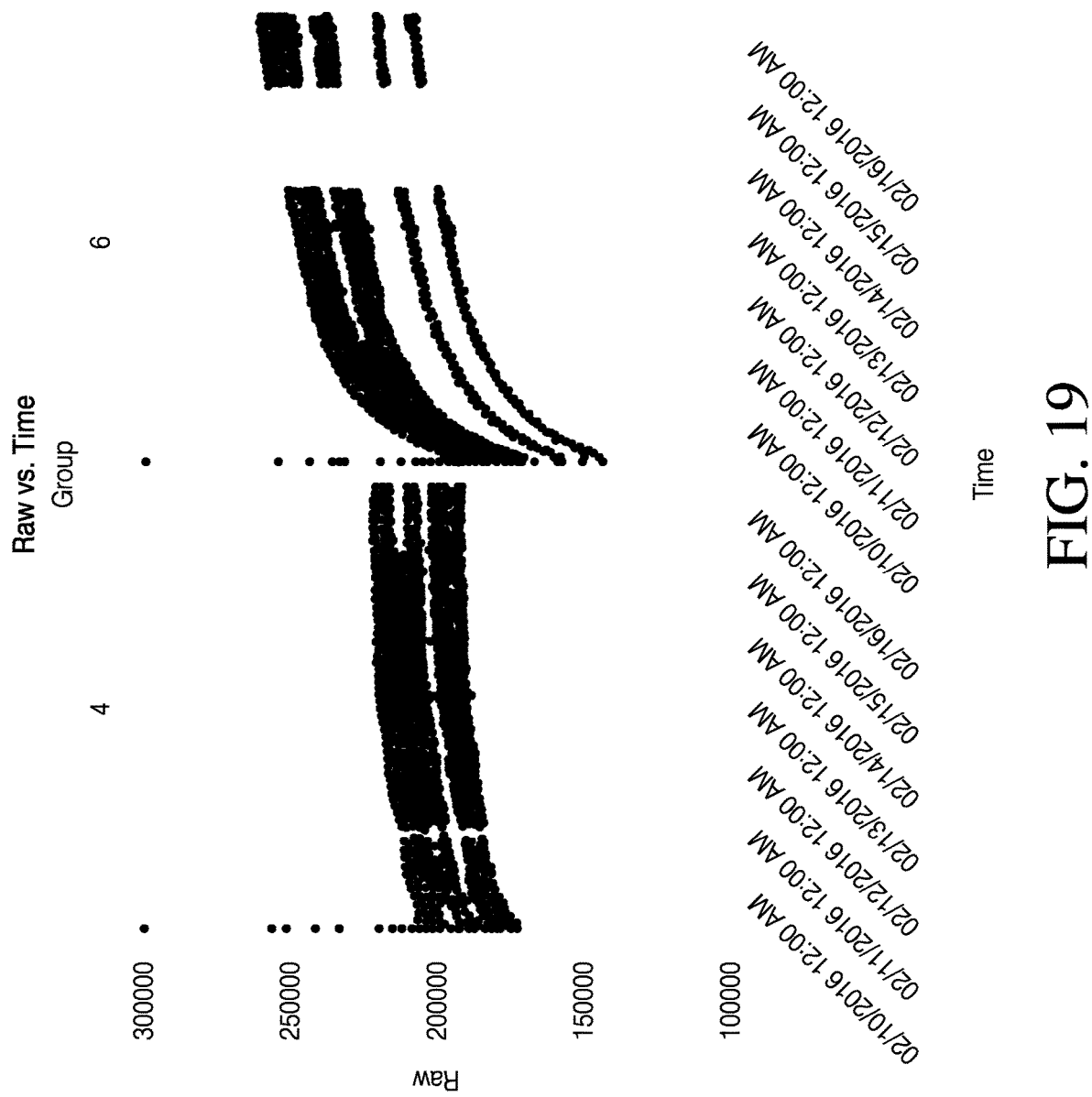
FIG. 19 is a graph showing initial sensor drift when ethylene oxide (ETO) sterilization is employed.

In another variant, when ethylene oxide (ETO) sterilization is employed (instead of e-beam sterilization) the initial drift profiles for some of the conditions are found to be very flat (see the graph of FIG. 19, where group 4 (left) is an ETO condition and group 6 (right) is the unsterile condition using the same timescale with about 12 sensor drift profiles for each group). ETO processing may thus be used to stabilize the sensor against high humidity storage or shipping excursions.

In another variant, sensors may undergo ETO sterilization with a rechargeable desiccant present in the packaging during the ETO process. The desiccant may then be "baked out" after ETO to recharge its desiccating capability. After sterilization in ETO, an additional desiccant may be added to the final sensor packaging and/or the final packaging may employ a moisture barrier to minimize humidity. Several sensors may be sterilized in this manner using bulk packaging that contains the sensors and the desiccant.

Communication of Sensor Parameters via NFC

In yet another variant, sensor information (e.g., sensor parameters, calibration factors or codes, environmental characteristics) of the type described herein that is to be communicated may be sent from the sensor to the transmitter via an NFC protocol. In one embodiment, this may be accomplished by providing the sensor base or interposer with an NFC tag and providing an NFC reader on the receiver (e.g., a user mobile device). The sensor information received by the receiver from the sensor base or interposer can be subsequently communicated to the transmitter at e.g., system startup.

Electronic Hardware Correction

Factory calibration correction techniques for continuous analyte monitoring systems have typically employed digital techniques for storing and adjusting for sensor lot variability. In some embodiments it is useful to use analog electronic circuitry to modify the sensor signal. Using a resistor with a known value can serve to modify an analog signal and change the amount of current or the measured voltage. In one example the resistor may be combined as part of a gain circuit with an operational amplifier to tune the gain on the output signal. The resistor can be selected from a variety of known resistance values or configured through a process (e.g. laser trimmed resistor).

Factors Influencing Sensitivity and Impedance

A nonlimiting set of factors that have been found to influence the impedance and/or sensitivity of a preconnected analyte sensor is shown in the Table of FIG. [IFD1675]. These factors, which are directed to select manufacturing and storage conditions, can be measured for individual sensors and/or sensor lots and correlated with sensitivity and impedance measurements at different times during the sensor lifetime. In this way the values of these factors may be used individually and/or in combination with one another to determine the relationship between the measured impedance and sensitivity at any time during the sensor lifetime, thereby allowing adjustments to the calibration factor that is used to calibrate the sensor at any time during its operational life.

Updating of Slope Parameters on a Regular Basis

Currently, a "cal check" procedure is performed in the factory in which a sensor undergoes in vitro calibration to obtain a slope value. This value is used to seed a joint probability algorithm with initial and final sensitivity values using linear transformations. That is:

$$\text{Mean Initial Slope}=\text{calcheck}*m\text{start}+b\text{start}$$

$$\text{Mean Final Slope}=\text{calcheck}*m\text{final}+b\text{final}$$

Deviations from this linear relationship can be taken into account by updating the mean of the initial and final slope using a linear combination of parameters measured at the factory (e.g. during cal check) and parameters measured in real time. For instance, the equation for the final slope can be revised as:

$$\text{Mean Final Slope}=a*\text{calcheck}+b*\text{meanSensorCurrent}+c*\text{sigmaSensorCurrent}+d*\text{sensorCv}+e*\text{calcheck}+\ldots+\text{Offset}$$

where the real time parameters include the mean sensor current (meanSensorCurrent), the standard deviation of the sensor current (signaSensorCurrent) and the coefficient of variation of the sensor current (sensorCv). Other real time parameters that may be included in the mean final slope include mean sensor current, the root mean square of the sensor current, and the sensor current taken at a specified percentile within the distribution of sensor current values. A similar approach can be taken to adjust the mean of the starting sensitivity. By using a combination of factory and real-time measurements in this way, the performance of the system can be improved because the linear combinations allows factory information to be linked with in-vivo sensor measurements. The parameters that describe the equation below may be such that the final slope estimate may be updated periodically (e.g., every day) during sensor wear.

Retrospective Calibration of CGM Signal

Retrospectively calibrating the CGM signal with or without the use of SMBG is important for the professional CGM market and other use cases such as technical support and for benchmarking the performance of factory calibrated CGM. With retrospective calibration, there is an opportunity to remove certain artifacts that corrupt the real-time CGM signal, such as time-lag, transient faults, compression, noise, and data gaps. As described below, in some embodiments data gaps, noise and artifacts in the CGM signal can be removed using prediction algorithms. This approach generally works best after the removal of time lag from the signal and smoothing.

It is commonly believed that glucose levels can be predicted reasonably well about 30 minutes into future. The accuracy of the predicted signal drops as the prediction horizon goes beyond 30 to 40 minutes. Thus, any signal artifacts or data gaps that are shorter than 30-40 minutes can be replaced with a predicted signal without losing key information need for clinical use. Further, given the retrospective use, any errors in the predicted glucose level may be removed by the analysis of data. Some ways that can be accomplished are as follows:

1. Identify the area(s) of artifacts in the signal.
2. Replace the artifact signal with a predicted glucose level.
3. Evaluate the difference between the predicted glucose level at a final point in time and an initial point in time of the post artifact signal.
4. Correct the predicted signal by feeding back this error into the prediction. For example, if there is an error of 30 mg/dL between the final predicted CGM and the initial time point of post-artifact CGM, this error can be distributed evenly (or using a weighted average) over the duration of the predicted signal. This way, the predicted signal is corrected to result in a smooth correction of the artifact, without discontinuities.

In another embodiment, prediction can be used bidirectionally, to increase the duration of the artifacts that can be corrected. The following describes how longer duration artifacts may be corrected:

1. Identify the beginning and end of artifacts that need removal/replacement.
2. Create two CGM time series signals, the first time series being the normal signal (time moving forward from the beginning to the end of session) and the second time series being in reverse time (from the end of the session to the beginning).
3. Use the prediction to replace artifacts on both the forward and reverse time series. i.e., each artifact will have two possible replacements, one based on the forward time series signal and one based on the reverse time series signal.
4. Pick the midway point between the two replaced artifacts. These should correspond to the same time point in the CGM signal. Depending on how variable the glucose signal is during this period, the two signals may be meet at the midway point or be different at the midway point.
5. Given that the prediction is reasonably accurate for short durations, the best estimate of the glucose level at the midway point is the mean of the values from the two time series.
6. Now, the error between the mean and the actual midpoint values from the time series can be fed back into the predicted artifact replacements to correct them.
7. The corrections can be weighted depending on the quality of the signal before or after the artifact.

This approach for the correction of artifacts makes the signal more reliable and increases the duration of artifacts that can be correct/removed.

Replacement Sensors

Sensors sometimes fail before their marketed duration (e.g. 7 days). In some cases the sensor electronics (e.g., a transmitter) can be packaged with a 3 month supply of sensors in a single box (e.g. a 6 pack). In one variant, the transmitter can then be coded with a single common sensor code. If one of the sensors in that sensor box fails and a replacement sensor needs to be sent to the customer, the transmitter can send the sensor code to the dedicated app on the customer's mobile device. The customer can then ask for a replacement sensor through the app. The app can then relay the sensor code to the manufacturer or the like, who can send the customer the appropriate sensor with the correct code that matches the transmitter that was included in the original sensor box.

Configurable Calibration Frequency

In one variant, the frequency at which a transmitter issues a calibration request to the dedicated app on the customer's mobile device can be configurable. In one example, the transmitter can have a default calibration frequency (e.g., one calibration per day, two calibrations on day one followed by one calibration per day thereafter, etc.) if it has not been supplied with pre-existing calibration information. In another example the transmitter may or may not issue calibration requests to the dedicated app based on the availability of the pre-existing calibration information. Moreover, the calibration frequency may be based on the type of app being run on the mobile device. The transmitter may also store different default calibration frequencies based on the type of app being used.

Transfer of Calibration Data to the Transmitter

In another variant, a method for transferring calibration coefficients to the transmitter or other sensor electronics from a disposable sensor without user intervention may operate as follows. This method employs a memory embedded in the sensor which transfers the calibration coefficients and/or other information to the transmitter. The information that may be transferred could include, for example, a lot number, expiration dates, and the authentication information that could allow the manufacturer to assure that genuine sensors are being used. Such authentication information may operate in accordance with cryptographic and other algorithms such as hashes (e.g., SHA-256) and/or may operate in accordance with standards such as the Federal Information Processing Standards.

While the information may be transmitted from the sensor to the transmitter using any suitable connector or wirelessly using, for instance, RFID, these are not always appropriate for low cost, environmentally robust systems and may require significant development or tooling changes. Instead, the following technique may be employed to transfer calibration codes and/or other information.

Without loss of generality, this technique will be described as being applicable to a sensor that uses a low bias voltage (e.g., less than 1 volt) and has at least 2 electrical connectors (e.g., a reference and working electrode). The sensor is assumed to be wired or otherwise configured with a memory element in which the information is stored. The memory element uses a single wire for power and signal and is connected to the sensor's working electrode. A ground connection is connected to the sensor's reference electrode.

To initiate a session, the transmitter periodically checks for the presence of a new sensor by waking up from sleep mode, enabling the bias voltage and looking for a predetermined response from the sensor. If the response indicates the presence of a new sensor, the transmitter will transition into an operating mode as described below. If the response is not as expected, indicating no sensor present, the transmitter will go back to sleep for a predetermined period.

If a predetermined signal indicates the presence of a new sensor, the transmitter will attempt to recover calibration coefficients and other information from the memory device. The memory device is configured to only respond to signal pulses if they are above a predetermined voltage level, above the nominal operating bias voltage of the sensor. The memory device is both powered and communicates using the same pin. The memory device may operate in an active mode, where it incorporates a short term charge storage device (such as a capacitor) to power the memory chip while it signals back to the transmitter while the transmitter places its pin connected to the memory element in high impedance. Alternatively, the memory device may operate in a passive mode and present a high or low load to the transmitter in order to signal the appropriate information back to the transmitter, using the transmitter as the master clock.

The time needed to communicate the relevant calibration coefficients and any other information (such as expiration date, serial number) is generally short relative to the lifetime of the sensor, and the higher voltages used during communication for such a short time will not damage any enzymes used in the sensor. Hence the short term overpotential does not affect the long term operation of the sensor, and may even help with sensor electrochemical break in. Once the memory device has passed the required information and the transmitter ramps down to the nominal sensor bias voltage, it either may enter a very high impedance state so as not to falsely elevate the observed signal current from the sensor, or it may be designed to draw a known current which can be subtracted from the sensor signal, or it may do a combination of both.

In some embodiments, the transmitter may signal to the memory element the end of life of the sensor, which will place an indicator or the like in its internal memory indicating that the sensor is expired. This can prevent accidental reuse of the sensor since the memory element will communicate to the transmitter that it has already been used, even if it is disconnected and reconnected. At this point the duration of the communication session and the value of the applied voltage is less crucial since it does not matter if the enzyme is damaged, since the sensor has already reached its end of life.

In an alternative embodiment, when initiating a session, the transmitter, upon waking up, may simply interrogate the connections for the presence of a memory device, and later check that the sensor is operating normally once the calibration data has been successfully transferred.

Calibration of EGV in a Closed-Loop System

In closed-loop systems (e.g., artificial pancreas systems), updating estimated glucose values (EGVs) as a result of a calibration can lead to incorrect dosing because when a calibration happens, the EGVs are likely to change more than natural glucose levels change. When such changes in EGVs are input to artificial pancreas algorithms, they may lead them to incorrectly predict EGVs. Current artificial pancreas algorithms accept calibration updates and update the EGVs after the calibration is completed.

This problem can be addressed in some embodiments by updating a few EGV data points prior to calibration as well as after calibration for use by the artificial pancreas algorithms. In this way the algorithms can capture the correct EGV changes.

Use of Biometric Data in Preventing Incorrect Entry of Calibration Data

Manual entry of calibration data or other reference information can be prone to error. One way to detect and prevent the use of incorrectly entered data may use biometric data of the user. Such information may be available to the dedicated app on the user's mobile device, either from sensors incorporated in the mobile device or from third party devices that are able to provide the biometric data to the mobile device. If the calibration or other data that is entered is found to be incompatible or inconsistent with the biometric data, the app can present an error message or take other appropriate action. As a simple example, if a 35 year old male is found from a biometric sensor to have a heart rate of 170 bpm and the CGM shows a glucose reading of 40 mg/dl, this is indicative that the glucose reading is in error.

Efficient Storage of Calibration Coefficients and Other Parameters

The transmitter needs to store relevant calibration coefficients and/or other parameters for different sensors. When a sensor is inserted, the user typically enters the sensor ID into the dedicated app and the app in turn sends either the parameters to the transmitter or an identifier that corresponds to a predefined set of parameters already stored in or otherwise available to the transmitter. In any case, the transmitter may need to store multiple sets of parameters. However, if the set or sets of parameters are large, there may not be sufficient memory available to the transmitter to store all the necessary parameters.

In one variant, the transmitter may store a limited number (e.g., one) of sets of parameters that can serve as default sets of parameters. Then, when a newer set of parameters are to be used, only the differences between the values in the default set of parameters and the new set of parameters need to be stored in the transmitter. Since the differences are usually going to be small, this can be a more efficient way to store the data. This also provides the flexibility to change any parameters since the parameters established during factory calibration do not have to remain fixed. In one embodiment, the default set of parameters can be provided as an ordered list and the changes can be provided as a list of paired values that specify the parameter number and the value of the difference from the default value.

Exemplary Sensor System Configurations

Embodiments of the present invention are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

In some embodiments, a sensor system is provided for continuous measurement of an analyte (e.g., glucose) in a host that includes: a continuous analyte sensor configured to continuously measure a concentration of the analyte in the host and a sensor electronics module physically connected to the continuous analyte sensor during sensor use. In one embodiment, the sensor electronics module includes electronics configured to process a data stream associated with an analyte concentration measured by the continuous analyte sensor in order to process the sensor data and generate displayable sensor information that includes raw sensor data, transformed sensor data, and/or any other sensor data, for example. The sensor electronics module can include electronics configured to process a data stream associated with an analyte concentration measured by the continuous analyte sensor in order to process the sensor data that may include raw sensor data, algorithm processed, transformed sensor data, and/or any other sensor data, for example. The sensor electronics module can include a processor and computer-readable program instructions to implement the processes discussed herein, including the functions specified in the flowchart block or blocks presented herein.

In some embodiments, a receiver, which can also be referred to as a display device, is in communication with the sensor electronics module (e.g., via wired or wireless communication). The receiver can be an application-specific portable device, or a general purpose device, such as a P.C., smart phone, tablet computer, smart watch, wearable display, haptic device and the like. In one embodiment, a receiver can be in data communication with the sensor electronics module for receiving sensor data, such as raw and/or processed data, and include a processing module for processing and/or display the received data. The receiver can also include an input module configured to receive input, such as calibration codes, reference analyte values, and any other information discussed herein, from a user via an input method (e.g. keyboard or touch-sensitive display screen), and can also be configured to receive information from external devices, such as insulin pumps, insulin pens, wearable sensors, connected devices, accelerometers, and reference meters, via wired or wireless data communication. The input can be processed alone or in combination with information received from the sensor electronics module. The receiver's processing module can include a processor and computer program instructions to implement any of the processes discussed herein, including the functions specified in the flowchart block or blocks presented herein.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A preconnected sensor assembly comprising:
    a sensor having at least one electrical contact, the sensor configured to sense an analyte concentration;
    a housing;
    sensor electronics;
    an interposer having:
        a substrate to mechanically interface the sensor with the sensor electronics, and
        a contact electrically coupled with the at least one electrical contact of the sensor, the contact disposed on an external surface of the interposer, the contact configured to electrically interface the sensor with the sensor electronics; and
    a package, the sensor and the sensor electronics being positioned within the package, the sensor preconnected to the sensor electronics via the interposer,
    wherein the substrate of the interposer is configured to mechanically interface with the housing and with one or more manufacturing equipment for allowing measurement of at least one sensor property via the interposer.

2. The sensor assembly of claim 1, further comprising a battery preconnected to a sensor wire and/or the sensor electronics.

3. The sensor assembly of claim 2, further comprising a radio preconnected to the battery, the sensor wire, and/or sensor electronics.

4. A method of calibrating the sensor associated with the preconnected sensor assembly of claim 1, wherein the sensor experiences a plurality of life phases including manufacture, shipping, storage, and insertion in a user as part of a sensor session, comprising:
- disposing measurement electronics in operable connection to the sensor;
- determining a first calibration factor during the manufacture life phase, wherein the manufacture life phase includes manufacturing the sensor in a factory;
- determining a second calibration factor during the shipping life phase and/or the storage life phase; and
- upon insertion in the user, using a combination calibration factor in a user monitoring device to calibrate signals from the sensor, wherein the combination calibration factor is based on both the first calibration factor and the second calibration factor.

5. The method of claim 4, further comprising storing the first calibration factor in the sensor electronics or in the measurement electronics associated with the sensor assembly.

6. The method of claim 4, wherein the measurement electronics form a part of the sensor electronics.

7. The method of claim 4, wherein the measurement electronics is disposed within a common package as the sensor electronics.

8. The method of claim 4, further comprising disposing the sensor assembly and the measurement electronics in a package for shipping.

9. The method of claim 4, wherein the user monitoring device is a dedicated receiver or a smart phone.

10. The method of claim 9, further comprising transmitting the combination calibration factor from the sensor electronics or the measurement electronics to the dedicated receiver or the smart phone.

11. The method of claim 4, further comprising storing the second calibration factor within the measurement electronics or the sensor electronics.

12. The method of claim 4, further comprising transmitting the combination calibration factor, or the second calibration factor, or both, to the factory, to cause a change in one of a plurality of manufacturing parameters, or further comprising transmitting the combination calibration factor to a cloud server.

13. The method of claim 4, wherein the determining the second calibration factor is performed by the measurement electronics.

14. The method of claim 4, wherein the first calibration factor is a system level calibration factor pertaining to the calibration of all components in the sensor assembly.

15. The method of claim 12, wherein the transmitting further comprises transmitting a sensor tracking number or serial number to the cloud server or to the factory along with the combination calibration factor, whereby a lot associated with the sensor can be identified.

16. The method of claim 4, wherein the measurement electronics are configured to detect faults in the sensor electronics or the sensor.

17. The method of claim 16, further comprising transmitting data about the detected faults in the sensor electronics or the sensor to the user monitoring device.

18. The method of claim 16, further comprising modifying the combination calibration factor stored in the user monitoring device to compensate for the detected fault.

19. The method of claim 4, wherein the measurement electronics is configured to detect electrical signals from the sensor, the sensor electronics, the housing, or a combination thereof.

20. The method of claim 4, wherein the combination calibration factor is configured to correct for individual variations of an in vivo sensor.

21. The method of claim 4, wherein the first calibration factor or the second calibration factor, or both, are indicative of a measured impedance.

22. The method of claim 21, wherein the measured impedance is performed by measuring a step response at a single frequency or at multiple frequencies.

23. The method of claim 22, further comprising determining a third calibration factor prior to shipping of the sensor, and wherein the third calibration factor is indicative of impedance.

24. The method of claim 4, wherein the first calibration factor or the second calibration factor, or both, are indicative of a measured temperature or of a measured humidity.

25. The method of claim 4, wherein the combination calibration factor is used to calculate a modified calibration value, detect physical damage to the sensor, or detect exposure of the sensor assembly to temperature and/or humidity.

26. The method of claim 4, wherein the combination calibration factor is an adaptive value that combines calibration values collected during sensor manufacturer and conditions experienced during a time from sensor manufacturer to sensor insertion.

27. The method of claim 4, further comprising selecting the user among a plurality of users to receive the sensor based on the first calibration factor, whereby population data or individual user data determines that the sensor with the first calibration factor is optimized for the user.

28. The method of claim 27, wherein an average glucose level for the user is determined, and wherein the first calibration factor for the sensor is associated with a sensitivity of the sensor.

29. The method of claim 4, wherein the manufacture life phase includes a packaging phase in which the preconnected sensor assembly is packaged in a sterile package, the first calibration factor being determined after the preconnected sensor assembly is packaged in the sterile package.

30. A method of calibrating the sensor associated with the preconnected sensor assembly of claim 1, wherein the sensor experiences a plurality of life phases including manufacture, shipping, storage, and insertion in a user as part of a sensor session, comprising:
- disposing measurement electronics in operable connection to the sensor electronics;
- determining a first calibration factor during the manufacture life phase, wherein the manufacture life phase includes manufacturing the sensor in a factory;
- determining a second calibration factor during the shipping life phase and/or the storage life phase; and
- upon insertion in the user, calculating a combination calibration factor and storing the combination calibration factor in the sensor electronics, wherein the combination calibration factor is based on both the first calibration factor and the second calibration factor, wherein the combination calibration factor is configured to provide a conversion between a detected signal from the sensor and an analyte concentration in the user.

31. The method of claim 30, further comprising displaying an indication of the analyte concentration, wherein the displaying occurs on a user monitoring device in signal communication with the sensor electronics, and wherein the user monitoring device is a dedicated receiver or a smart phone.

32. An improved method of manufacturing a sensor assembly including a sensor, and sensor electronics, comprising:
preconnecting the sensor to at least a portion of the sensor electronics via an interposer, wherein the interposer is shaped in order to mechanically and electronically engage with a manufacturing equipment associated with the sensor, wherein preconnecting the sensor comprises mechanically and electrically interfacing the sensor to the sensor electronics with the interposer;
monitoring one or more manufacturing parameters during manufacturing of the sensor assembly;
receiving a calibration factor associated with the sensor after the sensor has finished manufacturing; and
modifying the one or more manufacturing parameters during subsequent manufacturing processes used to manufacture additional sensor assemblies, the modifying being based at least in part on the monitored one or more manufacturing parameters and the received calibration factor.

33. The method of claim 32, further comprising a battery and a radio, wherein the battery and the radio remain disconnected from the sensor.

34. The method of claim 33, further comprising preconnecting the battery to the sensor and the portion of the sensor electronics sufficient to monitor manufacturing parameters.

35. The method of claim 32, further comprising a battery and a radio, wherein the radio is preconnected to the battery, the sensor, and the portion of the sensor electronics.

36. The method of claim 32, wherein a combined error of the preconnected sensor and the portion of the sensor electronics sufficient to monitor manufacturing parameters is less than a propagated or summed error of the sensor and the portion of the sensor electronics sufficient to monitor manufacturing parameters considered individually.

* * * * *